(12) United States Patent
Salazar et al.

(10) Patent No.: US 12,232,874 B2
(45) Date of Patent: Feb. 25, 2025

(54) ELECTRODE APPARATUS FOR DIAGNOSIS OF ARRHYTHMIAS

(71) Applicant: Biosense Webster (Israel) Ltd., Yokneam (IL)

(72) Inventors: Henry F. Salazar, Montclair, CA (US); Dustin R. Tobey, San Dimas, CA (US); Shubhayu Basu, Anaheim, CA (US); Sean D. Thaler, Rancho Cucamonga, CA (US); Joseph R. Wong, South Pasadena, CA (US); Daniele Ghidoli, Irwindale, CA (US); Pieter Emmelius Van Niekerk, Monrovia, CA (US); Jamie Lynn Malinaric, Pasadena, CA (US); Cesar Fuentes-Ortega, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 378 days.

(21) Appl. No.: 17/029,752

(22) Filed: Sep. 23, 2020

(65) Prior Publication Data

US 2021/0369339 A1    Dec. 2, 2021

Related U.S. Application Data

(60) Provisional application No. 63/052,553, filed on Jul. 16, 2020, provisional application No. 63/031,955, filed on May 29, 2020.

(51) Int. Cl.
*A61B 18/12* (2006.01)
*A61B 5/283* (2021.01)
(Continued)

(52) U.S. Cl.
CPC .......... *A61B 5/283* (2021.01); *A61B 18/1492* (2013.01); *A61B 2017/00526* (2013.01);
(Continued)

(58) Field of Classification Search
CPC ................ A61B 5/283; A61B 18/1492; A61B 2017/00526; A61B 2018/00077;
(Continued)

(56) References Cited

U.S. PATENT DOCUMENTS 4,699,147 A    10/1987 Chilson et al.
4,940,064 A    7/1990 Desai
(Continued)

FOREIGN PATENT DOCUMENTS

CN    102665586 A    9/2012
CN    102892453 A    1/2013
(Continued)

OTHER PUBLICATIONS

International Search Report & Written Opinion dated Oct. 21, 2022, from corresponding International PCT Application No. PCT/IB2022/056738.
(Continued)

*Primary Examiner* — Daniel W Fowler

(57) ABSTRACT

An apparatus includes an end effector having loop members with electrodes thereon and is usable with catheter-based systems to measure or provide electrical signals. The end effector can include three loop members that are non-coplanar when expanded unconstrained that become contiguous to a planar surface when the loop members are deflected against the surface, a mechanical linkage that joins the loop members at a distal vertex of the end effector, electrodes having surface treatment to enhance surface roughness of the electrodes, twisted pair electrode wires, a bonded spine cover, and/or any combination thereof.

18 Claims, 30 Drawing Sheets

(51) Int. Cl.
  *A61B 18/14* (2006.01)
  *A61B 17/00* (2006.01)
  *A61B 18/00* (2006.01)

(52) U.S. Cl.
  CPC ............. *A61B 2018/00077* (2013.01); *A61B 2018/00083* (2013.01); *A61B 2018/00178* (2013.01); *A61B 2018/00267* (2013.01); *A61B 2018/00351* (2013.01); *A61B 2018/00577* (2013.01); *A61B 2018/00839* (2013.01); *A61B 2018/1407* (2013.01); *A61B 2018/1467* (2013.01); *A61B 2218/002* (2013.01); *A61B 2562/0209* (2013.01)

(58) Field of Classification Search
  CPC .......... A61B 2018/00083; A61B 2018/00178; A61B 2018/00267; A61B 2018/00351; A61B 2018/00839; A61B 2018/1407; A61B 2018/1467; A61B 2218/002; A61B 2562/0209
  See application file for complete search history.

(56) References Cited

U.S. PATENT DOCUMENTS

| | | | |
|---|---|---|---|
| 5,215,103 | A | 6/1993 | Desai |
| 5,255,679 | A | 10/1993 | Imran |
| 5,293,869 | A | 3/1994 | Edwards et al. |
| 5,309,910 | A | 5/1994 | Edwards et al. |
| 5,324,284 | A | 6/1994 | Imran |
| 5,345,936 | A | 9/1994 | Pomeranz et al. |
| 5,365,926 | A | 11/1994 | Desai |
| 5,391,199 | A | 2/1995 | Ben-Haim |
| 5,396,887 | A | 3/1995 | Imran |
| 5,400,783 | A | 3/1995 | Pomeranz et al. |
| 5,411,025 | A | 5/1995 | Webster, Jr. |
| 5,415,166 | A | 5/1995 | Imran |
| 5,443,489 | A | 8/1995 | Ben-Haim |
| 5,456,254 | A | 10/1995 | Pietroski et al. |
| 5,465,717 | A | 11/1995 | Imran et al. |
| 5,476,495 | A | 12/1995 | Kordis et al. |
| 5,499,981 | A | 3/1996 | Kordis |
| 5,526,810 | A | 6/1996 | Wang |
| 5,546,940 | A | 8/1996 | Panescu et al. |
| 5,549,108 | A | 8/1996 | Edwards et al. |
| 5,558,073 | A | 9/1996 | Pomeranz et al. |
| 5,558,091 | A | 9/1996 | Acker et al. |
| 5,577,509 | A | 11/1996 | Panescu et al. |
| 5,595,183 | A | 1/1997 | Swanson et al. |
| 5,598,848 | A | 2/1997 | Swanson et al. |
| 5,609,157 | A | 3/1997 | Panescu et al. |
| 5,628,313 | A | 5/1997 | Webster, Jr. |
| 5,630,918 | A * | 5/1997 | Takahara et al. |
| 5,681,280 | A | 10/1997 | Rusk et al. |
| 5,702,438 | A | 12/1997 | Avitall |
| 5,722,401 | A | 3/1998 | Pietroski et al. |
| 5,722,403 | A | 3/1998 | McGee et al. |
| 5,725,525 | A | 3/1998 | Kordis |
| 5,730,128 | A | 3/1998 | Pomeranz et al. |
| 5,738,096 | A | 4/1998 | Ben-Haim |
| 5,782,899 | A | 7/1998 | Imran |
| 5,881,727 | A | 3/1999 | Edwards |
| 5,893,847 | A | 4/1999 | Kordis |
| 5,904,680 | A | 5/1999 | Kordis et al. |
| 5,911,739 | A | 6/1999 | Kordis et al. |
| 5,928,228 | A | 7/1999 | Kordis et al. |
| 5,944,022 | A | 8/1999 | Nardella et al. |
| 5,964,757 | A | 10/1999 | Ponzi |
| 5,968,040 | A | 10/1999 | Swanson et al. |
| 5,983,126 | A | 11/1999 | Wittkampf |
| 6,014,579 | A | 1/2000 | Pomeranz et al. |
| 6,014,590 | A | 1/2000 | Whayne et al. |
| 6,071,280 | A | 6/2000 | Edwards et al. |
| 6,071,282 | A | 6/2000 | Fleischman |
| 6,119,030 | A | 9/2000 | Morency |
| 6,123,699 | A | 9/2000 | Webster, Jr. |
| 6,142,993 | A | 11/2000 | Whayne et al. |
| 6,171,277 | B1 | 1/2001 | Ponzi |
| 6,172,499 | B1 | 1/2001 | Ashe |
| 6,183,435 | B1 | 2/2001 | Bumbalough et al. |
| 6,183,463 | B1 | 2/2001 | Webster, Jr. |
| 6,198,974 | B1 | 3/2001 | Webster, Jr. |
| 6,210,407 | B1 | 4/2001 | Webster |
| 6,216,043 | B1 | 4/2001 | Swanson et al. |
| 6,216,044 | B1 | 4/2001 | Kordis |
| 6,239,724 | B1 | 5/2001 | Doron et al. |
| 6,245,068 | B1 | 6/2001 | Olson et al. |
| 6,267,746 | B1 | 7/2001 | Bumbalough |
| 6,332,089 | B1 | 12/2001 | Acker et al. |
| 6,415,187 | B1 | 7/2002 | Kuzma et al. |
| 6,428,537 | B1 | 8/2002 | Swanson et al. |
| 6,445,864 | B2 | 9/2002 | Jiang et al. |
| 6,484,118 | B1 | 11/2002 | Govari |
| 6,522,932 | B1 | 2/2003 | Kuzma et al. |
| 6,574,492 | B1 | 6/2003 | Ben-Haim et al. |
| 6,584,345 | B2 | 6/2003 | Govari |
| 6,590,963 | B2 | 7/2003 | Mohammadian et al. |
| 6,600,948 | B2 | 7/2003 | Ben-Haim et al. |
| 6,618,612 | B1 | 9/2003 | Acker et al. |
| 6,658,302 | B1 | 12/2003 | Kuzma et al. |
| 6,690,963 | B2 | 2/2004 | Ben-Haim et al. |
| 6,738,655 | B1 | 5/2004 | Sen et al. |
| 6,741,878 | B2 | 5/2004 | Fuimaono et al. |
| 6,748,255 | B2 | 6/2004 | Fuimaono et al. |
| 6,780,183 | B2 | 8/2004 | Jimenez, Jr. et al. |
| 6,788,967 | B2 | 9/2004 | Ben-Haim et al. |
| 6,837,886 | B2 | 1/2005 | Collins et al. |
| 6,866,662 | B2 | 3/2005 | Fuimaono et al. |
| 6,892,091 | B1 | 5/2005 | Ben-Haim et al. |
| 6,961,602 | B2 | 11/2005 | Fuimaono et al. |
| 6,970,730 | B2 | 11/2005 | Fuimaono et al. |
| 6,973,340 | B2 | 12/2005 | Fuimaono et al. |
| 6,980,858 | B2 | 12/2005 | Fuimaono et al. |
| 7,048,734 | B1 | 5/2006 | Fleischman et al. |
| 7,099,712 | B2 | 8/2006 | Fuimaono et al. |
| 7,149,563 | B2 | 12/2006 | Fuimaono et al. |
| 7,155,270 | B2 | 12/2006 | Solis et al. |
| 7,255,695 | B2 | 8/2007 | Falwell et al. |
| 7,257,434 | B2 | 8/2007 | Fuimaono et al. |
| 7,257,435 | B2 | 8/2007 | Plaza |
| 7,366,557 | B2 | 4/2008 | Bautista |
| 7,399,299 | B2 | 7/2008 | Daniel et al. |
| 7,412,274 | B2 | 8/2008 | Mejia |
| 7,429,261 | B2 | 9/2008 | Kunis et al. |
| 7,522,950 | B2 | 4/2009 | Fuimaono et al. |
| 7,536,218 | B2 | 5/2009 | Govari et al. |
| RE41,334 | E | 5/2010 | Beatty et al. |
| 7,756,567 | B2 | 7/2010 | Kuduvalli et al. |
| 7,756,576 | B2 | 7/2010 | Levin |
| 7,846,157 | B2 | 12/2010 | Kozel |
| 7,848,757 | B2 | 12/2010 | Duggi et al. |
| 7,848,787 | B2 | 12/2010 | Osadchy |
| 7,869,865 | B2 | 1/2011 | Govari et al. |
| 7,930,018 | B2 | 4/2011 | Harlev et al. |
| 8,007,495 | B2 | 8/2011 | McDaniel et al. |
| 8,048,063 | B2 | 11/2011 | Aeby et al. |
| 8,103,327 | B2 | 1/2012 | Harlev et al. |
| 8,167,845 | B2 | 5/2012 | Wang et al. |
| 8,206,404 | B2 | 6/2012 | De La Rama et al. |
| 8,224,416 | B2 | 7/2012 | De La Rama et al. |
| 8,235,988 | B2 | 8/2012 | Davis et al. |
| 8,271,099 | B1 | 9/2012 | Swanson |
| 8,273,084 | B2 | 9/2012 | Kunis et al. |
| 8,346,339 | B2 | 1/2013 | Kordis et al. |
| 8,391,947 | B2 | 3/2013 | Urman et al. |
| 8,435,232 | B2 | 5/2013 | Aeby et al. |
| 8,447,377 | B2 | 5/2013 | Harlev et al. |
| 8,456,182 | B2 | 6/2013 | Bar-Tal et al. |
| 8,480,669 | B2 | 7/2013 | Pappone et al. |
| 8,498,686 | B2 | 7/2013 | Grunewald |
| 8,517,999 | B2 | 8/2013 | Pappone et al. |
| 8,545,490 | B2 | 10/2013 | Mihajlovic et al. |
| 8,560,086 | B2 | 10/2013 | Just et al. |

(56) References Cited

U.S. PATENT DOCUMENTS

| | | | |
|---|---|---|---|
| 8,565,851 B2 | 10/2013 | Lau et al. |
| 8,567,265 B2 | 10/2013 | Aeby et al. |
| 8,571,626 B2 | 10/2013 | Lau et al. |
| 8,603,069 B2 | 12/2013 | Selkee |
| 8,712,550 B2 | 4/2014 | Grunewald |
| 8,715,279 B2 | 5/2014 | De La Rama et al. |
| 8,734,440 B2 | 5/2014 | Wu |
| 8,744,599 B2 | 6/2014 | Tegg |
| 8,755,861 B2 | 6/2014 | Harlev et al. |
| 8,764,742 B2 | 7/2014 | Pappone et al. |
| 8,790,341 B2 | 7/2014 | Pappone et al. |
| 8,825,130 B2 | 9/2014 | Just et al. |
| 8,827,910 B2 | 9/2014 | De La Rama et al. |
| 8,906,011 B2 | 12/2014 | Gelbart et al. |
| 8,945,120 B2 | 2/2015 | McDaniel et al. |
| 8,956,353 B2 | 2/2015 | Govari et al. |
| 8,974,454 B2 | 3/2015 | De La Rama et al. |
| 8,979,837 B2 | 3/2015 | De La Rama et al. |
| 8,979,839 B2 | 3/2015 | De La Rama et al. |
| 9,037,264 B2 | 5/2015 | Just et al. |
| 9,044,245 B2 | 6/2015 | Condie et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,480,416 B2 | 11/2016 | Govari et al. |
| 9,480,491 B1* | 11/2016 | Dostal et al. |
| 9,486,282 B2 | 11/2016 | Solis |
| 9,554,718 B2 | 1/2017 | Bar-Tal et al. |
| 9,561,075 B2 | 2/2017 | Pappone et al. |
| D782,686 S | 3/2017 | Werneth et al. |
| 9,585,588 B2 | 3/2017 | Marecki et al. |
| 9,597,036 B2 | 3/2017 | Aeby et al. |
| 9,616,199 B2 | 4/2017 | Wang et al. |
| 9,642,675 B2 | 5/2017 | Werneth et al. |
| 9,687,297 B2 | 6/2017 | Just et al. |
| 9,693,733 B2 | 7/2017 | Altmann et al. |
| 9,713,418 B2 | 7/2017 | Huszar et al. |
| 9,724,492 B2 | 8/2017 | De La Rama et al. |
| 9,782,099 B2 | 10/2017 | Williams et al. |
| 9,788,895 B2 | 10/2017 | Solis |
| 9,801,585 B2 | 10/2017 | Shah et al. |
| 9,801,681 B2 | 10/2017 | Laske et al. |
| 9,814,618 B2 | 11/2017 | Nguyen et al. |
| 9,820,664 B2 | 11/2017 | Hoitink et al. |
| 9,833,161 B2 | 12/2017 | Govari |
| 9,833,608 B2 | 12/2017 | Masson |
| 9,848,795 B2 | 12/2017 | Marecki et al. |
| 9,877,781 B2 | 1/2018 | Grasse et al. |
| 9,894,756 B2 | 2/2018 | Weinkam et al. |
| 9,895,073 B2 | 2/2018 | Solis |
| 9,907,480 B2 | 3/2018 | Basu et al. |
| 9,907,609 B2 | 3/2018 | Cao et al. |
| 9,949,656 B2 | 4/2018 | Wu et al. |
| 9,962,224 B2 | 5/2018 | Pappone et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,039,598 B2 | 8/2018 | De La Rama et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,130,422 B2 | 11/2018 | Ditter |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,220,187 B2 | 3/2019 | De La Rama et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,433,903 B2 | 10/2019 | Pappone et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,729 B2 | 12/2019 | De La Rama et al. |
| 10,492,857 B2 | 12/2019 | Guggenberger et al. |
| 10,537,259 B2 | 1/2020 | Wu et al. |
| 10,542,620 B2 | 1/2020 | Weinkam et al. |
| 10,575,743 B2 | 3/2020 | Basu et al. |
| 10,575,745 B2 | 3/2020 | Solis |
| 10,576,244 B2 | 3/2020 | De La Rama et al. |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,700 B2 | 5/2020 | Beeckler et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,177 B2 | 7/2020 | Aujla |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,842,990 B2 | 11/2020 | De La Rama et al. |
| 10,857,349 B2 | 12/2020 | De La Rama et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,708 B2 | 7/2021 | Busu et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2001/0001314 A1 | 5/2001 | Davison et al. |
| 2003/0236455 A1 | 12/2003 | Swanson et al. |
| 2004/0199200 A1* | 10/2004 | Teague et al. |
| 2004/0210121 A1 | 10/2004 | Fuimaono et al. |
| 2004/0254572 A1 | 12/2004 | McIntyre et al. |

(56) References Cited

U.S. PATENT DOCUMENTS

| | | |
|---|---|---|
| 2005/0159741 A1 | 7/2005 | Paul et al. |
| 2006/0100669 A1 | 5/2006 | Fuimaono et al. |
| 2006/0253117 A1 | 11/2006 | Hovda et al. |
| 2007/0093806 A1 | 4/2007 | Desai et al. |
| 2007/0255273 A1* | 11/2007 | Fernandez et al. |
| 2007/0276212 A1 | 11/2007 | Fuimaono et al. |
| 2008/0249463 A1 | 10/2008 | Pappone et al. |
| 2008/0249522 A1 | 10/2008 | Pappone et al. |
| 2008/0294158 A1 | 11/2008 | Pappone et al. |
| 2009/0012517 A1 | 1/2009 | De La Rama et al. |
| 2009/0198300 A1 | 8/2009 | Zhang et al. |
| 2010/0076426 A1 | 3/2010 | de la Rama et al. |
| 2010/0152731 A1 | 6/2010 | De La Rama et al. |
| 2010/0174177 A1 | 7/2010 | Wu |
| 2010/0286684 A1 | 11/2010 | Hata et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0288392 A1 | 11/2011 | De La Rama et al. |
| 2011/0301597 A1 | 12/2011 | McDaniel et al. |
| 2011/0313417 A1 | 12/2011 | De La Rama et al. |
| 2012/0010490 A1 | 1/2012 | Kauphusman et al. |
| 2012/0130217 A1 | 5/2012 | Kauphusman et al. |
| 2012/0130218 A1 | 5/2012 | Kauphusman et al. |
| 2012/0172859 A1 | 7/2012 | Condie et al. |
| 2012/0239031 A1 | 9/2012 | Pappone et al. |
| 2012/0265130 A1 | 10/2012 | De La Rama et al. |
| 2012/0271138 A1 | 10/2012 | Kordis et al. |
| 2012/0296232 A1 | 11/2012 | Ng |
| 2013/0030426 A1 | 1/2013 | Gallardo et al. |
| 2013/0085479 A1 | 4/2013 | De La Rama et al. |
| 2013/0090651 A1 | 4/2013 | Smith |
| 2013/0172872 A1 | 7/2013 | Subramaniam |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0226167 A1 | 8/2013 | Kaplan et al. |
| 2013/0253504 A1 | 9/2013 | Fang |
| 2013/0274582 A1 | 10/2013 | Afonso et al. |
| 2013/0296852 A1 | 11/2013 | Madjarov et al. |
| 2013/0310825 A1 | 11/2013 | Pappone et al. |
| 2013/0338467 A1 | 12/2013 | Grasse et al. |
| 2014/0018788 A1 | 1/2014 | Engelman et al. |
| 2014/0025063 A1 | 1/2014 | Kaplan et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0194716 A1 | 7/2014 | Diep et al. |
| 2014/0200639 A1 | 7/2014 | De La Rama |
| 2014/0207136 A1 | 7/2014 | De La Rama et al. |
| 2014/0257069 A1 | 9/2014 | Eliason et al. |
| 2014/0276712 A1 | 9/2014 | Mallin et al. |
| 2014/0296902 A1 | 10/2014 | Huszar et al. |
| 2014/0303619 A1 | 10/2014 | Pappone et al. |
| 2014/0309512 A1 | 10/2014 | Govari et al. |
| 2014/0316294 A1 | 10/2014 | Maskara et al. |
| 2014/0316496 A1 | 10/2014 | Masson et al. |
| 2014/0330269 A1 | 11/2014 | Pappone et al. |
| 2014/0343546 A1 | 11/2014 | De La Rama et al. |
| 2015/0011991 A1 | 1/2015 | Buysman et al. |
| 2015/0045863 A1 | 2/2015 | Litscher et al. |
| 2015/0105645 A1 | 4/2015 | Subramaniam et al. |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0209547 A1 | 7/2015 | De La Rama et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2015/0351652 A1 | 12/2015 | Marecki et al. |
| 2015/0374252 A1 | 12/2015 | De La Rama et al. |
| 2016/0073913 A1 | 3/2016 | Francis et al. |
| 2016/0081746 A1 | 3/2016 | Solis |
| 2016/0113709 A1 | 4/2016 | Maor |
| 2016/0143588 A1 | 5/2016 | Hoitink et al. |
| 2016/0183877 A1 | 6/2016 | Williams et al. |
| 2016/0213916 A1 | 7/2016 | De La Rama |
| 2016/0228023 A1 | 8/2016 | Govari |
| 2016/0228062 A1 | 8/2016 | Altmann et al. |
| 2016/0242667 A1 | 8/2016 | Fay et al. |
| 2016/0278853 A1 | 9/2016 | Ogle et al. |
| 2016/0302858 A1 | 10/2016 | Bencini |
| 2016/0317093 A1 | 11/2016 | Berenfeld et al. |
| 2016/0338770 A1 | 11/2016 | Bar-Tal et al. |
| 2016/0346038 A1 | 12/2016 | Helgeson et al. |
| 2016/0374753 A1* | 12/2016 | Wu et al. |
| 2017/0000365 A1 | 1/2017 | Wu et al. |
| 2017/0007158 A1 | 1/2017 | Gross et al. |
| 2017/0027638 A1 | 2/2017 | Solis |
| 2017/0035497 A1 | 2/2017 | Nagale et al. |
| 2017/0042449 A1* | 2/2017 | Deno et al. |
| 2017/0049348 A1 | 2/2017 | Deno et al. |
| 2017/0049349 A1 | 2/2017 | Sallee et al. |
| 2017/0056105 A1 | 3/2017 | Steinke et al. |
| 2017/0065227 A1 | 3/2017 | Marrs et al. |
| 2017/0065341 A1 | 3/2017 | Pappone et al. |
| 2017/0071494 A1 | 3/2017 | Solis et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0105796 A1 | 4/2017 | Pappone et al. |
| 2017/0112404 A1 | 4/2017 | De La Rama et al. |
| 2017/0112405 A1 | 4/2017 | Sterrett et al. |
| 2017/0143227 A1 | 5/2017 | Marecki et al. |
| 2017/0156790 A1 | 6/2017 | Aujla |
| 2017/0165000 A1 | 6/2017 | Basu et al. |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0251978 A1 | 9/2017 | Rodrigo Bort et al. |
| 2017/0265812 A1 | 9/2017 | Williams et al. |
| 2017/0273738 A1 | 9/2017 | Wu |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0319269 A1 | 11/2017 | Oliverius et al. |
| 2017/0332970 A1 | 11/2017 | Aujla |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2017/0354797 A1 | 12/2017 | De La Rama et al. |
| 2017/0367756 A1 | 12/2017 | Sliwa et al. |
| 2018/0008203 A1 | 1/2018 | Iyun et al. |
| 2018/0028084 A1 | 2/2018 | Williams et al. |
| 2018/0042667 A1 | 2/2018 | Pappone et al. |
| 2018/0049803 A1 | 2/2018 | Solis |
| 2018/0050190 A1 | 2/2018 | Masson |
| 2018/0055563 A1 | 3/2018 | Shetake et al. |
| 2018/0056038 A1 | 3/2018 | Aujla |
| 2018/0070845 A1 | 3/2018 | Hoitink et al. |
| 2018/0071017 A1 | 3/2018 | Bar-Tal et al. |
| 2018/0085064 A1 | 3/2018 | Auerbach et al. |
| 2018/0116539 A1* | 5/2018 | Olson et al. |
| 2018/0132749 A1 | 5/2018 | Govari et al. |
| 2018/0137687 A1 | 5/2018 | Katz et al. |
| 2018/0160978 A1 | 6/2018 | Cohen et al. |
| 2018/0161577 A1 | 6/2018 | Goedeke et al. |
| 2018/0168511 A1 | 6/2018 | Hall et al. |
| 2018/0185651 A1 | 7/2018 | Astrom et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |

(56) References Cited

U.S. PATENT DOCUMENTS

| | | |
|---|---|---|
| 2018/0303361 A1 | 10/2018 | Wu et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0099585 A1 | 4/2019 | De La Rama et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0192221 A1 | 6/2019 | Pappone |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0275291 A2 | 9/2019 | de la Rama et al. |
| 2019/0282116 A1 | 9/2019 | Olson |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2019/0350649 A1 | 11/2019 | Sutermeister et al. |
| 2020/0000518 A1 | 1/2020 | Kiernan et al. |
| 2020/0008705 A1 | 1/2020 | Ziv-Ari et al. |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0038101 A1 | 2/2020 | Tobey et al. |
| 2020/0038103 A1 | 2/2020 | Pappone et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0138378 A1 | 5/2020 | De La Rama et al. |
| 2020/0163707 A1 | 5/2020 | Sliwa et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206456 A1 | 7/2020 | De La Rama et al. |
| 2020/0206498 A1 | 7/2020 | Arora et al. |
| 2020/0253497 A1 | 8/2020 | Sterrett et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0297996 A1 | 9/2020 | De La Rama et al. |
| 2020/0305726 A1 | 10/2020 | Salvestro et al. |
| 2020/0305946 A1 | 10/2020 | Desimone et al. |
| 2020/0330752 A1 | 10/2020 | De La Rama et al. |
| 2020/0345262 A1 | 11/2020 | Selkee et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0015551 A1 | 1/2021 | Fuentes-Ortega et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059745 A1 | 3/2021 | Highsmith et al. |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |
| 2021/0369339 A1 | 12/2021 | Salazar et al. |
| 2022/0054192 A1 | 2/2022 | Beeckler et al. |
| 2022/0054198 A1 | 2/2022 | Tegg et al. |
| 2023/0190166 A1 | 6/2023 | Spector |

FOREIGN PATENT DOCUMENTS

| | | |
|---|---|---|
| CN | 103220994 A | 7/2013 |
| CN | 103298392 A | 9/2013 |
| CN | 103315806 A | 9/2013 |
| CN | 102892453 B | 4/2015 |
| CN | 104968261 A | 10/2015 |
| CN | 102665586 B | 3/2016 |
| CN | 105534518 A | 5/2016 |
| CN | 105615994 A | 6/2016 |
| CN | 103298392 B | 8/2016 |
| CN | 104968261 B | 5/2019 |
| CN | 110786926 A | 2/2020 |
| CN | 111096788 A | 5/2020 |
| CN | 111248993 A | 6/2020 |
| CN | 111248996 A | 6/2020 |
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2166936 A1 | 3/2010 |
| EP | 2173426 A1 | 4/2010 |
| EP | 2166936 A4 | 7/2010 |
| EP | 2173426 A4 | 7/2010 |
| EP | 2429436 A1 | 3/2012 |

(56) References Cited

FOREIGN PATENT DOCUMENTS

| | | |
|---|---|---|
| EP | 2470101 A1 | 7/2012 |
| EP | 2544749 A1 | 1/2013 |
| EP | 2568906 A1 | 3/2013 |
| EP | 2470101 A4 | 6/2013 |
| EP | 2613686 A1 | 7/2013 |
| EP | 2613723 A1 | 7/2013 |
| EP | 2544749 A4 | 10/2013 |
| EP | 2568906 A4 | 5/2014 |
| EP | 2613686 A4 | 7/2014 |
| EP | 2783651 A1 | 10/2014 |
| EP | 2613723 A4 | 4/2015 |
| EP | 2544749 B1 | 8/2015 |
| EP | 2907462 A1 | 8/2015 |
| EP | 2908723 A1 | 8/2015 |
| EP | 2699151 B1 | 11/2015 |
| EP | 2699152 B1 | 11/2015 |
| EP | 1 585 446 B1 | 12/2015 |
| EP | 2699153 B1 | 12/2015 |
| EP | 2977020 A1 | 1/2016 |
| EP | 2173426 B1 | 4/2016 |
| EP | 2498706 B1 | 4/2016 |
| EP | 3023052 A1 | 5/2016 |
| EP | 2429436 B1 | 11/2016 |
| EP | 3 111 872 A1 | 1/2017 |
| EP | 3146926 A1 | 3/2017 |
| EP | 2578173 B1 | 6/2017 |
| EP | 3184037 A1 | 6/2017 |
| EP | 2568906 B1 | 8/2017 |
| EP | 2613723 B1 | 10/2017 |
| EP | 2977020 B1 | 11/2017 |
| EP | 3238645 A1 | 11/2017 |
| EP | 2884931 B1 | 1/2018 |
| EP | 3111872 B1 | 4/2018 |
| EP | 3300681 A1 | 4/2018 |
| EP | 2613686 B1 | 9/2018 |
| EP | 3 527 125 A1 | 8/2019 |
| EP | 2349440 B1 | 8/2019 |
| EP | 3300681 B1 | 11/2019 |
| EP | 3318211 B1 | 12/2019 |
| EP | 3581135 A1 | 12/2019 |
| EP | 2736434 B1 | 2/2020 |
| EP | 2908723 B1 | 3/2020 |
| EP | 3451962 B1 | 3/2020 |
| EP | 2470101 B1 | 5/2020 |
| EP | 3679861 A1 | 7/2020 |
| EP | 3 733 103 A1 | 11/2020 |
| EP | 3738508 A1 | 11/2020 |
| EP | 3738509 A1 | 11/2020 |
| EP | 3915477 A1 | 12/2021 |
| EP | 3972510 A1 | 3/2022 |
| JP | 2012525933 A | 10/2012 |
| JP | 2013516218 A | 5/2013 |
| JP | 2013521892 A | 6/2013 |
| JP | 2014501557 A | 1/2014 |
| JP | 2014502195 A | 1/2014 |
| JP | 2014512227 A | 5/2014 |
| JP | 5539498 B2 | 7/2014 |
| JP | 2014158957 A | 9/2014 |
| JP | 5753862 B2 | 7/2015 |
| JP | 5778823 B2 | 9/2015 |
| JP | 2015211874 A | 11/2015 |
| JP | 2016502912 A | 2/2016 |
| JP | 2016104129 A | 6/2016 |
| JP | 6050522 B2 | 12/2016 |
| JP | 6059535 B2 | 1/2017 |
| JP | 6078471 B2 | 2/2017 |
| JP | 2017077479 A | 4/2017 |
| JP | 2017176879 A | 10/2017 |
| JP | 2018503435 A | 2/2018 |
| JP | 6445509 B2 | 12/2018 |
| JP | 2019030685 A | 2/2019 |
| JP | 2020018857 A | 2/2020 |
| JP | 2020065933 A | 4/2020 |
| JP | 2021526401 A | 10/2021 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 A2 | 11/2001 |
| WO | 2004087249 A2 | 10/2004 |
| WO | 2008124602 A1 | 10/2008 |
| WO | 2008124619 A1 | 10/2008 |
| WO | 2009006616 A1 | 1/2009 |
| WO | 2009023385 A1 | 2/2009 |
| WO | 2010129661 A1 | 11/2010 |
| WO | 2011081686 A1 | 7/2011 |
| WO | 2011112814 A1 | 9/2011 |
| WO | 2011159861 A2 | 12/2011 |
| WO | 2011159955 A1 | 12/2011 |
| WO | 2011159861 A3 | 2/2012 |
| WO | 2012068505 A1 | 5/2012 |
| WO | 2012071087 A1 | 5/2012 |
| WO | 2012100185 A2 | 7/2012 |
| WO | 2012068505 A9 | 10/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014113612 A1 | 7/2014 |
| WO | 2014176205 A1 | 10/2014 |
| WO | 2015095577 A1 | 6/2015 |
| WO | 2015130824 A1 | 9/2015 |
| WO | 2016001015 A1 | 1/2016 |
| WO | 2016019760 A1 | 2/2016 |
| WO | 2016044687 A1 | 3/2016 |
| WO | 2017192712 A1 | 11/2017 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2019177809 A1 | 9/2019 |
| WO | 2020026217 A1 | 2/2020 |
| WO | 2020206328 A1 | 10/2020 |

OTHER PUBLICATIONS

Extended European Search Report dated Mar. 18, 2021, from corresponding EP Application No. 20199230.2.
Extended European Search Report dated Mar. 18, 2021, from corresponding EP Application No. 20199175.9.
Extended European Search Report for European Application No. 20172013.3, mailed Sep. 21, 2020, 8 Pages.
Extended European Search Report for European Application No. 22194801.1, mailed Dec. 23, 2022, 9 pages.
Extended European Search Report dated May 11, 2023, from corresponding EP Application No. 23163381.9.
Extended European Search Reported dated Feb. 27, 2023, from corresponding European Patent Application No. 22194803.7.
Examination Report dated Sep. 6, 2023, from corresponding EP Application No. 20172013.3.
Search Report dated Nov. 29, 2023, from corresponding Japanese Application No. 2020-078996.
Notice of Reasons for Refusal dated Dec. 5, 2023, from corresponding Japanese Application No. 2020-078996.
Written Opinion dated Mar. 5, 2024, from corresponding Japanese Application No. 2020-078996.
Notice of Reasons for Refusal dated May 14, 2024, from corresponding Japanese Application No. 2020-078996.
Written Opinion dated Jul. 23, 2024, from corresponding Japanese Application No. 2020-078996.
Decision to Grant a Patent dated Aug. 6, 2024, from corresponding Japanese Application No. 2020-078996.
Extended European Search Report dated Feb. 27, 2023, from corresponding European Application No. 22194803.7.
Search Report dated Feb. 22, 2024, from corresponding Japanese Application No. 2020-164914.
Notice of Reasons for Refusal dated Feb. 27, 2024, from corresponding Japanese Application No. 2020-164914.
Written Opinion dated May 15, 2024, from corresponding Japanese Application No. 2020-164914.

(56) References Cited

OTHER PUBLICATIONS

Decision to Grant a Patent dated May 28, 2024, from corresponding Japanese Application No. 2020-164914.
Extended European Search Report dated Jul. 18, 2023, from corresponding European Application No. 22207377.7.
Extended European Search Report dated Aug. 14, 2023, from corresponding European Application No. 23168941.5.
Extended European Search Report dated Oct. 23, 2023, from corresponding European Application No. 23175980.4.
Extended European Search Report dated Jul. 4, 2024, from corresponding European Application No. 23220720.9.
Extended European Search Report dated Jun. 5, 2024, from corresponding European Application No. 23220734.0.
First Office Action and Search Report with English translation dated Sep. 30, 2024, from corresponding Chinese Application No. 202011055244.1.

* cited by examiner

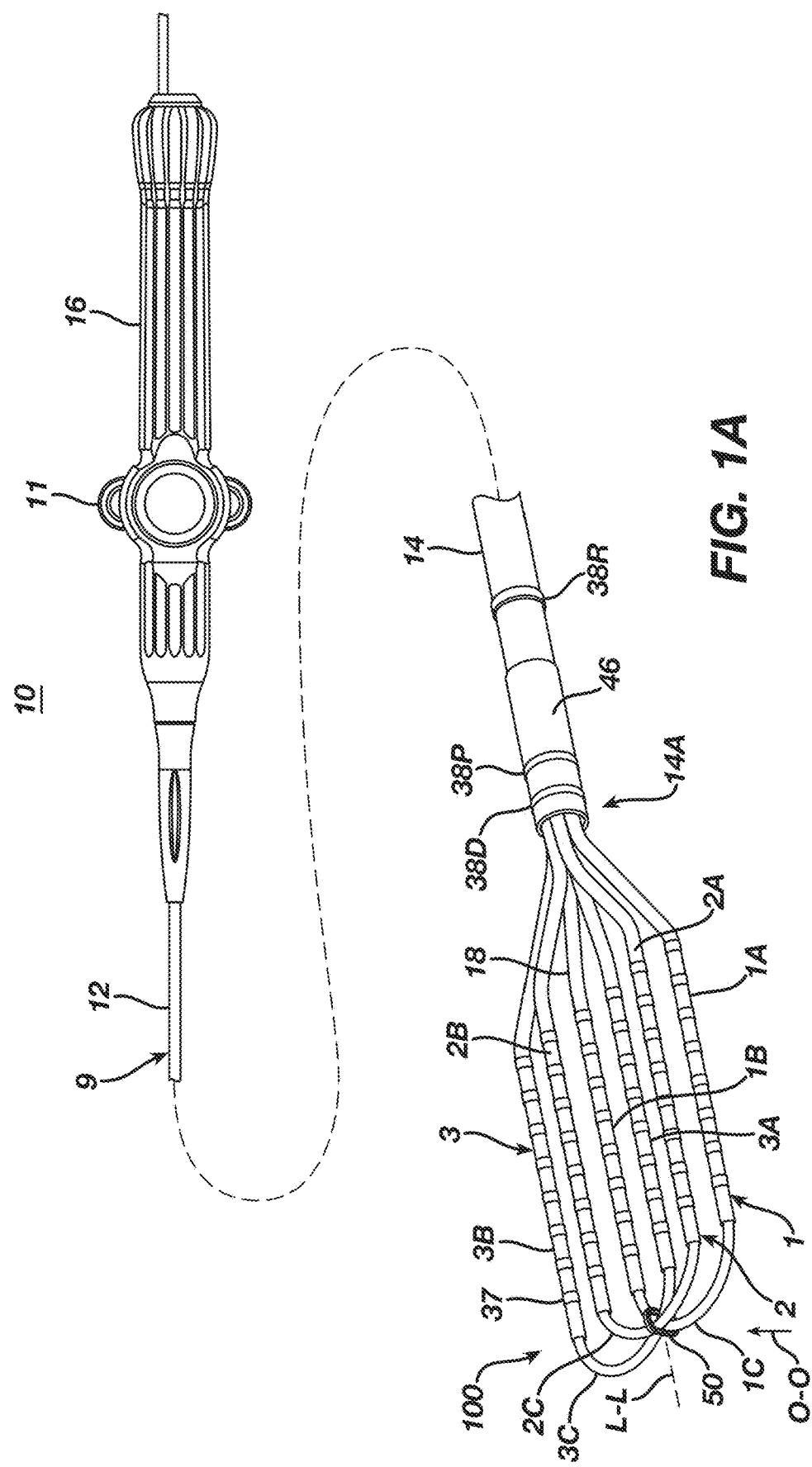

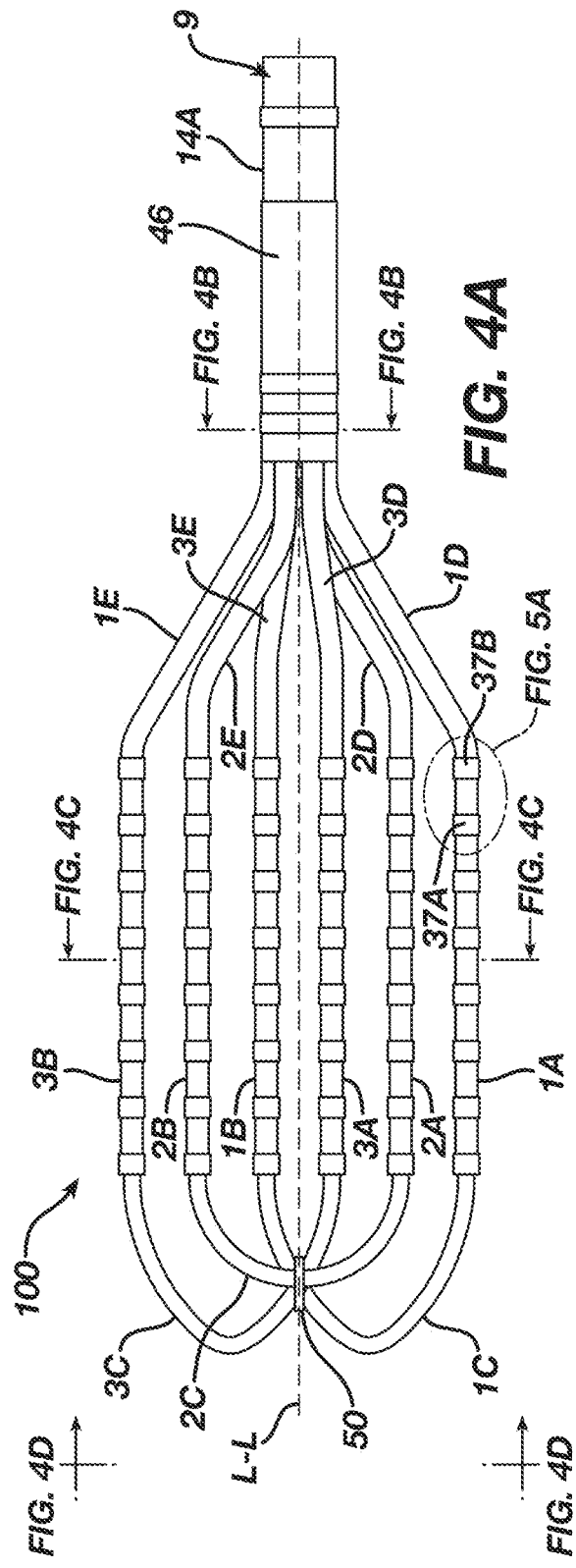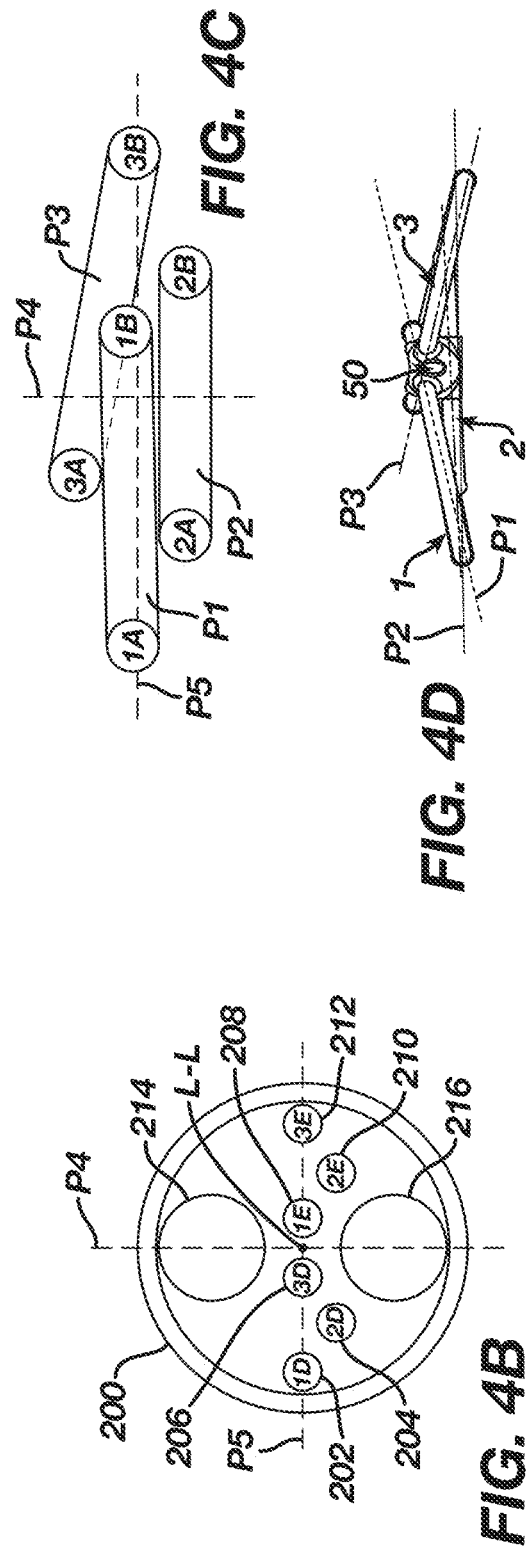

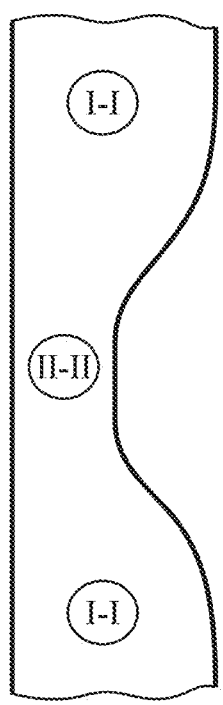 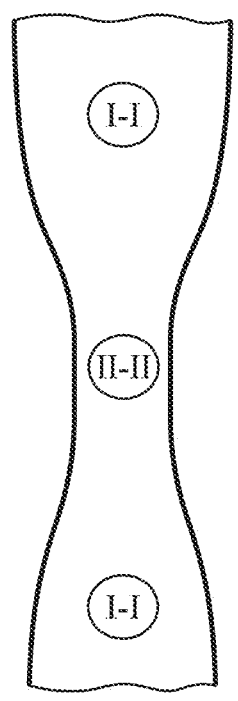
FIG. 10F  FIG. 10G

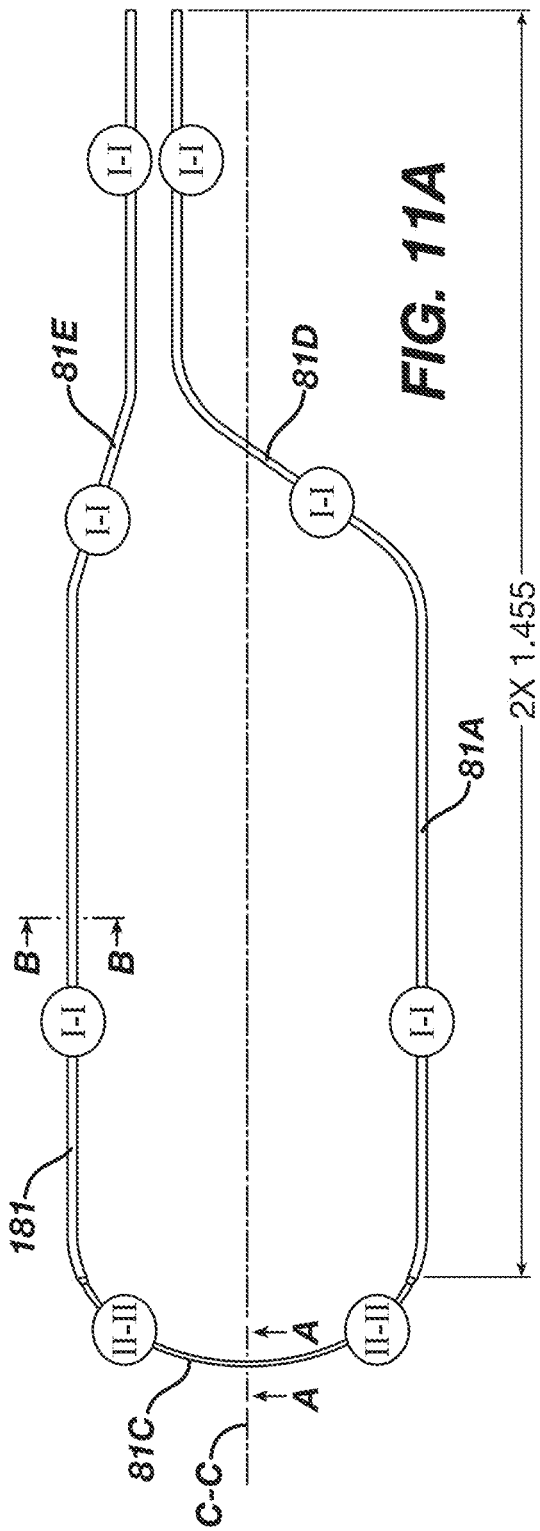
FIG. 11A
FIG. 11C
FIG. 11B

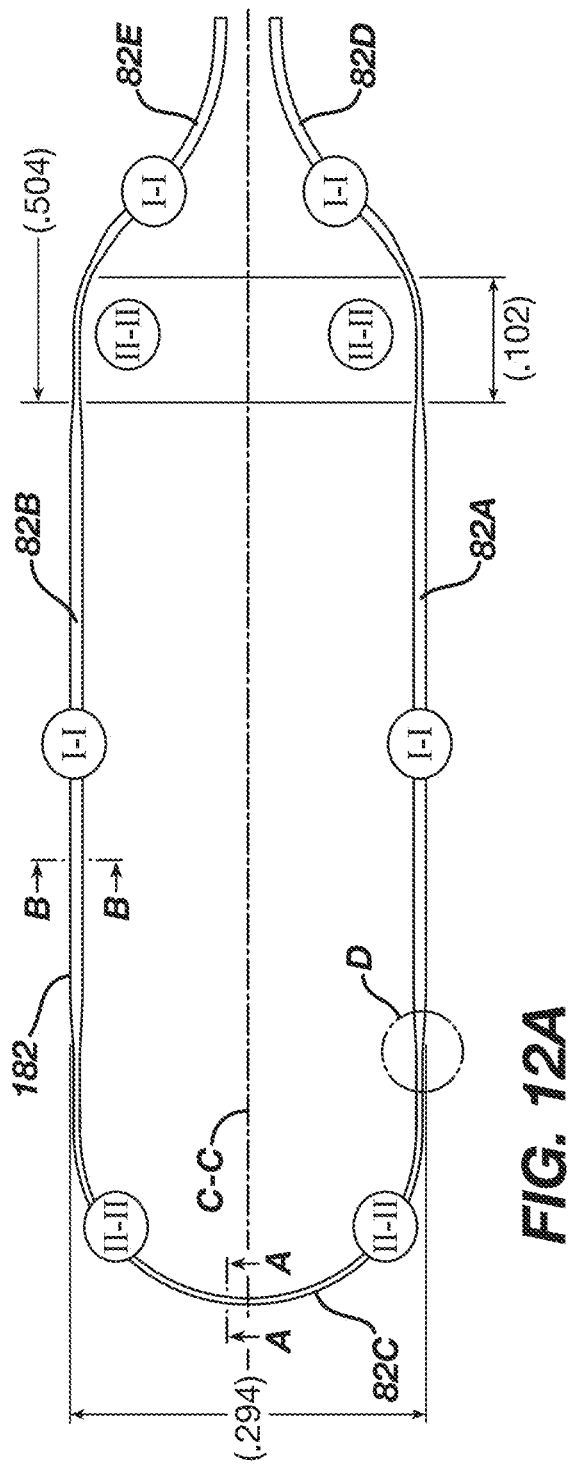
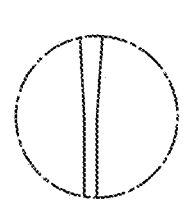
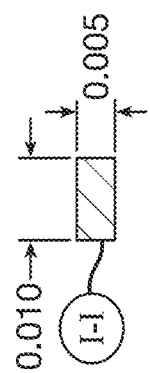
FIG. 12A
FIG. 12B
FIG. 12C
FIG. 12D

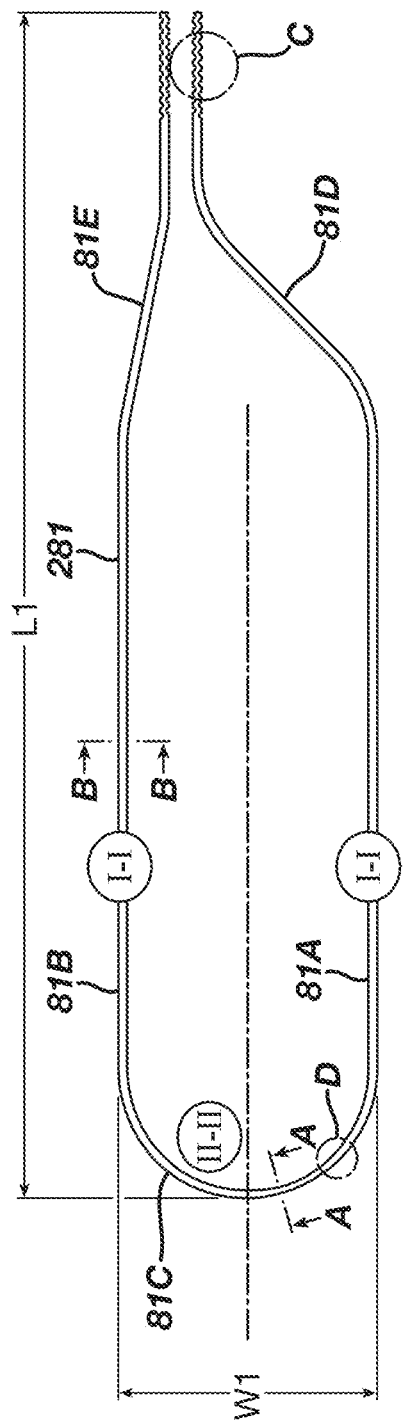
FIG. 13A
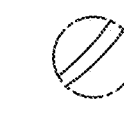
FIG. 13B
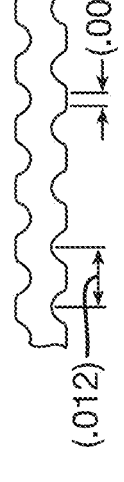
FIG. 13C
FIG. 13D
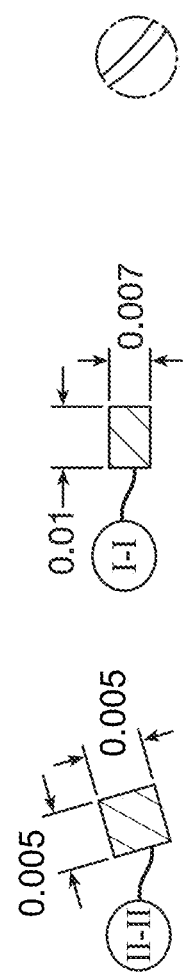
FIG. 13E

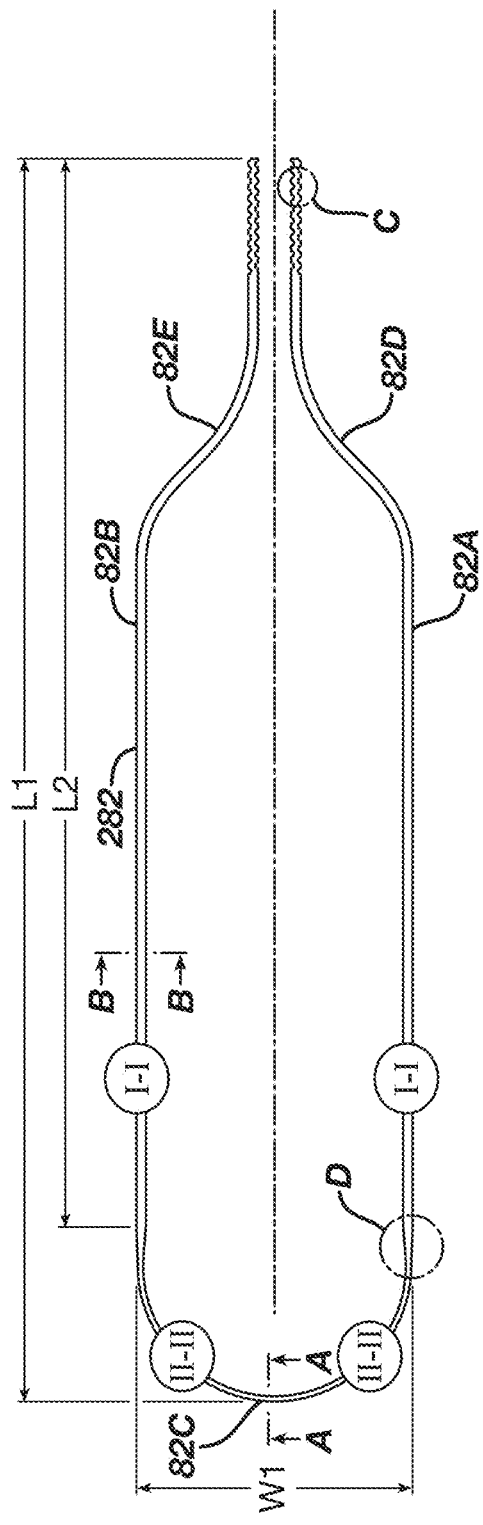
FIG. 14A
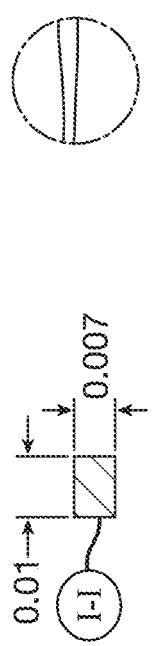
FIG. 14B
FIG. 14C
FIG. 14D
FIG. 14E

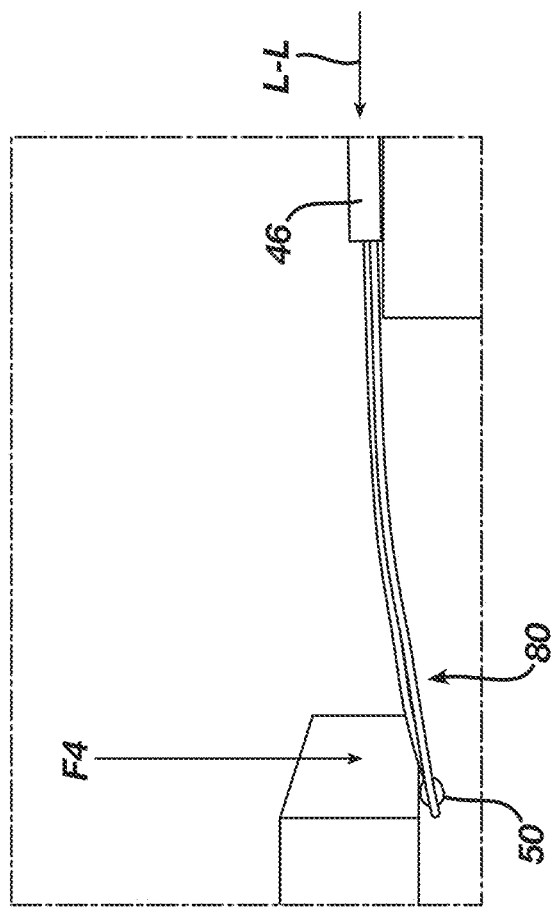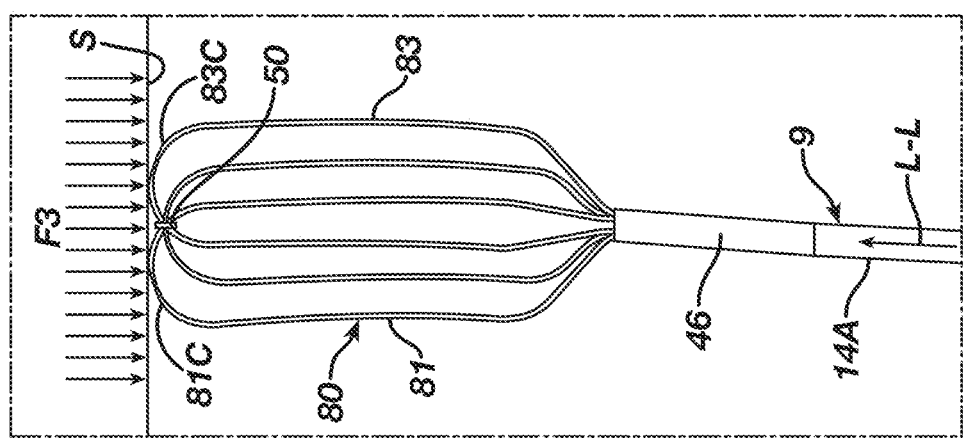

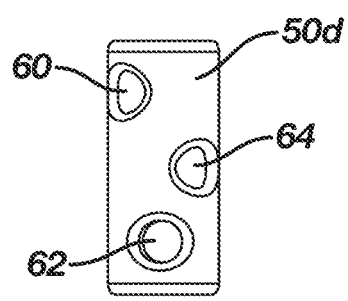
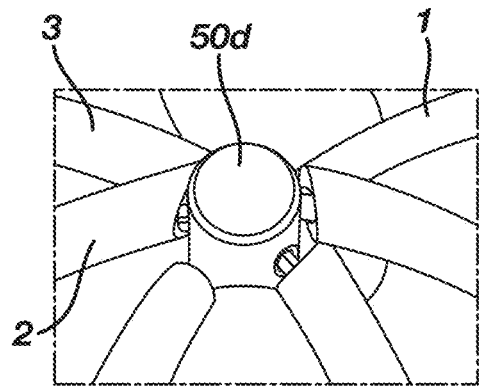
FIG. 20A  FIG. 20B
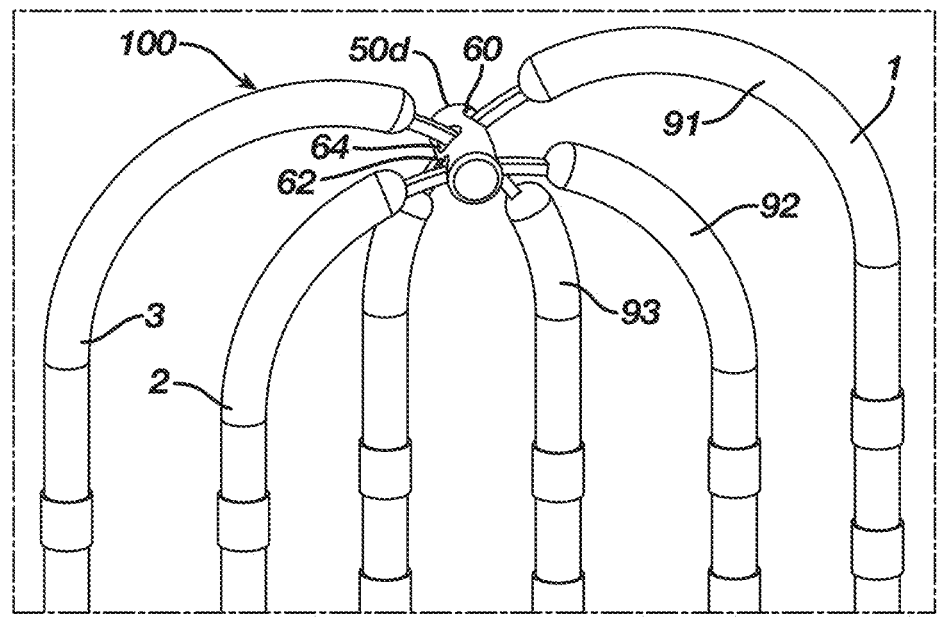
FIG. 20C

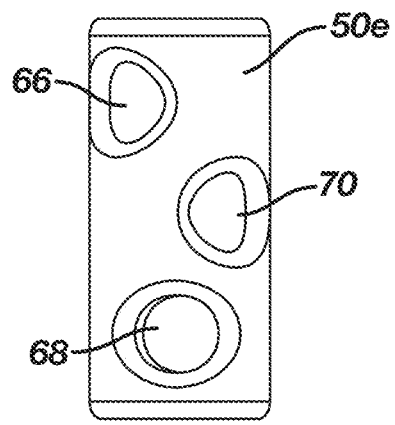
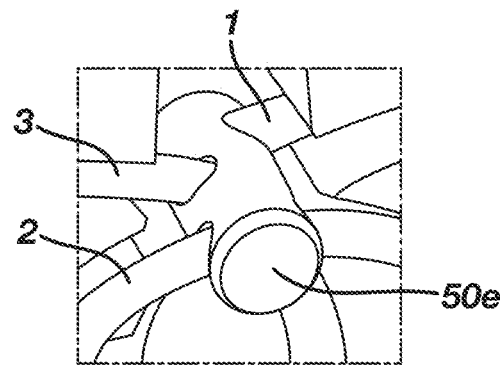
FIG. 21A  FIG. 21B
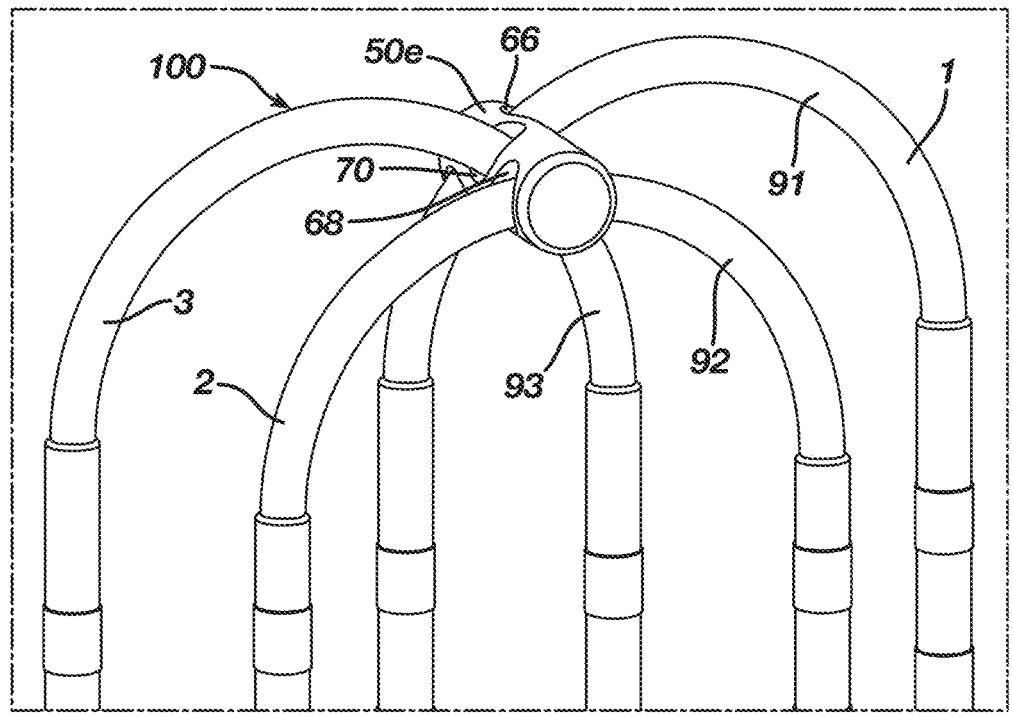
FIG. 21C

Ra = 0.1-0.2 μm

Ra = 0.3-0.4 μm

ELECTRODE APPARATUS FOR DIAGNOSIS OF ARRHYTHMIAS

CROSS REFERENCE TO RELATED APPLICATIONS

This application claims the benefits of priority under the Paris Convention as well as 35 USC §§ 119 and 120 to prior filed U.S. Provisional Patent Application Ser. 63/031,955, titled as "ELECTRODE APPARATUS FOR DIAGNOSIS OF ARRHYTHMIAS" and filed on May 29, 2020 and U.S. Provisional Patent Application Ser. 63/052,553 titled as "INTRALUMINAL REFERENCE ELECTRODE FOR CARDIOVASCULAR TREATMENT APPARATUS" filed on Jul. 16, 2020, which priority applications are hereby incorporated by reference as set forth in full herein.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Sources of undesired signals can be located in tissue of an atria or a ventricle. Unwanted signals are conducted elsewhere through heart tissue where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is possible to cease or modify the propagation of unwanted electrical signals from one portion of the heart to another. The ablation process destroys the unwanted electrical pathways by formation of non-conducting lesions.

In this two-step procedure, which includes mapping followed by ablation, electrical activity at points in the heart is typically sensed and measured by advancing a catheter containing one or more electrical sensors into the heart and acquiring data at multiple points. These data are then utilized to select the target areas at which ablation is to be performed.

For greater mapping resolution, it is desirable for a mapping catheter to provide high-density signal maps through the use of several electrodes sensing electrical activity of tissue in an area on the order of a square centimeter. For mapping within an atria or a ventricle (for example, an apex of a ventricle), it is desirable for a catheter to collect larger amounts of data signals within shorter time spans. It is also desirable for such a catheter to be adaptable to different tissue surfaces, for example, flat, curved, irregular or nonplanar surface tissue and be collapsible for atraumatic advancement and withdrawal through a patient's vasculature.

SUMMARY

Example apparatuses disclosed herein are generally usable with catheter-based systems to measure or provide electrical signals within the heart and surrounding vasculature. Example apparatuses generally include an end effector having loop members with electrodes thereon. The end effector can include features which provide improved and/or alternative diagnostic or treatment options compared to existing end effectors. Such features can include three loop members that are non-coplanar when expanded unconstrained that become contiguous to a planar surface when the spines are deflected against the surface, a mechanical linkage that joins three loop members of the end effector, electrodes having surface treatment to enhance surface roughness of the electrodes, twisted pair electrode wires, a bonded spine cover, and/or any combination thereof.

An example apparatus includes an elongated shaft and an end effector. The elongated shaft has a proximal portion and a distal portion and is configured to be manipulated at the proximal portion to position the distal portion into the heart of a patient. The elongated shaft defines a longitudinal axis of the apparatus. The end effector is disposed near the distal portion of the elongated shaft. The end effector includes three loop members overlapping at a common distal vertex along the longitudinal axis. Each of the three loop members includes a respective pair of ends affixed to the distal portion of the elongated shaft.

The end effector can be configured to expand to an unconstrained configuration when unconstrained to define three different planes for the respective three loop members. When the distal portion of the elongated shaft is deflected at an angle relative to the longitudinal axis, a majority of a length of each of the loop members becomes contiguous to a planar surface, thereby moving the end effector into in a flattened configuration. The three loop members are thereby movable to a flattened configuration when the loop members are positioned against a planar surface.

The majority of the length each of the loop members can be non-coplanar with the majority of the length of at least one of the other loop members when the end effector is in the unconstrained configuration.

Each of the loop members respectively can include a support frame extending through a respective loop member. Each support frame can be affixed to the distal portion of the elongated shaft where each end of the respective pair of ends of the respective loop member is affixed to the distal portion of the elongates shaft. Each of the respective support frames can define a respective looped path of its respective loop member when the end effector is in the unconstrained configuration. Each of the respective support frames can include a respective cross sectional shape orthogonal to the respective looped path, each of the respective cross sectional shapes varying along the respective looped path.

Each of the respective support frames can include a serrated edge engaged to the distal portion of the elongated shaft.

Each of the respective support frames can include a respective pair of parallel segments. When the end effector is in the flattened configuration, a majority of the length of each segment of the pairs of parallel segments can be coplanar with each other. When the end effector is in the unconstrained configuration, the majority of the length of at least one segment of the pairs of parallel segments can be non-coplanar with the majority of the respective length of at least one of the other segments of the pairs of parallel segments.

Each of the support frames can include a respective connecting segment extending between the respective pair of parallel segments and overlapping at the distal vertex with the respective connecting segment of each of the other respective support frames.

The apparatus can further include a mechanical linkage binding the three loop members at the common distal vertex. The mechanical linkage can include a rectangular or ovular shape having an opening through which the three loop members extend and a side comprising a seam. Alternatively, the mechanical linkage can include four contiguous sides, i.e. lacking a seam. Alternatively, the mechanical linkage can include three openings through which a respective loop member extends. At least one of the three openings can have a substantially circular shape while at least one other of the three openings has an oblong shape.

As an alternative to having a rectangular or ovular shape, the mechanical linkage can have a cylindrical shape with three passageways therethrough. The three passageways can each have a respective loop member of the three loop members extending therethrough. Some or all of the three loop members can include a respective tubular housing surrounding the respective support frame that also extends through the respective passageway. Some or all of the looped members can lack an outer housing where they extend through the respective passageway (e.g. support members can be bare at the distal vertex. Some or all of the support members which are bare where they pass through the respective passageway can have a respective tubular housing surrounding the respective support frame elsewhere along the looped path.

As an alternative to having a rectangular, ovular, or cylindrical shape, the mechanical linkage can be shaped in the form of a tapered ring having an annular opening through which the three loop members extend and a tapered height extending across a diameter of annular opening.

The apparatus can further include multiple electrodes affixed to the three loop members. Each electrode can have a surface characterized by roughness parameter Ra representing an arithmetical mean deviation of a profile of the surface, where Ra measures from about 0.3 micrometers to about 0.4 micrometers.

The apparatus can further include wires connected to electrodes carried by the loop members. The wires can be bundled together within the loop members. The apparatus can further include wire pairs twisted about each other within the end effector. Each wire pair can be electrically connected to a respective pair of electrodes.

As a first possible loop member housing configuration, the three loop members can each respectively include an inner tube housing, an outer tubular housing, and electrical conductors. The inner tubular housing can surround at least a portion of the respective support frame. The outer tubular housing can surround at least a portion of the inner tubular housing and can be bonded to the inner tubular housing. The electrical conductors can be disposed at least partially within the outer tubular housing and outside of the inner tubular housing. Each of the three loop members can further respectively include an irrigation tube positioned within the outer tubular housing and outside of the inner tubular housing.

As a second possible loop member housing configuration, alternative to the first possible configuration, the three loop members can each respectively include a tubular housing, electrical conductors, and an irrigation tube. Each respective tubular housing can surround the respective support frame and include at least two lumens therethrough such that the respective support frame extends through a first lumen of the two lumens. The electrical conductors can be disposed in a second lumen of the at least two lumens separate from the first lumen. The irrigation tube can also be disposed in the second lumen.

As a third possible loop member housing configuration, alternative to the first and second possible configurations, the three loop members can each respectively include a tubular housing, electrical conductors, and an irrigation lumen. Each tubular housing can surround the respective support frame and include at least three lumens therethrough. The respective support frame can extend through a first lumen of the at least three lumens. The electrical conductors can be disposed in a second lumen of the at least three lumens separate from the first lumen. The third lumen of the at least three lumens separate from the first and second lumens can be configured for irrigation. The third lumen can be configured to irrigate direction and/or can include an irrigation tube.

The first, second, and third loop member configurations are combinable such that one loop member in the apparatus can have one of the first, second, and third possible loop member housing configurations and another loop member of the apparatus can have a different configuration.

The apparatus can further include at least one pull wire extending through the elongated shaft and attached to the distal portion of the elongated shaft so that when the pull wire is retracted toward the proximal portion relative to the elongated shaft, the distal portion and the end effector are bent at an angle with respect to the longitudinal axis.

An example method can include one or more of the following steps presented in no particular order. A first loop member, a second loop member, and a third loop member can each respectively be shaped to each form a respective loop. A respective pair of ends of each of the first loop member, the second loop member, and the third loop member can be coupled to a distal portion of an elongated shaft. The first loop member, the second loop member, and the third loop member can be overlapped at a common distal vertex distal to the distal portion of the elongated shaft such that when the first, second, and third loop members are unconstrained, a majority of the first loop member is non-coplanar with a majority of at least one of the second loop member and the third loop member. The majority of the first loop member, the majority of the second loop member, and the majority of the third loop member can be pressed in contact with a planar surface via manipulation of the elongated shaft. The first, second and third loop members can be placed into contact with a planar surface to align the majority of the first loop member, the majority of the second loop member, and the majority of the third loop member with the planar surface.

The method can further include positioning the first loop member, second loop member, third loop member, and distal portion of the elongated shaft within an intravascular catheter (or guiding sheath) while a proximal portion of the elongated shaft extends proximally from the intravascular catheter.

The method can further include moving the first loop member, second loop member, and third loop member out of a distal end of the catheter via manipulation of the proximal portion of the elongated shaft.

The method can further include pressing the majority of the first loop member, the majority of the second loop member, and the majority of the third loop member in contact with the planar surface via manipulation of the proximal portion of the elongated shaft.

The method can further include shaping a first support frame to define a first looped path such that the first support frame comprises a cross sectional shape orthogonal to the first looped path that varies along the first looped path. The method can further include positioning the first support frame in the first loop member. The method can further include shaping a second support frame to define a second looped path such that the second support frame comprises a cross sectional shape orthogonal to the second looped path that varies along the second looped path. The method can further include positioning the second support frame in the second loop member. The method can further include shaping a third support frame to define a third looped path such that the third support frame comprises a cross sectional shape orthogonal to the third looped path that varies along the third looped path. The method can further include positioning the third support frame in the third loop member.

The method can further include affixing the first, second, and third support frames to the distal portion of the elongated shaft at each end of the respective pair of ends of the first loop member, the second loop member, and the third loop member.

The method can further include engaging a serrated edge of each of the first, second, and third support frames to the distal portion of the elongated shaft.

The method can further include positioning the first support frame, the second support frame, and the third support frame such that the first looped path defines a first plane intersecting at least one of a second plane defined by the second looped path and a third plane defined by the third looped path.

The method can further include shaping a first pair of parallel segments in the first support frame, a second pair of parallel segments in the second support frame, and a third pair of parallel segments in the third support frame. The method can further include moving a majority of a length of each segment of the first pair of parallel segments, the second pair of parallel segments, and the third pair of parallel segments into alignment parallel to the planar surface via manipulation of the elongated shaft.

The method can further include shaping a first connecting segment extending between the first pair of parallel segments, a second connecting segment extending between the second pair of parallel segments, and a third connecting segment extending between the third pair of parallel segments.

The method can further include mechanically binding the three loop members at the distal vertex.

The method can further include forming a clip having two ends and a partially wrapped shape having an opening sized to receive the first, second, and third loop members. The method can further include moving the first, second, and third loop members through the opening into the partially wrapped shape. The method can further include moving the two ends of the clip to collapse the opening. The method can further include confining the first, second, the third loop members at the distal vertex with the clip.

As an alternative to confining the first, second, and third loop members with the clip, the method can include confining the first, second, the third loop members at the distal vertex within an opening of an alternative mechanical linkage having a contiguous perimeter.

As another alternative, the method can include forming another alternative mechanical linkage having a rectangular or ovular shape having a first opening, a second opening, and a third opening. The method can further include positioning the first loop member in the first opening, the second loop member in the second opening, and the third loop member in the third opening. The method can further include linking the first, second, and third loop members at the distal vertex with the mechanical linkage. The method can further include forming the first opening to have a substantially circular shape. The method can further include forming at least one of the second opening and the third opening to have an oblong shape.

As another alternative, the method can include forming another alternative mechanical linkage having a cylindrical shape with a first passageway therethrough, a second passageway therethrough, and a third passageway therethrough.

The method can further include positioning the first loop member in the first passageway, the second loop member in the second passageway, and the third loop member in the third passageway. The method can further include linking the first, second, and third loop members at the distal vertex with the mechanical linkage. The method can further include surrounding each of the first loop member, the second loop member, and the third loop member with a respective tubular housing. The method can further include positioning each of the respective tubular housings respectively through the first passageway, the second passageway, and the third passageway. As an alternative to positioning the respective tubular housings through the first, second, and third passageways, the method can include surrounding each of the first loop member, the second loop member, and the third loop member with a respective tubular housing excepting at least a respective portion of the first loop member, the second loop member, and the third loop member where the respective loop member extends through the respective passageway.

As another alternative to confining the first, second, and third loop members with the clip, the method can include confining the first, second, the third loop members at the distal vertex within an opening of a mechanical linkage including a tapered ring having an annular opening through which the first, second, the third loop members extend and a height tapering across a diameter of annular opening.

The method can further include affixing a plurality of electrodes to the three loop members. The method can further include abrading at least a portion of a surface of each electrode of the plurality of electrodes. The method can further include swaging each electrode of the plurality of electrodes.

The method can further include electrically connecting wires to electrodes carried by the first, second, and third loop members. The method can further include bundling the wires within the first, second, and third loop members.

The method can further include at least partially surrounding the first support frame in an inner tubular housing. The method can further include positioning a plurality of electrical conductors adjacent to the first support frame and outside of the inner tubular housing. The method can further include at least partially surrounding the inner tubular housing and the plurality of electrical conductors with an outer tubular housing. The method can further include bonding the outer tubular housing to the inner tubular housing.

As an alternative to the steps including the inner tubular housing and the outer tubular housing, the method can include positioning the first support frame within a first lumen of a tubular housing having at least two lumens therethrough. The method can further include positioning a plurality of electrical conductors within a second lumen of the tubular housing, the second lumen being separate from the first lumen. The method can further include positioning an irrigation tube in the second lumen.

As another alternative to the steps including the inner tubular housing and the outer tubular housing, the method can further include positioning the first support frame within a first lumen of a tubular housing having at least three lumens therethrough. The method can further include positioning a plurality of electrical conductors within a second lumen of the tubular housing, the second lumen being separate from the first lumen. The method can further include positioning an irrigation tube within a third lumen of the tubular housing, the third lumen being separate from the first lumen and the second lumen.

Another example method can include the following steps presented in no particular order. A distal portion of an elongated shaft and an end effector extending distally from the distal portion can be moved through a catheter (or guiding sheath) to the heart. The end effector can be moved from a distal end of the catheter via manipulation of a proximal portion of the elongated shaft. The end effector can be expanded to an unconstrained configuration distal to the distal end of the catheter such that the end effector has three loop members overlapping in three layers at a common distal vertex in the unconstrained configuration. The end effector can be pressed into cardiac tissue via manipulation of the proximal portion of the elongated shaft. A majority of each of the loop members can be conformed to the cardiac tissue as a result of pressing the end effector into cardiac tissue.

The method can further include expanding the end effector in the unconstrained configuration such that the majority of each of the three loop members are non-coplanar with at least one of the other three loop members.

The method can further include bending three support frames, each extending through a respective loop member of the three loop members and affixed to the distal portion of the elongated shaft, as a result of pressing the end effector into cardiac tissue.

The method can further include positioning the three support frames such that each respective support frame has a respective pair of parallel segments. The method can further include aligning a majority of each length of each segment of each of the respective pair of parallel segments parallel to the cardiac tissue as a result of pressing the end effector into cardiac tissue. The method can further include bending the three support frames on either side of the majority of each length of each segment of each of the respective pair of parallel segments as a result of pressing the end effector into cardiac tissue.

The method can further include bending the three support frames along thinner segments of the support frame, the thinner segments having a cross sectional area measuring less than a cross sectional area of the majority of each length of each segment of each of the respective pair of parallel segments.

The method can further include positioning the three support frames such that each respective support frame includes a respective connecting segment extending between the respective pair of parallel segments and overlapping, at the distal vertex, the respective connecting segment of each of the other respective support frames.

The method can further include maintaining the overlapping of the three loop members at the distal vertex with a mechanical linkage positioned at the distal vertex.

The method can further include receiving electrical signals having signals representing noise of less than 0.03 mV from electrodes positioned on the end effector and in contact with the cardiac tissue.

BRIEF DESCRIPTION OF THE DRAWINGS

FIG. 1A is an illustration of a catheter having an end effector at a distal portion of the catheter and a proximal handle at a proximal portion of the catheter according to aspects of the present invention.

FIGS. 4A through 4D are illustrations depicting orientation of loop members of the end effector according to aspects of the present invention.

FIGS. 10F and 10G are illustrations of possible transition schemes between regions of a support frame of the end effector according to aspects of the present invention.

FIG. 11A is an illustration of an asymmetrical support frame of the end effector according to aspects of the present invention.

FIGS. 11B and 11C are illustrations of cross sections of the asymmetrical support frame as indicated in FIG. 11A.

FIG. 12A is an illustration of a symmetrical support frame of the end effector according to aspects of the present invention.

FIGS. 12B and 12C are illustrations of cross sections of the symmetrical support frame as indicated in FIG. 12A.

FIG. 12D is an illustration of a detailed section of the symmetrical support frame as indicated in FIG. 12A.

FIG. 13A is an illustration of another asymmetrical support frame of the end effector according to aspects of the present invention.

FIGS. 13B and 13C are illustrations of cross sections of the asymmetrical support frame as indicated in FIG. 13A.

FIGS. 13D and 13E are illustrations of a detailed sections of the asymmetrical support frame as indicated in FIG. 13A.

FIG. 14A is an illustration of a symmetrical support frame of the end effector according to aspects of the present invention.

FIGS. 14B and 14C are illustrations of cross sections of the symmetrical support frame as indicated in FIG. 14A.

FIGS. 14D and 14E are illustrations of a detailed sections of the symmetrical support frame as indicated in FIG. 14A.

FIGS. 16A through 16D are illustrations of deformation of the support frames as a result of application of various forces according to aspects of the present invention.

FIGS. 20A through 20C are illustrations of an example cylindrical mechanical linkage having three passageways and used for joining support members of the loop members according to aspects of the present invention.

FIGS. 21A through 21C are illustrations of an example cylindrical mechanical linkage having three passageways and used for joining the loop members with tubular housings over the support members according to aspects of the present invention.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1B:
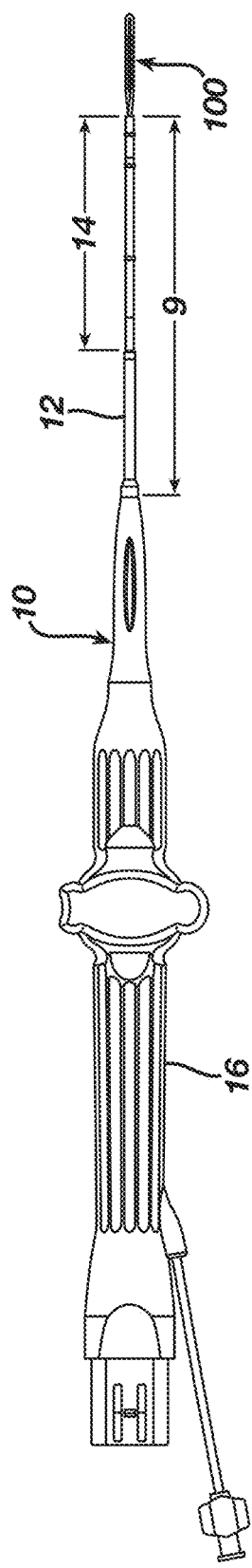
FIGS. 1B and 1C and illustrations of orthogonal side plan views of a variation of the apparatus illustrated in FIG. 1A according to aspects of the present invention.
Figure 1C:
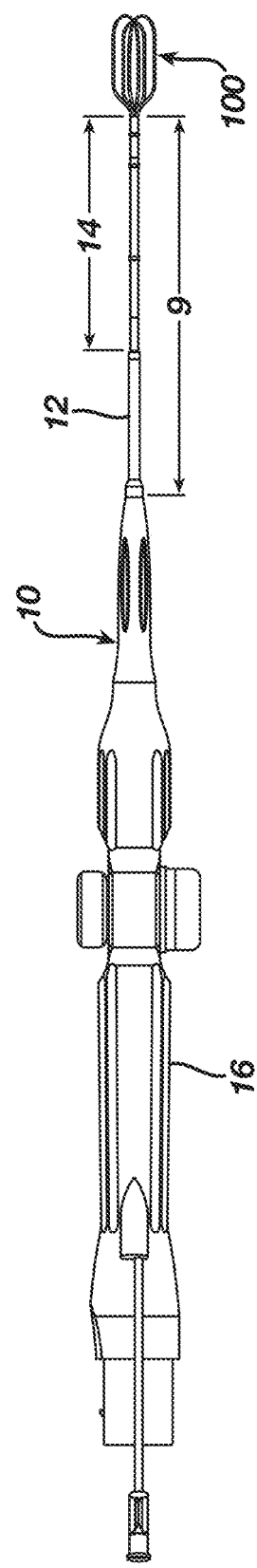

FIG. 1A illustrates an example apparatus 10 having an elongated shaft 9, a distal electrode assembly or end effector 100, and a deflection control handle 16. The shaft 9 is preferably a tubular member. FIGS. 1B and 1C and illustrations of orthogonal side plan views of a variation of the apparatus 10 illustrated in FIG. 1A. The apparatus 10 can have several design variations to while including novel aspects illustrated herein. The apparatus 10 is presented for illustration purposes only and is not intended to be limiting.

The elongated shaft 9 has a proximal portion 12 in the shape of an elongated catheter body, an intermediate deflection section 14, and distal portion 14A. The deflection control handle 16 is attached to the proximal end of the catheter body 12. The distal portion 14A of the shaft is coupled to the end effector 100 via a connector tubing 46. The elongated shaft 9 forms a tubular catheter body sized and otherwise configured to traverse vasculature. The end effector 100 has a plurality of loop members 1, 2, 3 that overlap at a common distal vertex and are joined at the distal vertex with a mechanical linkage 50.

When the device is unconstrained and aligned, the proximal portion 12, intermediate section 14, distal portion 14A, and end effector 100 are generally aligned along a longitudinal axis L-L. The intermediate section 14 can be configured to bend to deflect the distal portion 14A and end effector 100 from the longitudinal axis L-L.

The end effector 100 can be collapsed (compressed toward the longitudinal axis L-L) to fit within a guiding sheath or catheter (not illustrated). The shaft 9 can be pushed distally to move the end effector 100 distally through the guiding sheath. The end effector 100 can be moved to exit a distal end of the guiding sheath via manipulation of the shaft 9 and/or control handle 16. An example of a suitable guiding sheath for this purpose is the Preface Braided Guiding Sheath, commercially available from Biosense Webster, Inc. (Irvine, California, USA).

The end effector 100 has first, second and third loop members 1, 2, and 3. Each loop member 1, 2, 3 has two spines 1A, 1B, 2A, 2B, 3A, 3B and a connector 1C, 2C, 3C that connects the two spines of the respective loop member 1, 2, 3. Spines 1A, 1B of a first loop member 1 are connected by a first connector 1C; spines 2A, 2B of a second loop member 2 are connected by a second connector 2C; and spines 3A, 3B of a third loop member 3 are connected by a third connector 3C. The connectors 1C, 2C, 3C are preferably arcuate members as illustrated.

For each loop member 1, 2, 3 the spines 1A, 1B, 2A, 2B, 3A, 3B in the respective pair of spines can be substantially parallel to each other along a majority of their respective lengths when the end effector 100 is expanded in an unconstrained configuration as illustrated in FIG. 1A. Preferably, all spines in the end effector are parallel to each other along the majority of their respective lengths when the end effector 100 is in the unconstrained configuration. Even when all spines are parallel, the spines are not necessarily all coplanar as described in greater detail elsewhere herein, for instance in relation to FIGS. 4A through 4C.

Each spine 1A, 1B, 2A, 2B, 3A or 3B can have a length ranging between about 5 and 50 mm, preferably about 10 and 35 mm, and more preferably about 28 mm. The parallel portions of each spine 1A, 1B, 2A, 2B, 3A, 3B can be spaced apart from each other by a distance ranging between about 1 mm and 20 mm, preferably about 2 and 10 mm, and more preferably about 4 mm. Each spine 1A, 1A, 1B, 2A, 2B, 3A, 3B preferably carries at least eight electrodes per spine member. The end effector preferably includes six spines as illustrated. With eight electrodes on six spines, the end effector 100 includes forty-eight electrodes.

A distal electrode 38D and a proximal electrode 38P are positioned near the distal portion 14A of the shaft 9. The electrodes 38D and 38P can be configured to cooperate (e.g. by masking of a portion of one electrode and masking a different portion on the other electrode) to define a referential electrode (an electrode that is not in contact with tissues). One or more impedance sensing electrodes 38R can be configured to allow for location sensing via impedance location sensing technique, as described in U.S. Pat. Nos. 5,944,022; 5,983,126; and 6,445,864, of which a copy is provided in the priority U.S. Provisional Patent Application 63/031,955 and incorporated herein by reference.

Figure 2A:
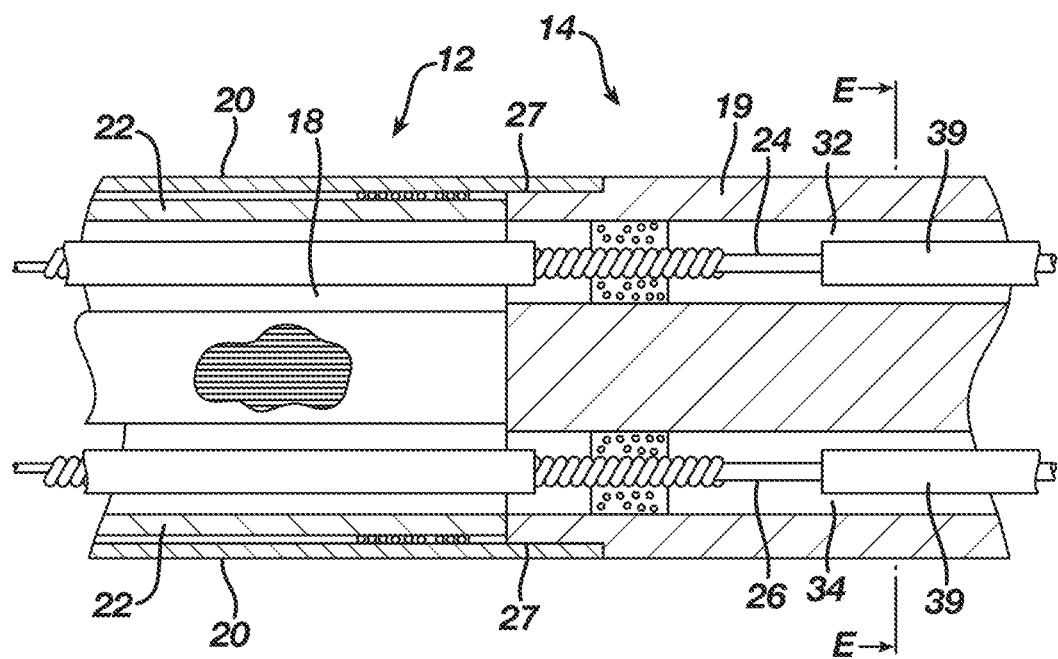
FIGS. 2A through 2C are illustrations of an intermediate section and distal portion of a shaft of the catheter in greater detail according to aspects of the present invention.
Figure 2B:
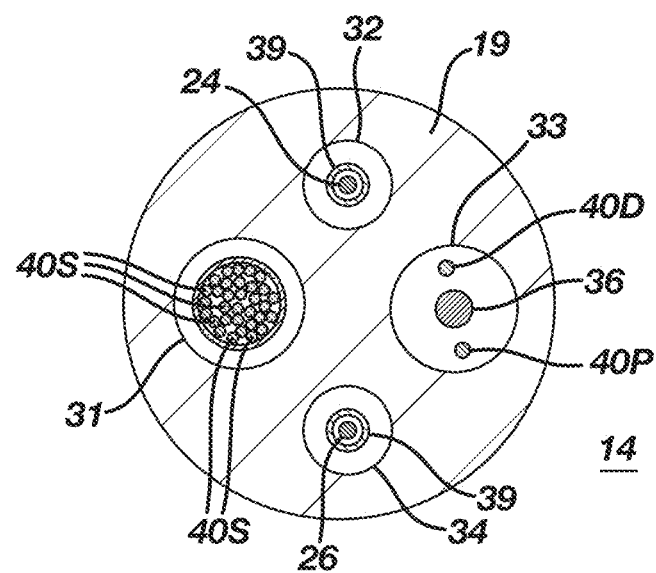
Figure 2C:
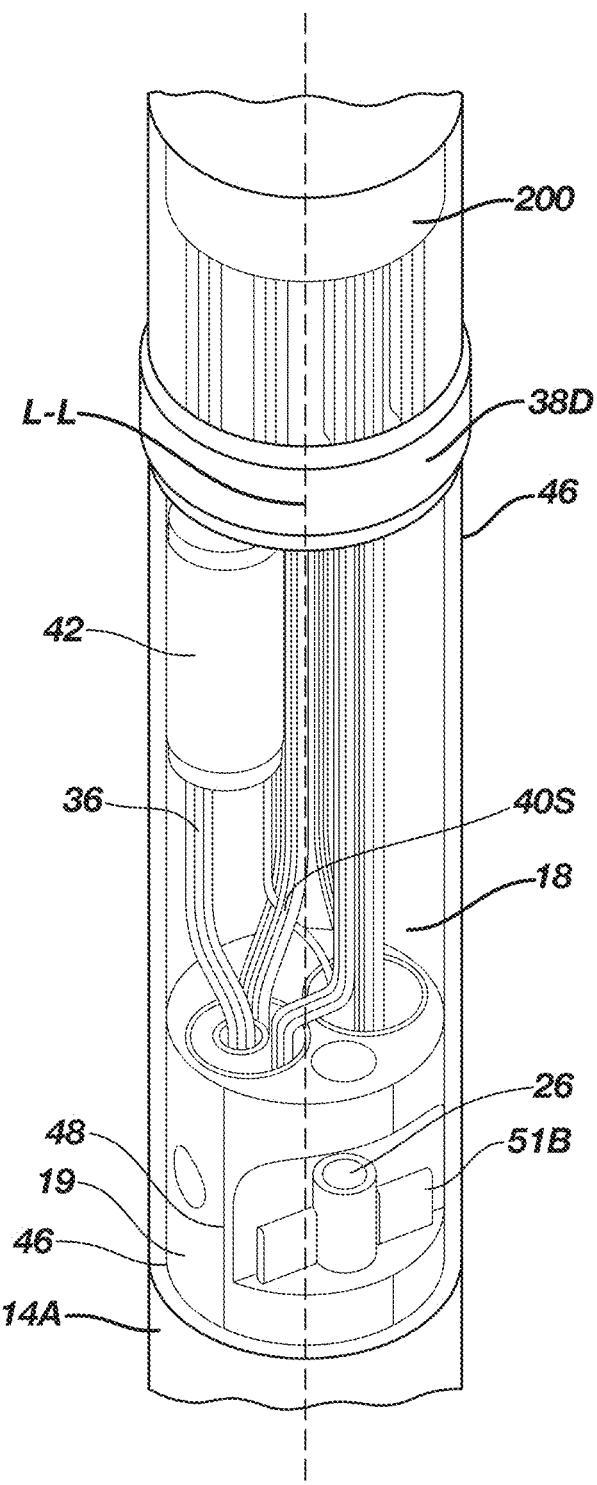

FIGS. 2A through 2C illustrates the intermediate section 14 and distal portion 14A of the shaft 9 of the apparatus in greater detail. FIG. 2A is a cross sectional view, along the longitudinal axis L-L, of the elongated shaft 9 at the interface between the proximal portion 12 and intermediate section 14. FIG. 2B is a cross sectional view of the intermediate section 14 orthogonal to the longitudinal axis L-L. FIG. 2C is an isometric view of the distal portion 14A and connector tubing 46 with certain components illustrated as transparent.

As illustrated in FIG. 2A, the catheter body 12 can be an elongated tubular construction having a single axial passage or central lumen 18. The catheter body 12 is flexible, i.e., bendable, but substantially non-compressible along its length. The catheter body 12 can be of any suitable construction and made of any suitable material. In some embodiments, the catheter body 12 has an outer wall 20 made of polyurethane or PEBAX. The outer wall 20 may include an imbedded braided mesh of stainless steel or the like to increase torsional stiffness of the catheter body 12 so that, when the control handle 16 is rotated, the intermediate section 14 will rotate in a corresponding manner.

The outer diameter of the catheter body 12 is preferably no more than about 8 French, more preferably about 7 French. The thickness of the outer wall 20 is thin enough so that the central lumen 18 can accommodate at least one puller wire, one or more lead wires, and any other desired wires, cables or tubes. If desired, the inner surface of the outer wall 20 is lined with a stiffening tube 22 to provide improved torsional stability. In some embodiments, the outer wall 20 has an outer diameter of from about 0.090 inch to about 0.094 inch (from about 2.3 mm to about 2.4 mm) and an inner diameter of from about 0.061 inch to about 0.065 inch (from about 1.5 mm to about 1.7 mm).

As illustrated particularly in FIG. 2B, the intermediate section 14 can include a shorter section of tubing 19 having multiple lumens, for example, four off-axis lumens 31, 32, 33 and 34. The first lumen 31 carries a plurality of lead wires 40S for ring electrodes 37 carried on the spines 1A, 1B, 2A, 2B, 3A, 3B. The second lumen 32 carries a first puller wire 24. The third lumen 33 carries a cable 36 for an electromagnetic position sensor 42 and lead wires 40D and 40P for distal and proximal ring electrodes 38D and 38P carried on the catheter proximally of the end effector 100. Electromagnetic location sensing technique is described in U.S. Pat. Nos. 5,391,199; 5,443,489; 5,558,091; 6,172,499; 6,590,963; and 6,788,967 of which a copy is provided in the priority U.S. Provisional Patent Application 63/031,955 and incorporated herein by reference. The magnetic location sensor 42 can be utilized with impedance sensing electrode 38R in a hybrid magnetic and impedance position sensing technique known as ACL described in U.S. Pat. Nos. 7,536,218; 7,756,567; 7,848,787; 7,869,865; and 8,456,182, of which a copy is provided in the priority U.S. Provisional Patent Application 63/031,955 and incorporated herein by reference.

The fourth lumen 34 (for example, diametrically opposite of the second lumen 32 as illustrated) carries a second puller wire 26. The tubing 19 is made of a suitable non-toxic material that is preferably more flexible than the catheter body 12. One suitable material for the tubing 19 is braided polyurethane, i.e., polyurethane with an embedded mesh of braided stainless steel or the like. The size of each lumen is sufficient to house the lead wires, puller wires, the cable and any other components.

The useful length of the catheter shaft 9, i.e., that portion of the apparatus 10 that can be inserted into the body excluding the end effector, can vary as desired. Preferably the useful length ranges from about 110 cm to about 120 cm. The length of the intermediate section 14 is a relatively smaller portion of the useful length, and preferably ranges from about 3.5 cm to about 10 cm, more preferably from about 5 cm to about 6.5 cm.

Catheter body proximal portion 12 can be attached to the intermediate section 14 as shown and described in FIGS. 2A and 2B of U.S. Pat. No. 9,820,664, of which a copy is provided in the priority U.S. Provisional Patent Application 63/031,955 and incorporated herein by reference. If desired, a spacer (not shown) can be located within the catheter body 12 between the distal end of the stiffening tube (if provided) and the proximal end of the intermediate section 14. The spacer can provide a transition in flexibility at the junction of the catheter body 12 and intermediate section 14, which can allow this junction to bend smoothly without folding or kinking. A catheter having such a spacer is described in U.S. Pat. No. 5,964,757 of which a copy is provided in the priority U.S. Provisional Patent Application 63/031,955 and incorporated herein by reference.

The distal portion 14A of the shaft 9 can be substantially contiguous with the intermediate section 14 such that the intermediate section comprises the distal portion 14A; the distal portion being distinguished from the intermediate section 14 by the positioning of one or more (optional) ring electrodes 38R. As referred to herein, the distal portion 14A of the shaft 9 can therefore correspond to a distal portion of the intermediate section 14.

As illustrated in FIG. 2C, the distal portion 14A of the shaft 9 is coupled to the end effector 100 with a connector tubing 46. The connector tubing 46 includes an insert for connection of loop members 1, 2, 3 to provide electrical connection through the intermediate portion 14 of the catheter body. The connector tubing 46 can be affixed to the distal portion 14A of the catheter by glue or the like.

The connector tubing 46 can be shaped to house various components such as an electromagnetic position sensor, a puller wire anchor, ring electrodes 38D, 38P, etc. The connector tubing 46 can include a central lumen 48 to house various components. An outer circumferential notch 27 (FIG. 2A) in the distal end of the tubing 19 that receives the inner surface of the proximal end of the connector tubing 46 can be used to attach the connector tubing 46 and the intermediate section 14 (distal portion 14A of shaft 9). The intermediate section 14 and connector tubing 46 are attached by glue or the like.

The connector tubing 46 can house various components, including an electromagnetic position sensor 42, and a distal anchor bar for a first puller wire 24 and another anchor bar 51B for a second puller wire 26. Only the anchor 51B for second puller wire 26 is visible in FIG. 2C. The anchor bar for the first puller wire can be configured as a mirror image to the illustrated puller wire anchor bar 51B. Carried on the outer surface of the tubing 19 near the distal end of the intermediate deflection section 14 (distal portion 14A of the shaft 9), a distal ring electrode 38D is connected to lead wire formed in the side wall of the tubing 19. The distal end of the lead wire is welded or otherwise attached to the distal ring electrode 38D as known in the art.

Figure 3A:
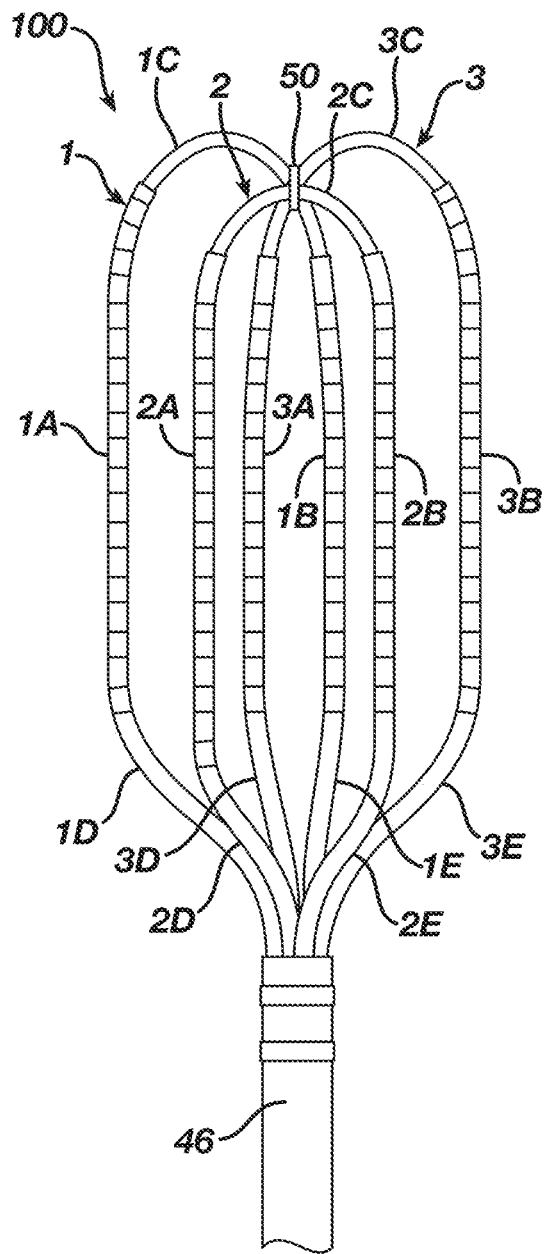
FIGS. 3A and 3B are illustrations of a front and side view of the end effector according to aspects of the present invention.
Figure 3B:
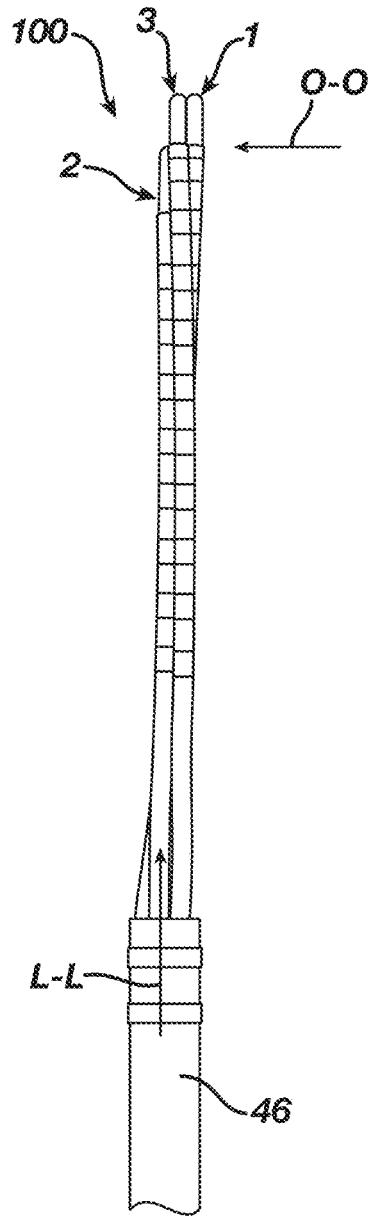

FIGS. 3A and 3B are illustrations of a front and side view of the end effector 100. The three loop members 1, 2, 3 overlap at a common distal vertex 50 along the longitudinal axis L-L. Each of the loop members 1, 2, 3, respectively include proximal end segments 1D, 2D, 3D, 1E, 2E, 3E affixed to the distal portion 14A of the elongated shaft 9 of the apparatus 10.

The end effector 100 is in an unconstrained configuration as illustrated in FIGS. 3A and 3B. As better visualized in the side view of FIG. 3B, when the end effector is unconstrained, the loop members 1, 2, 3 are not coplanar with each other. FIG. 3B also illustrates an orthogonal axis O-O orthogonal to the longitudinal axis L-L and approximately orthogonal to the front view of the end effector 100.

FIGS. 4A through 4D are illustrations depicting orientation of loop members of the end effector. FIGS. 4B and 4C are cross sectional views of the end effector 100 and as indicated in FIG. 4A. FIG. 4D is a view of the end effector 100 looking proximally from a distal end of the end effector 100 as indicated in FIG. 4A.

FIG. 4B illustrates a cross sectional view through the connector 46. The connector 46 includes a tubular insert 200 that has its center coinciding with the longitudinal axis L-L. Orthogonal planes P4 and P5 are in alignment with the longitudinal axis to define four quadrants in the insert 200. A parallel reference plane P5 is approximately parallel to the front view of the end effector 100 illustrated in FIG. 3A. An orthogonal reference plane P4 is approximately orthogonal to the parallel reference plane P5 and approximately parallel to the orthogonal axis O-O. Apertures 202, 204, 206, 208, 210, 212 of the insert 200 are sized, positioned, and otherwise configured for insertion of respective end segments 1D, 2D, 3D, 1E, 2E, 3E. Openings 214, 216 are disposed on orthogonal plane P4 for insertion of puller wires or electrical wires as well as any other components to and from the end effector 100. Components which traverse the apertures 202, 204, 206, 208, 210, 212 and openings 214, 216 are not illustrated in FIG. 4B for the purposes of illustration.

With this arrangement of apertures 202, 204, 206, 208, 210 and 212, loop members 1, 2 and 3 are arrayed in a non-coplanar unconstrained arrangement, shown in the sectional view of FIG. 4C (as viewed from the proximal end), whereby loop 3 defines a plane P3 (demarcated by spines 3A and 3B with connector 3C) that intersects orthogonal plane P4 with loop 1 having a plane P1 (demarcated by spines 1A and 1B with connector 1C) that intersects both orthogonal planes P4 and P5 and loop 2 having a plane P2 (demarcated by spines 2A and 2B and connector 2C) that intersects orthogonal plane P4 and is substantially parallel to orthogonal plane P5. FIG. 4D is a view of the distal end of the end effector looking proximally. In particular, loop 1 (defined by spines 1A, 1B and connector 1C) is arrayed to define plane P1 that is contiguous to or extend through spines 1A, 1B and loop 1C whereas spines 2A, 2B and connector 2C of loop 2 are arrayed to define a plane P2 that intersects with plane P1. Spines 3A, 3B and connector 3C of loop 3 are arrayed to define a plane P3 that intersects with both planes P1 and P2. The planes P1, P2, and P3 defined by the respective loops 1, 2 and 3 are configured so that the loops P1, P2 and P3 are not contiguous to or arrayed such that a common plane passes through the loops. Thus, planes P1, P2 and P3 are non-parallel and intersects each other. It is noted that the longitudinal axis L-L may be contiguous to the second plane P2. In alternative embodiment, longitudinal axis L-L may be disposed in between a region bounded by planes P1, P2 and P3.

FIGS. 4A through 4D are one example of non-coplanar arrangement of loop members 1, 2, 3 in an end effector. There are numerous possible arrangements non-coplanar arrangements of loop members which can result in an end effector having the general appearance of the illustrated end effector 100.

Figure 5A:
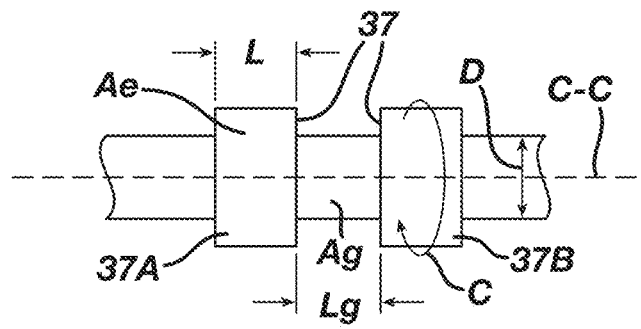
FIG. 5A is an illustration depicting electrode spacing and dimensions on the end effector according to aspects of the present invention.

FIG. 5A is an illustration depicting electrode spacing and dimensions on the end effector. The electrodes 37 can include one or more pairs of closely-spaced bipolar microelectrodes 37A, 37B which are configured to pick up electrocardiogram signals from tissue. In the present example, the microelectrodes 37A, 37B of a pair has a separation space gap distance (Lg) therebetween of approximately 1 mm to 200 microns and preferably no greater than about 200 microns. Each electrode 37A, 37B has an electrode area (Ae) and electrode length (L). The electrode length can be from about 2 mm to about 0.5 mm. Each spine electrode 37 preferably has a length of 1 mm to 0.5 mm. The electrodes 37 as illustrated are cylindrical such that the electrode area is calculated as a produce of the circumference (C) and length (L) of the electrode. The spine has a diameter (D).

Additionally, or alternatively, the microelectrodes 37A, 37B need not completely circumscribe the respective loop 1, 2, 3; in which case the microelectrodes 37A, 37B can have a rectangular shape that is rectilinear or arced having a width (W) such that the electrode area (Ae) is a produce of the electrode length (L) and width (W), the width being the arc length when the rectangular shape is arced. In examples where the electrode pair configurations are in shapes other than rectilinear, rectangular, or cylindrical, a conversion factor CF may be used to determine the appropriate gap distance between the electrodes based on the known area of either one of the pair of electrodes. The conversion factor CF may range from about 2 to 0.1 in the inverse of the same root dimensional unit as the planar area of an electrode. In one example, where the planar area of one electrode is about 0.08 squared-mm, the smallest gap distance (Lg) along the longitudinal axis extending through both electrodes can be determined by applying the conversion factor CF (in the inverse of the same root dimensional unit of the area or mm) to arrive at a gap distance Lg of about 100 microns. In another example where the area of one electrode is 0.24 squared-mm, the conversion factor CF (in the inverse of the same root dimensional unit or $mm^{-1}$) can be 1.25 $mm^{-1}$ or less, giving the range of the smallest gap distance Lg from about 300 microns to about 24 microns. Regardless of the shape of the electrodes, a preferred conversion factor CF is about 0.8 (in the inverse of the same root dimensional unit for the electrode area).

Figure 5B:
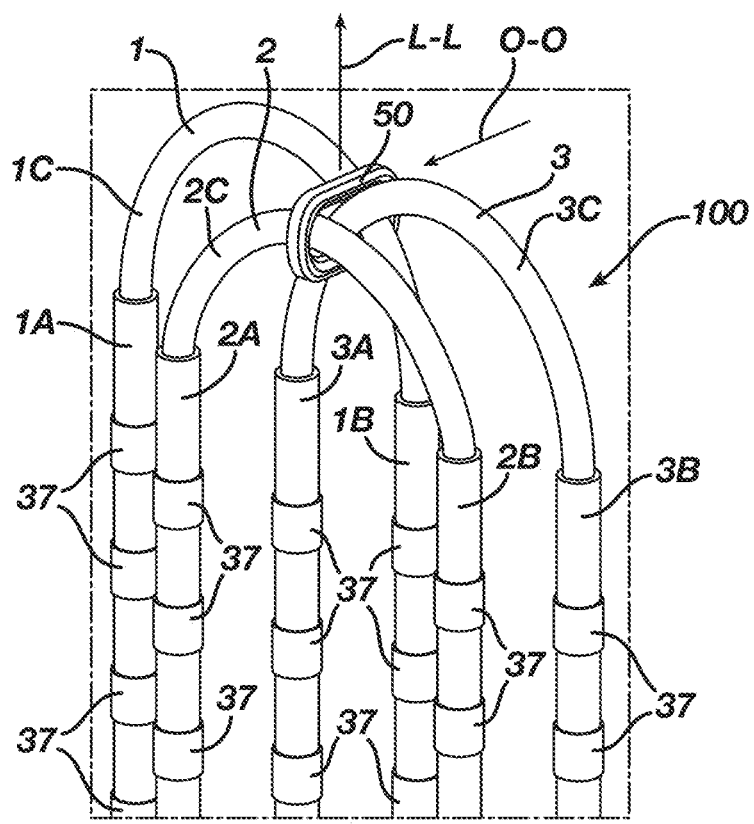
FIG. 5B is another illustration of the end effector including a mechanical linkage according to aspects of the present invention.

FIG. 5B is another illustration of the end effector 100 including a mechanical linkage 50. At least one pair of closely-spaced bipolar microelectrodes 37A, 37B is provided on each spine 1A, 2A, 3A, 1B, 2B, 3B in the present example. More particularly, each spine 1A, 2A, 3A, 1B, 2B, 3B carries four pairs of bipolar microelectrodes 37 corresponding to eight microelectrodes 37 per spine. This number may be varied as desired. FIG. 5B also illustrates a clip 50 coupling connectors 1C, 2C, 3C together in a single connection point. The clip 50 functions to maintain a spatially fixed arrangement between the loops 1, 2, 3 at the common distal vertex.

Figure 6A:
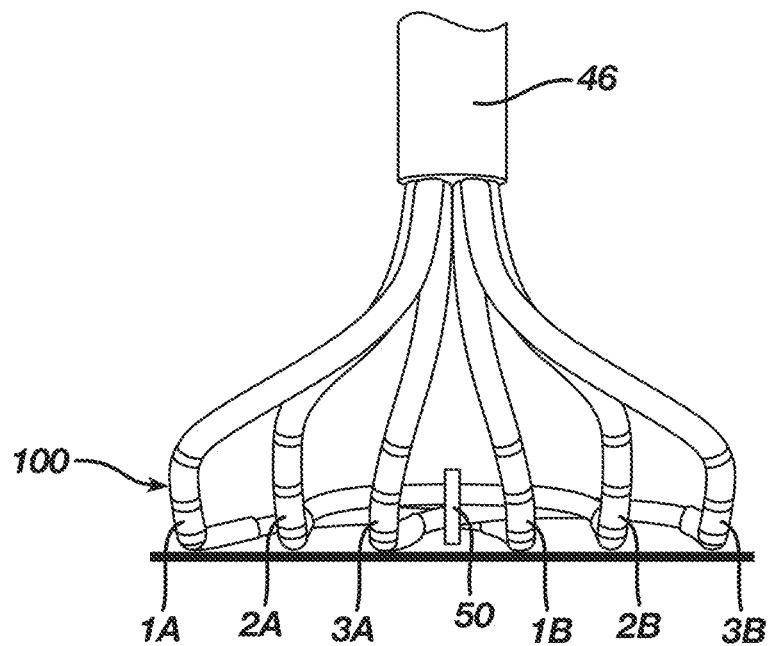
FIGS. 6A and 6B are illustrations of views of the end effector pressed to a planar surface according to aspects of the present invention.
Figure 6B:
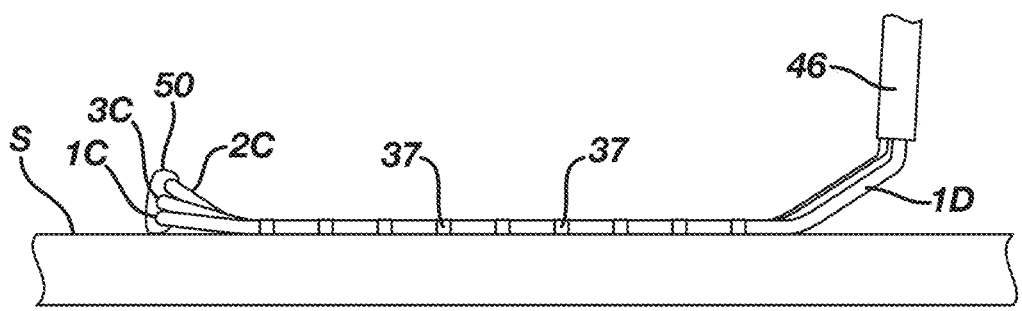

FIGS. 6A and 6B are illustrations of views of the end effector pressed to a planar surface S. In the illustrated example, the loop members 1, 2, 3 can be pressed to the planar surface S via manipulation of the shaft 9 of the device. More specifically, when the end effector 100 is positioned within a patient, manipulation of the catheter body 12 and the control handle 16 can be used to position the end effector 100 against a surface within a wall of an internal cavity of the patient such internal walls of the heart and/or blood vessels. When the end effector 100 is positioned against the planar surface S, a majority of each length of each spine 1A, 2A, 3A, 1B, 2B, 3B can become contiguous and aligned to the planar surface. Further, when the end effector 100 is positioned against the planar surface S, a majority of each length of each spine 1A, 2A, 3A, 1B, 2B, 3B can become aligned with a majority of each length of the other spines. The surface S need not necessarily be planar in order for the spines 1A, 2A, 3A, 1B, 2B, 3B to become contiguous and aligned to the surface. The end effector 100 may be able to conform to a curved surface, for instance.

As illustrated in FIG. 6B, when the majority of each spine 1A, 2A, 3A, 1B, 2B, 3B is pressed to the surface S, the connecting segments 1C, 2C, 3C can be stacked on top of the surface S at the distal vertex at the linkage 50. A first connecting segment 1C nearest to the surface S can be separated from the surface S by the linkage 50. A second connecting segment 3C stacked onto the first connecting segment 1C can be separated from the surface S by the linkage 50 and the first connecting segment 1C. A third connecting segment 2C can be separated from the surface S by the linkage 50 and the first and second connecting segments 1C, 3C. Therefore, at least a portion of each connecting segment 1C, 2C, 3C can be separated from the planar surface S when the majority of each spine 1A, 2A, 3A, 1B, 2B, 3B is pressed to the planar surface. Alternatively, the linkage 50 can be inset into the first connecting segment 1C such that the first connecting segment is substantially contiguous to the planar surface S. In that case, only the second and third connecting segments 3C, 2C are separated from the planar surface S at the distal vertex.

Proximal segments 1D, 2D, 3D, 1E, 2E, 3E of the loop members 1, 2, 3 can be bent such that at least a portion of each of the proximal segments curves away from the surface S.

When the majority of each spine 1A, 2A, 3A, 1B, 2B, 3B is pressed to the surface S, at least some of the electrodes 37 on each spine can be in contact with the surface S. In some examples, every electrode 37 on each spine can be in contact with the surface 37.

When the majority of each spine 1A, 2A, 3A, 1B, 2B, 3B is pressed to the surface S, the majority of each respective length of each loop member can become contiguous to the surface S, where the respective length of each loop member includes the length of the respective loop member's spines 1A, 2A, 3A, 1B, 2B, 3B, connectors 1C, 2C, 3C, and proximal segments 1D, 2D, 3D, 1E, 2E, 3E (distal to the connector tubing 46).

Figure 7:
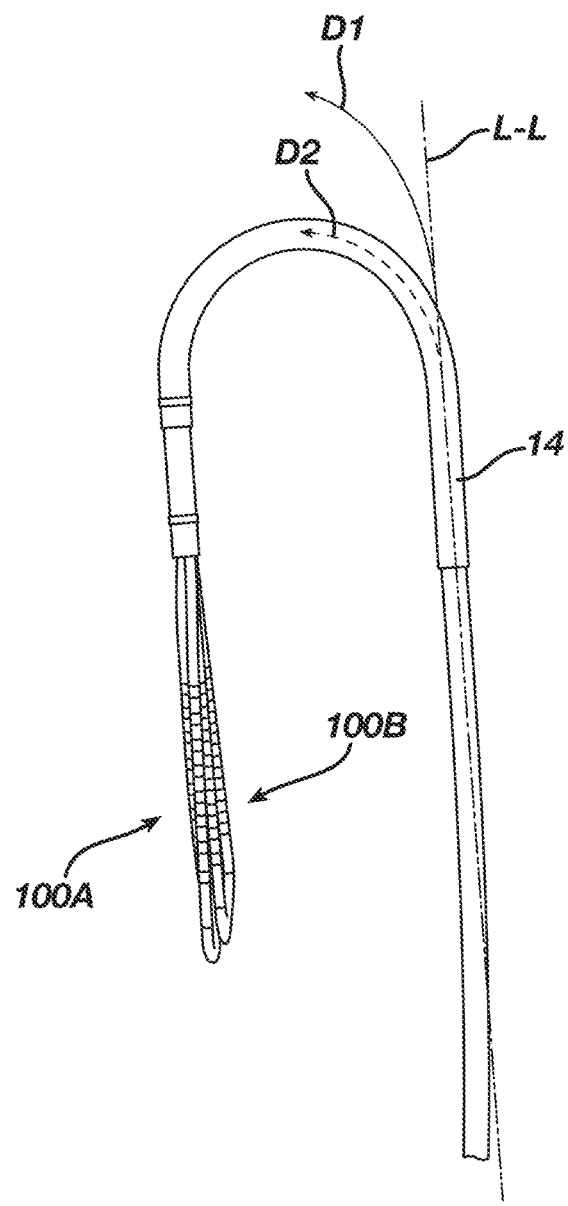
FIG. 7 is an illustration of an intermediate section of the shaft of the catheter deflected with a puller wire.

FIG. 7 is an illustration of the intermediate section 14 of the shaft of the catheter deflected at approximately 360°. The end effector 100 has a first side 100A and a second side 100B. This allows the user to place first side 100A (or 100B) against the tissue surface, with at least the intermediate section 14 (if not also a distal portion of the catheter body 12) generally perpendicular to the tissue surface, and actuates the control handle to deflect the intermediate deflection section 14 to arrive at various deflections or radii of curvature (e.g., arrows D1 and D2) such that the second side 100B deflects back toward the catheter body 12. Being positioned as such may allow dragging of the second side 100B of the end effector 100 including the loop members 1, 2, 3 across the tissue surface as the intermediate section 14 is deflecting. The intermediate section can be deflected via manipulation of the puller wires 24, 26 illustrated in FIGS. 2A through 2C. The puller wires 24, 26 can be two separate tensile members or parts of a single tensile member. In some examples, the puller wires 24, 26 can be actuated for bi-directional deflection of the intermediate section 14. The puller wires 24, 26 can be actuated by mechanisms in the control handle 16 that are responsive to a thumb control knob or a deflection control knob 11. Suitable control handles are disclosed in U.S. Pat. Nos. 6,123,699; 6,171,277; 6,183,435; 6,183,463; 6,198,974; 6,210,407 and 6,267,746, of which a copy is provided in the priority U.S. Provisional Patent Application 63/031,955 and incorporated herein by reference.

Details of the construction of puller wires including anchor via T-bars 51B (see FIG. 2C) at the intermediate section 14, as known in the art and described in, for example, U.S. Pat. Nos. 8,603,069 and 9,820,664, of which a copy is provided in the priority U.S. Provisional Patent Application 63/031,955 and incorporated herein by reference. The puller wires 24 and 26 can be made of any suitable metal, such as stainless steel or Nitinol. The puller wires 24, 26 are preferably coated with TEFLON or the like. The coating imparts lubricity to the puller wires. The puller wires preferably have a diameter ranging from about 0.006 to about 0.010 inch.

Figure 8A:
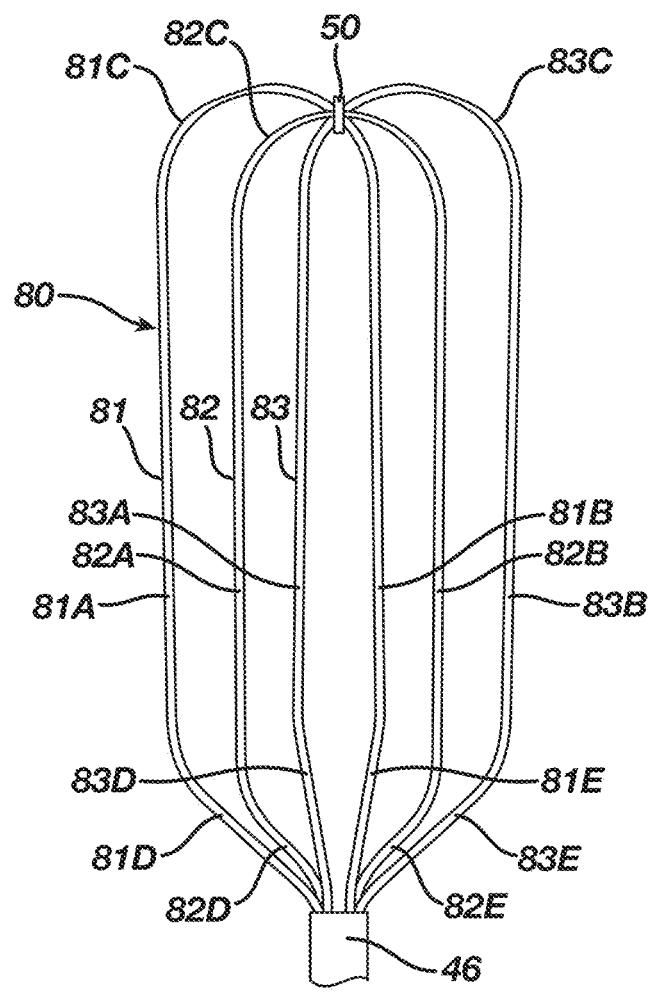
FIGS. 8A and 8B are illustrations of views of support frames of the end effector in an unconstrained configuration according to aspects of the present invention.
Figure 8B:
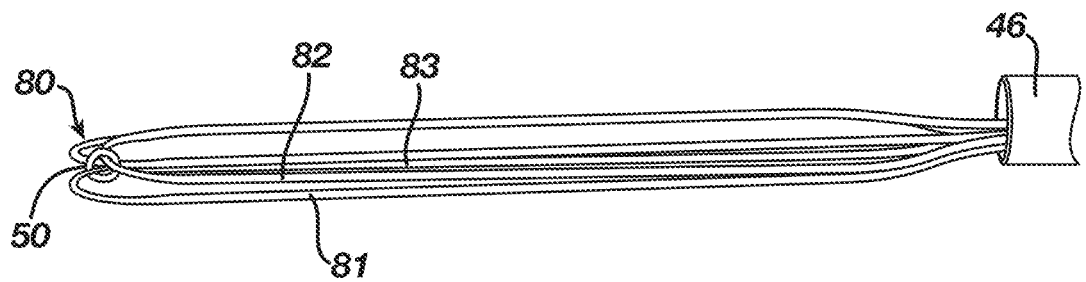
Figure 8C:
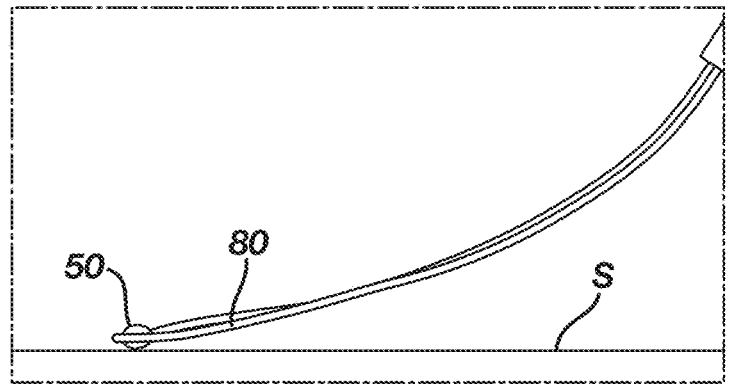
FIGS. 8C and 8D are illustrations of the support frames of FIGS. 8A and 8B being pressed to a surface according to aspects of the present invention.
Figure 8D:
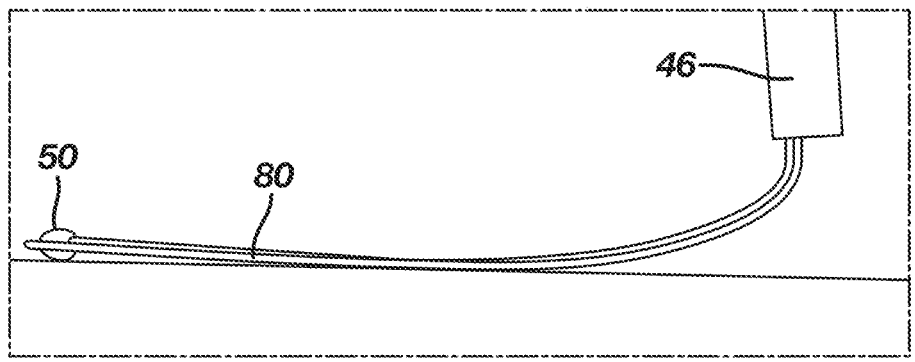

FIGS. 8A through 8D are illustrations of a support frame assembly 80 of the end effector 100. FIGS. 8A and 8B illustrate the support frame assembly 80 in an unconstrained configuration. FIGS. 8C and 8D illustrate the support frame assembly 80 being pressed to a surface S. When the end effector 100 is assembled, the loop members 1, 2, 3 each includes a respective support frame 81, 82, 83. The support frame assembly 80 extends into the connector tubing 46 to mechanically affix the loop members 1, 2, 3 to the shaft 9. The support frames 81, 82, 83 provide structural integrity for the loop members 1, 2, 3. The support frames 81, 82, 83 can include plastic or metal cut-off sheets, plastic or metal round wire, plastic or metal square wire, or other suitable biocompatible material. In the preferred embodiments, the support frames are made from shape memory material such as, for example, nitinol. For the purposes of testing and illustration, the support frame assembly 80 is joined at a distal vertex with mechanical linkage 50. In the assembled end effector 100, the support frames 81, 82, 83 can be assembled by virtue of a mechanical linkage affixed to an outer housing of the loop members 1, 2, 3 or a direct linkage between the support frames 81, 82, 83.

When the end effector is unconstrained, each of the respective support frames 81, 82, 83 defines a respective looped path of its respective loop member 1, 2, 3 as illustrated in FIG. 8A. Each support frame 81, 82, 83 includes respective parallel segments 81A, 82A, 83A, 81B, 82B, 83B that extend through corresponding spines 1A, 2A, 3A, 1B, 2B, 3B of the end effector 100. Each support frame 81, 82, 83 includes respective proximal segments 81D, 82D, 83D, 81E, 82E, 83E that extend through corresponding proximal segments 1D, 2D, 3D, 1E, 2E, 3E of respective loop members 1, 2, 3. The proximal segments 81D, 82D, 83D, 81E, 82E, 83E extend into the connector tubing 46 to join the end effector 100 to the shaft 9. Each support frame 81, 82, 83 includes a respective connecting segments 81C, 82C, 83C that extends between the respective pair of parallel segments 81A, 82A, 83A, 81B, 82B, 83B and through the respective connecting segment 1C, 2C, 3C of the respective loop member 1, 2, 3.

When the end effector is unconstrained, at least one of the parallel segments 81A, 82A, 83A, 81B, 82B, 83B is not aligned in a common plane with other parallel segments. Said another way, at least one of the looped paths is non-coplanar with one or both of the other looped paths. The pair of parallel segments 81A, 82A, 83A, 81B, 82B, 83B for each support frame 81, 82, 83 can define a plane for the pair's respective support frame 81, 82, 83. The support members 81, 82, 83 can generally align to define three planes P3, P4, P5 as illustrated in FIG. 4C when the end effector 100 is in the unconstrained configuration.

When the loop member 1, 2, 3 is pressed to a surface S as in the sequence of illustrations of FIGS. 8C and 8D, a majority of the respective length of each segment in each of the respective pairs of parallel segments can become approximately coplanar with a majority of the respective length of each of the other segments in each of the respective pairs of parallel segments. The support members 80 can become aligned with the surface S as the loop members 1, 2, 3 are pressed into the surface S as illustrated in FIG. 6B. When the surface S is planar, the parallel segments 81A, 82A, 83A, 81B, 82B, 83B become coplanar with each other along a majority of their respective lengths.

Each support frame 81, 82, 83 can include knuckles to promote conformance of the loop members 1, 2, 3 to the surface S. The knuckles can be spaced uniformly or non-uniformly along the looped path of a respective support member 81, 82, 83. Knuckle features can include thinned out sections of the material of the support members 81, 82, 83. Additionally, or alternatively, the knuckle features can include hinge mechanisms.

Figure 9A:
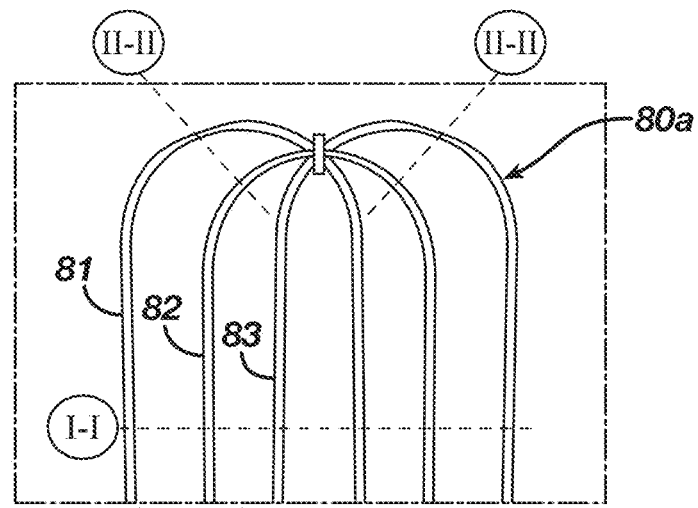
FIGS. 9A and 9B are illustrations of example support frames that vary in cross section along a respective looped path of each support frame according to aspects of the present invention.
Figure 9B:
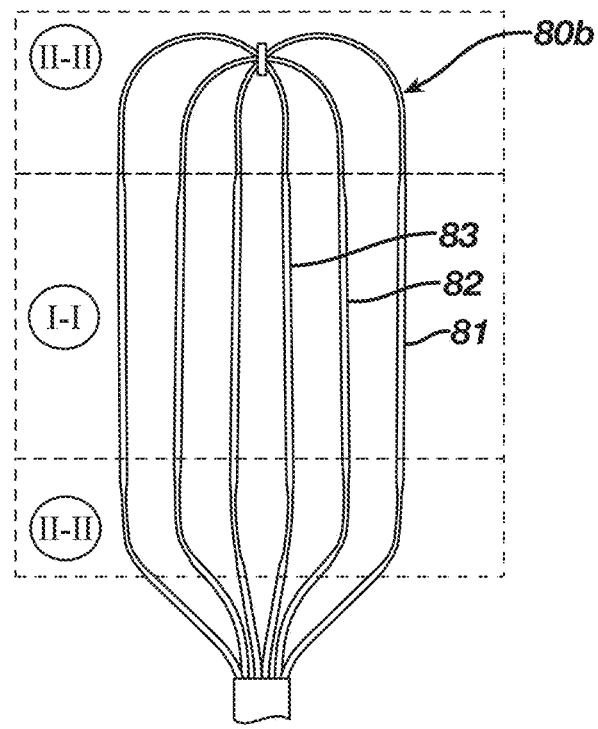

FIGS. 9A and 9B are illustrations of example support frames that vary in cross section along a respective looped path of each support frame. Each of the support frames 80 can respectively have a cross sectional shape that varies along the individual support frame's looped path, where the cross sectional shape is taken from a cross section orthogonal to the direction of the looped path. FIGS. 9A and 9B illustrate two different example support frame assemblies 80a, 80b. Each of the example support frame assemblies 80a, 80b having regions I-I with a cross sectional area configured to resist deflection and regions II-II configured to facilitate deflection. The regions I-I configured to resist deflection can have a larger cross sectional area compared to the regions II-II configured to facilitate deflection. Alternatively, the regions I-I configured to resist deflection can be flattened to resist deflection in the direction of long sides of the cross section while having a similar cross section to non-flattened, or less flattened regions II-II. That is, in FIG. 9A, the thin sections are intended to promote sheath retraction (lower force for the frame to collapse) while in FIG. 9B, the distal II-II section is intended still for frame collapsing, but the proximal II-II section (knuckles) are intended to promote deflection with respect to the longitudinal axis L-L.

Figure 10A:
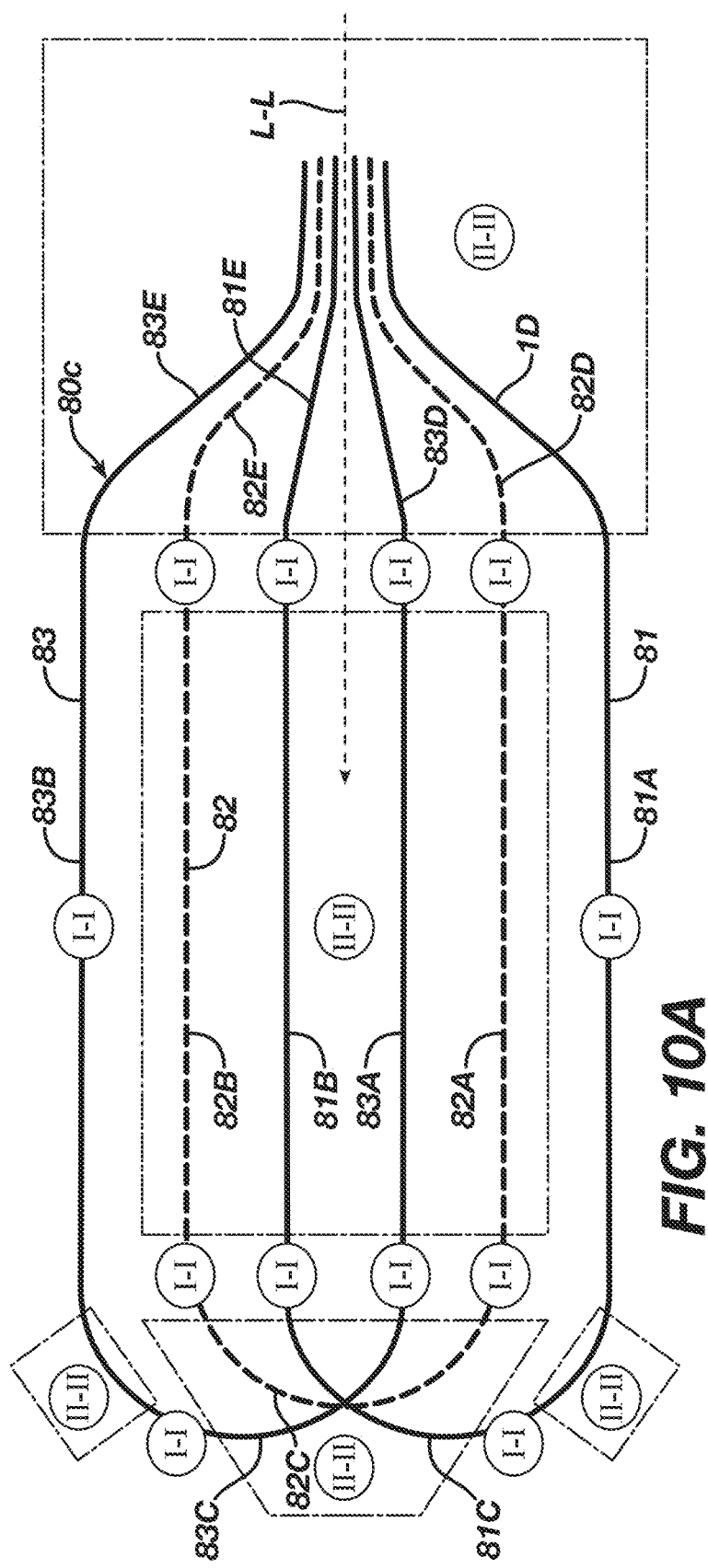
FIG. 10A is an illustration of example support frames of the end effector according to aspects of the present invention.

FIG. 10A is another illustration of an example support frame assembly 80c of the end effector 100. FIGS. 10B through 10E are illustrations of cross sectional areas of the example support frame as indicated in FIG. 10A. FIGS. 10F and 10G are illustrations of example transitions schemes between wide and narrow regions.

FIG. 10A shows a top view (looking down onto the second plane P2) of another example support frame assembly 80c of an effector 100 (see FIG. 4C for orientation). The support frames 81, 82, 83 are annotated with Roman Numerals indicating locations having an approximate cross sectional shape as illustrated in FIGS. 10B through 10E. Each cross section is taken orthogonal to the respective looped path of each support frame 81, 82, 83. Each support frame 81, 82, 83 varies in cross section along its looped path. By varying the cross sections, each support frame 81, 82, 83 has variable stiffness/flexibility along its looped path.

Figures 10B, 10C, 10D, 10E:
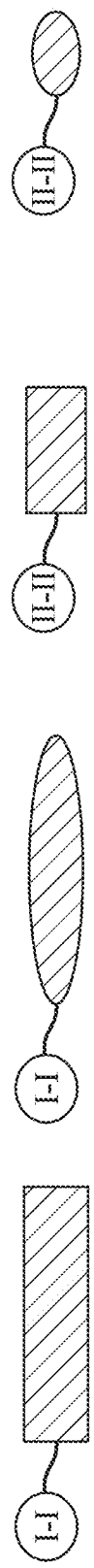
FIGS. 10B through 10E are illustrations of cross sectional areas of the example support frame as indicated in FIG. 10A.

FIG. 10B shows a cross section having a substantially rectangular shape and corresponding to sections of each support frame 81, 82, 83 annotated with Roman Numerals I-I. When unconstrained, the parallel segments 81A, 82A, 83A, 81B, 82B, 83B define a respective plane for each support frame 81, 82, 83. The rectangle is long in the plane of the respective support frame. The rectangle is short in the direction orthogonal to the plane of the respective support frame 81, 82, 83. As understood by a person skilled in the pertinent art, this shape permits greater flexibility along an axis aligned with the short edges of the shape compared to the flexibility along an axis aligned with the long edges of the shape. In some examples, the width of the long side of the rectangle is about 0.012 inches (0.3 millimeters) and the short side of the rectangle is about 0.008 inches (0.2 millimeters).

FIG. 10C shows an alternative cross section having an ovoid or oval-shaped shape and corresponding to sections of each support frame 81, 82, 83 annotated with Roman Numerals I-I. Like the rectangle illustrated in FIG. 10B, the oval illustrated in FIG. 10C is long in the plane of the respective support frame 81, 82, 83 and short orthogonal to the respective plane, affecting the relatively flexibility in each direction as understood by a person skilled in the pertinent art. In some examples, the width of the long side of the oval is about 0.012 inches (0.3 millimeters) and the short side of the oval is about 0.005 inches (0.13 millimeters).

FIG. 10D shows a cross section corresponding to sections of each support frame 81, 82, 83, annotated with Roman Numerals II-II. The cross section illustrated in FIG. 10D has a substantially rectangular shape having a width that is shorter in the plane of the respective support frame 81, 82, 83 compared to the width of the rectangular cross section illustrated in FIG. 10B. The height of the cross section illustrated in FIG. 10D orthogonal to the plane of the support frame 81, 82, 83 can be about equal to the height of the cross section of the rectangle illustrated in FIG. 10B. Alternatively, the height of the narrower section II-II can be greater than the height of the wider section I-I. Areas of the respective support frame 81, 82, 83 having a cross section as illustrated in FIG. 10D have a higher flexibility in the plane of the respective support frame compared to areas of the respective support frame having a cross section as illustrated in FIG. 10B. In some examples, the cross section is approximately square shaped having an edge length of about 0.008 inches (0.2 millimeters).

A support frame 81, 82, 83 including rectangular cross sections illustrated in FIGS. 10B and 10D can be formed by selecting a sheet having a thickness about equal to the height of the cross sectional shapes illustrated in FIGS. 10B and 10D and cutting the sheet to the shape of each respective support frame 81, 82, 83 as illustrating in FIG. 10A, varying the width of each segment of each support frame 81, 82, 83 to be wider in regions indicated by the Roman Numerals I-I and narrower in regions indicated by Roman Numerals II-II. Alternatively, the support frame 81, 82, 83 can be formed by selecting square or rectangular wire, shaping the wire to form a looped path, and flattening the wire to have regions with wider cross sections I-I and narrower cross sections II-II.

FIG. 10E shows an alternative cross section corresponding to sections of each support frame 81, 82, 83 annotated with Roman Numerals II-II. The cross section has an ovoid or oval-shaped shape that is shorter in the plane of the respective support frame 81, 82, 83 compared to the width of the oval cross section illustrated in FIG. 10C. The height of the cross section illustrated in FIG. 10E orthogonal to the plane of the support frame 81, 82, 83 can be greater than the height of the cross section of the oval illustrated in FIG. 10C. Areas of the respective support frame 81, 82, 83 having a cross section as illustrated in FIG. 10E have a higher flexibility in the plane of the respective support frame compared to areas of the respective support frame having a cross section as illustrated in FIG. 10C. In some examples, the cross section is approximately circular having a diameter of about 0.008 inches (0.2 millimeters).

A support frame 81, 82, 83 including ovoid or oval-shaped cross sections illustrated in FIGS. 10C and 10E can be formed by selecting a round or oval wire, shaping the wire to form a looped path, and flattening the wire to have regions with wider cross sections I-I and narrower cross sections II-II.

Referring collectively to FIGS. 10A through 10E, the end effector 100 can include a support frame assembly 80c having some or all of the cross sections illustrated in FIGS. 10B through 10E in any combination. Further, each support frame 81, 82, 83 can individually include some or all of the cross sections illustrated in FIG. 10B through 10E in any combination. The effector 100 can additionally, or alternatively include cross sections not illustrated herein to achieve a difference in flexibility between regions indicated by Roman Numerals I-I and regions indicated by Roman Numerals II-II as understood by a person skilled in the pertinent art according to the teachings herein. Preferably, for the sake of manufacturability, individual support frames 81, 82, 83 can include primarily rectangular cross sectional shapes (e.g. FIGS. 10B and 10D) or primarily ovoid shapes (e.g. FIGS. 10C and 10E) as combining rectangular shapes with ovoid shapes in the same support frame 81, 82, 83 can increase cost and/or difficulty in manufacturing.

FIGS. 10F and 10G are illustrations of possible transition schemes (knuckles) between regions of a support frame of the end effector. As illustrated in FIG. 10F, the support frame can transition asymmetrically in width from a wider cross section I-I to a narrower cross section II-II and vice versa. As illustrated in FIG. 10G, the support frame can transition symmetrically in width from a wider cross section I-I to a narrower cross section II-II and vice versa. The support frame can include only asymmetrical transitions in width, only symmetrical transitions in width, or a mix of asymmetrical and symmetrical transitions in width. Such transitions can be applied to any of the example support members illustrated and otherwise described herein.

FIG. 11A is an illustration of an asymmetrical support frame 181 of the end effector 100. FIGS. 11B and 11C are illustrations of cross sections of the asymmetrical support frame 181 as indicated in FIG. 11A. The asymmetrical support frame 181 is another example support frame that can be used in place of the outer support frames 81, 83 illustrated and described elsewhere herein (e.g. in relation to FIGS. 8A through 8D). FIG. 12A is an illustration of a symmetrical support frame 182 of the end effector 100. The symmetrical support frame 182 is another example support frame that can be used in place of the central support frame 82 illustrated and described elsewhere herein (e.g. in relation to FIGS. 8A through 8D). FIGS. 12B and 12C are illustrations of cross sections of the symmetrical support frame as indicated in FIG. 12A. FIG. 12D is an illustration of a detailed section of the symmetrical support frame as indicated in FIG. 12A. In some examples, the support frame assembly 80 can include two asymmetrical support frames 181 and a single symmetrical support frame 182.

FIG. 11A illustrates that the parallel segments 81A, 81B of the asymmetric support frame 181 can have a wider cross section I-I as illustrated in FIG. 11C compared to the narrower cross section II-II of the connecting segment 81C as illustrated in FIG. 11B. In some examples, the cross sectional shape of the parallel segments 81A, 81B can be substantially rectangular with a width in the plane of the support frame 181 of about 0.013 inches (0.33 millimeters) and a height orthogonal to the plane of the support frame 181 of about 0.005 inches (0.13 millimeters). In some examples, the cross sectional shape of the connecting segment 81C can be substantially rectangular or square with a width in the plane of the support frame 181 of about 0.008 inches (0.2 millimeters) and a height orthogonal to the plane of the support frame 181 of about 0.008 inches (0.2 millimeters). Further, the proximal segments 81E, 81D can have a cross section I-I of approximately the same dimensions as the parallel segments 81A, 81B.

FIG. 12A illustrates that a majority of the length of the parallel segments 82A, 82B of the symmetric support frame 182 can have a wider cross section I-I as illustrated in FIG. 12C compared to the narrower cross section II-II of the connecting segment 82C. The parallel segments 82A, 82B can include a tapering transition as illustrated in FIG. 12D and indicated in FIG. 12A that tapers from the wider width of the wider cross section I-I to the narrower width II-II of the narrower cross section II-II. A distal portion of each parallel segment 82A, 82B distal to the tapering transition can have the narrower cross section I-I. The proximal segments 82E, 83D can have a cross section I-I of approximately the same dimensions as the majority of the length of the parallel segments 82A, 82B. The symmetric support frame 182 can further include a narrower width sections 82F, 82G that respectively include a proximal portion of a respective parallel segment 82A, 82B and a distal portion of a respective proximal segment 82D, 82E. These narrower width sections 82F, 82G can have a cross section II-II as illustrated in FIG. 12B. These narrower width sections 82F, 82G can have a length of approximately 0.102 inches (2.6 millimeters). The symmetric support frame 82 can have a width of approximately 0.294 inches (7.5 millimeters) as measured between outer edges of the parallel segments 82A, 82B in the plane of the support frame 82 as illustrated.

As illustrated in FIG. 12B, in some examples, the narrower cross sectional regions II-II can have a cross sectional shape that is substantially rectangular or square with a width in the plane of the support frame 182 of about 0.005 inches (0.13 millimeters) and a height orthogonal to the plane of the support frame 182 of about 0.005 inches (0.13 millimeters).

As illustrated in FIG. 12C, in some examples, the wider cross sectional regions I-I can have a substantially rectangular cross sectional shape with a width in the plane of the support frame 182 of about 0.01 inches (0.25 millimeters) and a height orthogonal to the plane of the support frame 182 of about 0.005 inches (0.13 millimeters).

FIG. 13A is an illustration of an asymmetrical support frame 281 of the end effector 100. FIGS. 13B and 13C are illustrations of cross sections of the asymmetrical support frame 281 as indicated in FIG. 13A. The asymmetrical support frame 281 is another example support frame that can be used in place of the outer support frames 81, 83 illustrated and described elsewhere herein (e.g. in relation to FIGS. 8A through 8D). FIGS. 13D and 13E are illustrations of detailed sections of the asymmetrical support frame 281 as indicated in FIG. 13A. FIG. 14A is an illustration of a symmetrical support frame 282 of the end effector 100. The symmetrical support frame 282 is another example support frame that can be used in place of the central support frame 82 illustrated and described elsewhere herein (e.g. in relation to FIGS. 8A through 8D). FIGS. 14B and 14C are illustrations of cross sections of the symmetrical support frame as indicated in FIG. 14A. FIGS. 14D and 14E are illustrations of a detailed section of the symmetrical support frame as indicated in FIG. 14A. In some examples, the support frame assembly 80 can include two asymmetrical support frames 281 and a single symmetrical support frame 282.

FIG. 13A illustrates that the parallel segments 81A, 81B of the asymmetric support frame 281 can have a wider cross section I-I as illustrated in FIG. 13B compared to the narrower cross section II-II of the connecting segment 81C. In some examples, the cross sectional shape of the parallel segments 81A, 81B can be substantially rectangular with a width in the plane of the support frame 281 of about 0.01 inches (0.25 millimeters) and a height orthogonal to the plane of the support frame 281 of about 0.007 inches (0.18 millimeters). In some examples, the cross sectional shape of the connecting segment 81C, at least in the area indicated by section A-A in FIG. 13A, can be substantially square with a width in the plane of the support frame 281 less than the width of the cross section of the parallel segments 81B, 81A. The cross section I-I can have a width of about 0.005 to about 0.007 inches (about 0.13 to 0.18 millimeters). The cross section I-I can have a height of about 0.007 inches (about 0.18 millimeters). Further, the proximal segments 81E, 81D can have a cross section I-I of approximately the same dimensions as the parallel segments 81A, 81B. A length L1 of the frame 81B as measured from a distal end to the proximal end (indicated as "y" in FIG. 13A) can be approximately 1.4 inches (or 36 mm) and a width W1 as measured from frame 81A to frame 81B is approximately 0.29 inches (or 7.4 mm).

FIG. 13D illustrates transition, on the connector segment 81C between the wider cross section I-I illustrated in FIG. 13D and the narrower cross section II-II illustrated in FIG. 13C.

FIG. 13E illustrates a serrated segment of the support frame 281 shaped to secure the two ends of the loop member to the distal portion of the shaft 9 or connector tubing 46.

FIG. 14A illustrates that a majority of the length of the parallel segments 82A, 82B of the symmetric support frame 282 can have a wider cross section I-I as illustrated in FIG. 14C compared to the narrower cross section II-II of the connecting segment 82C as illustrated in FIG. 14B. The parallel segments 82A, 82B can include a tapering transition as illustrated in FIG. 14D and indicated in FIG. 14A that tapers from the wider width of the wider cross section I-I to the narrower width II-II of the narrower cross section II-II. FIG. 14E illustrates a serrated segments of the support frame 282 shaped to secure the two ends of the loop member to the distal portion of the shaft. We have devised a configuration of the support frame in FIG. 14A (as well as FIG. 13A) such that an aspect ratio of the length L1 to width W1 (i.e., L1/W1) may be from 4 to 5. In the preferred embodiments, the aspect ratio (L1/W1) of the frame support of FIGS. 13A and 14A is one of 4.5 or 4.75.

As illustrated in FIG. 14B, in some examples, the narrower cross sectional regions II-II can have a cross sectional shape that is substantially rectangular with a width in the plane of the support frame 282 of about 0.005 inches (0.13 millimeters) and a height orthogonal to the plane of the support frame 282 of about 0.007 inches (0.18 millimeters).

As illustrated in FIG. 14C, in some examples, the wider cross sectional regions I-I can have a substantially rectangular cross sectional shape with a width in the plane of the support frame 282 of about 0.01 inches (0.25 millimeters) and a height orthogonal to the plane of the support frame 282 of about 0.005 inches (0.13 millimeters).

Figure 15:
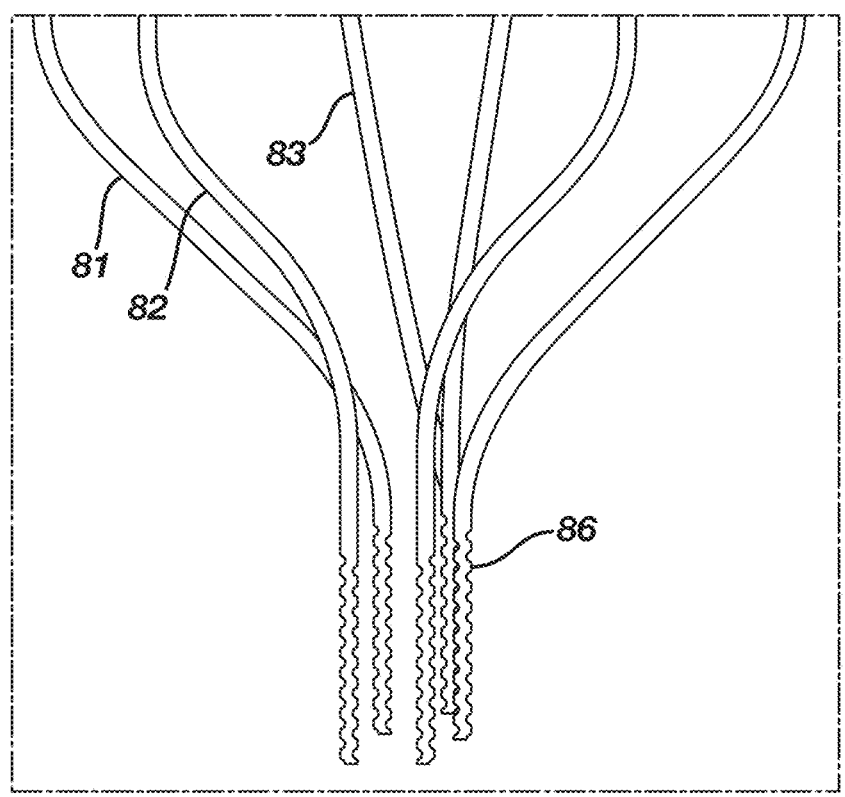
FIG. 15 is an illustration of crimped or serrated features at end of the support frames according to aspects of the present invention.

FIG. 15 is an illustration of crimped or serrated features 86 at ends of the support frames. The crimped or serrated features 86 can facilitate engagement of the support frames 81, 82, 83 to the distal end 14A of the shaft 9 (e.g. within the connector tubing 46). In particular, the serrations 86 of each support frame can be molded together with the connector tubing 46 or affixed (e.g., adhesive or epoxy) with the connector tubing 46. To ensure that each loop frame is structurally rigid where the loop comes out of the tubing 46, each serration 86 of each support frame are affixed directly to the tubing 46 and one serration 86 does not engage or mate with another serration 86 from another support member. This ensures that forces transmitted to frame 81 from the loop distal end are not transmitted to itself via the serrations or to other frames 82 and 83 due to the serrations 86 being independently affixed to the tubing 46 instead of other serrations 86.

FIGS. 16A through 16D are illustrations of deformation of support frame assemblies as a result of application of various forces. Each support frame assembly 80 includes a first support frame 81, a second support frame 82, and a third support frame 83. The first and third support frames 81, 83 are outer support frames surrounding the second central support frame 82. The support frame assembly 80 includes a mechanical linkage 50 joining the first, second, and third support frames 81, 82, 83 at the distal vertex.

Figure 16A:
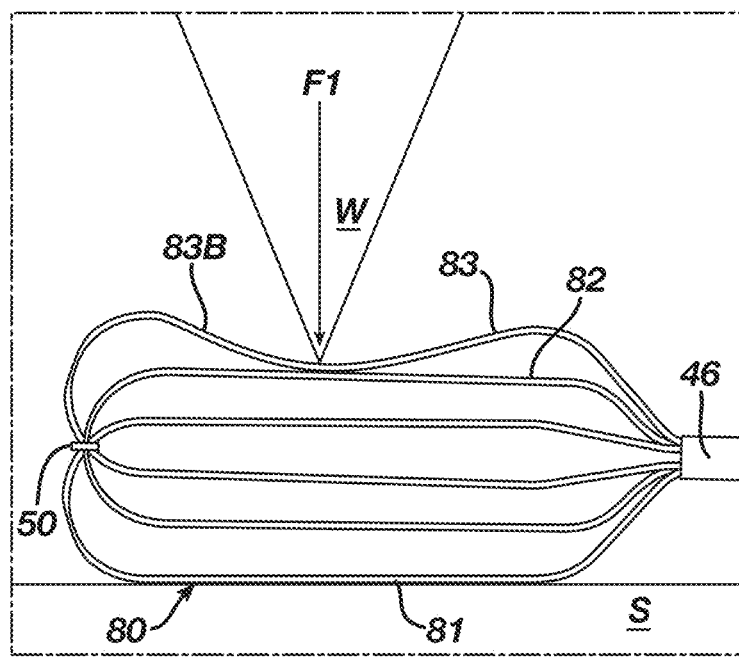

FIG. 16A illustrates the first support frame 81 pressed into a planar surface S as an apex of a wedge W is pressed with a force F1 into the third support frame 83. The support frame assembly 80 is aligned approximately orthogonal to the planar surface S. The force F1 is applied approximately orthogonal to, and in a direction toward the planar surface S. The force F1 is applied centrally along the length of the outer parallel segment 83B of the third support frame 83. The outer parallel segment 83B of the third support frame bows toward the surface S as a result of the force F1. The support frame assembly 80 can be configured to resist spine-to-spine contact when the force F1 is applied. In FIG. 16A, the outer parallel segment 83B of the third support frame is bowed to contact the second support frame 82. The force F1 sufficient to move the outer parallel segment 83B of the third support frame 83 into contact with the second support frame 82 can be a metric used to compare variations in support frame assembly design (e.g. with differing support frame cross section design) where a higher force F1 indicates a more favorable result for this test.

Figure 16B:
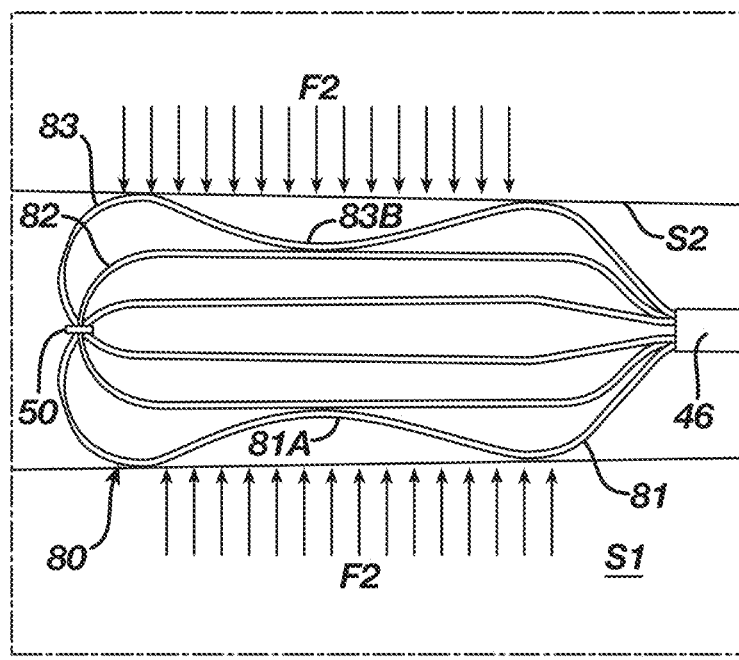

FIG. 16B illustrates the support frame assembly 80 compressed between two planar surfaces S1, S2 with a force F2.

The planar surfaces S1, S2 are aligned approximately parallel to each other. The support frame assembly 80 is aligned approximately orthogonal to the planar surfaces S1, S2. An outer parallel segment 81A of the first support frame 81 is pressed by the first planar surface 51. The outer parallel segment 83B of the third support frame 83 is pressed by the second planar surface S2. As a result of the compression by the force F2 between the planar surfaces S1, S2, the outer parallel segments 81A, 83B bow toward the opposite planar surface S1, S2. The support frame assembly 80 can be configured to resist spine-to-spine contact when the force F2 is applied. The force F2 sufficient to move the outer parallel segment 83B of the third support frame 83 or the outer parallel segment 81A of the first support frame 81 into contact with the second support frame 82 can be a metric used to compare variations in support frame assembly design (e.g. with differing support frame cross section design) where a higher force F2 indicates a more favorable result for this test. In the preferred embodiments, F1 or F2 is approximately 10 gram-force or greater. The range of suitable force is about 10 gram-force to 50 gram-force for F1 and 10 gram-force to 70 gram-force.

FIG. 16C illustrates the support frame assembly 80 compressed by a planar surface S applying a force F3 to a distal end of the support frame assembly 80. The distal portion 14A of the shaft 9 is held at a position in the proximal direction of the connector tubing 46 such that the longitudinal axis L-L defined by the shaft 9 is approximately orthogonal to the surface S. The force F3 is applied to the connector segments 81C, 83C of the first and third support frames 81, 83. As a result of the compression by the force F3 in the direction of the longitudinal axis L-L, the support frame assembly 80 and connector tubing 46 deflect out of alignment with the longitudinal axis L-L. This is to ensure the distal section 14A of shaft 9 and/or end effector are sufficiently flexible so that the end effector and/or distal section of the shaft buckles at a sufficiently low force when applied to a heart wall to inhibit the end effector from puncturing the heart wall.

FIG. 16D illustrates the support frame assembly 80 deflected by a force F4 applied approximately orthogonal to the support frame assembly near the mechanical linkage 50 at the distal vertex. The distal portion 14A of the shaft 9 is held near the connector tubing 46. As a result of the force F4, the support frame 80 is deflected out of alignment with the longitudinal axis L-L. In some use cases, it can be desired to have a greater or lesser deflection as a result of Force F4 depending on the geometry of a treatment area and/or preferences of a physician regarding tactile feedback.

FIGS. 17A through 17D are illustrations of an example rectangular or ovular mechanical linkage 50a having a closable single opening and used for joining the loop members according to aspects of the present invention. Alternative mechanical linkages 50b-h are illustrated in FIGS. 18A through 22C. The linkages 50a-h can be used to join loop members (or other electrode carrying structures) of catheter-based devices similar to how the loop members 1, 2, 3 are joined at the distal vertex as described and illustrated herein. The mechanical linkage can serve to inhibit electrodes 37 on the spines 1A, 2A, 3A, 1B, 2B, 3B of the end effector 100 from coming into contact with each other. Loop members 1, 2, 3 are spatially affixed relative to each other by the connector tubing 46 near the proximal end of the end effector 100. Without the mechanical linkage, the distal ends of the respective loop members 1, 2, 3 are free to move in relation to each other when acted on by a force such as the forces F1, F2, F3, F4 illustrated in FIGS. 16A through 16D.

The mechanical linkage is sized, shaped, and otherwise configured to allow the end effector 100 to be collapsed for delivery through a catheter or guiding sheath to a treatment site. Ease of assembly of the end effector 100 is also a design consideration for the mechanical linkage.

Figure 17A:
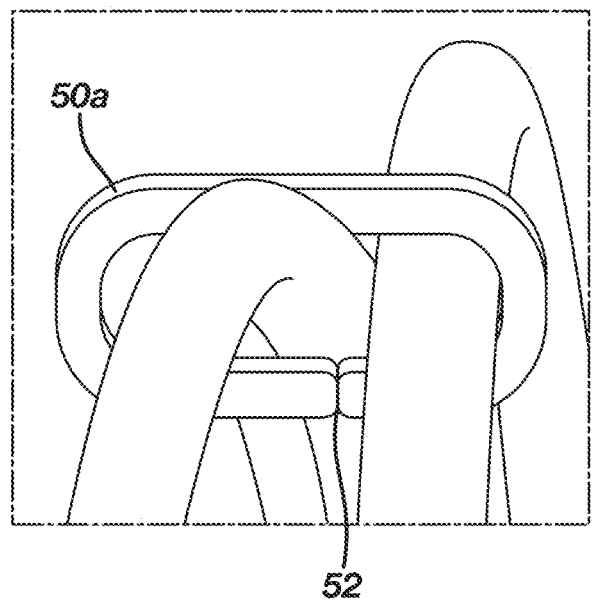
FIGS. 17A through 17D are illustrations of an example rectangular or ovular mechanical linkage having a closable single opening and used for joining the loop members according to aspects of the present invention.
Figure 17B:
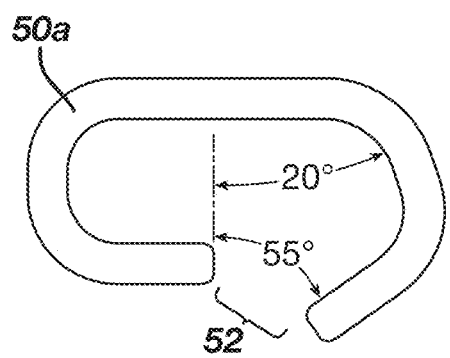
Figure 17C:
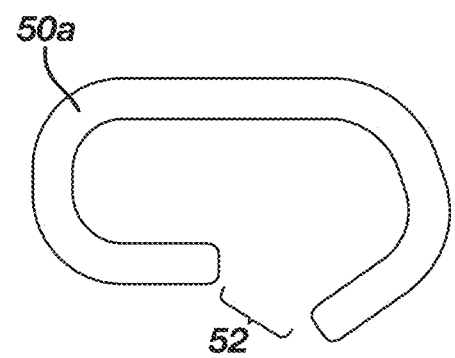
Figure 17D:
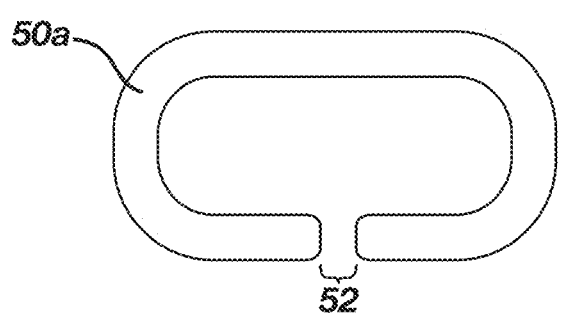

FIG. 17A illustrates the mechanical linkage 50a joining three loop members 1, 2, 3. The mechanical linkage 50a includes a seam or gap 52. FIGS. 17B and 17C illustrate the mechanical linkage 50a as manufactured. The linkage 50a is initially formed as an open clip. A stiff material, preferably metal, is formed or cut into a shape resembling an open paper clip. The individual loop members 1, 2, 3 can be constructed prior to being joined by the mechanical linkage 50a. In some example methods of construction, the end effector 100 can be entirely contracted and affixed to the shaft 9 before the linkage 50a is affixed to the loop members 1, 2, 3. The linkage 50a can include an opening 52 sized to allow loop members 1, 2, 3, one at a time, to be inserted into the linkage 50a. The opening 52 as manufactured can be larger than respective diameters of the loop members 1, 2, 3 near the distal vertex. Once the loop members 1, 2, 3 are inserted into the linkage 50a, the opening 52 can be collapsed as illustrated in FIG. 17D. The opening 52 can be collapsed by crimping a free open end of the linkage 50a until it lines up with the other open end of the linkage 50a. When the opening is collapsed, a short side of the linkage 50a can be moved through an angle of about 20° and the free open end on a long side of the linkage 50a can be moved through an angle of about 59° as illustrated in FIG. 17B.

The mechanical linkage 50a illustrated in FIGS. 17A through 17D is symmetrical. Alternatively, the mechanical linkage 50a can be asymmetrical to promote consistent collapsing geometry of the end effector for delivery through a catheter.

Figure 18A:
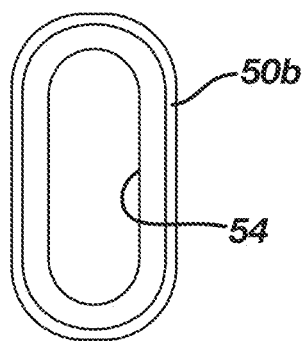
FIGS. 18A through 18C are illustrations of an example rectangular or ovular mechanical linkage having a single opening and used for joining the loop members according to aspects of the present invention.
Figure 18B:
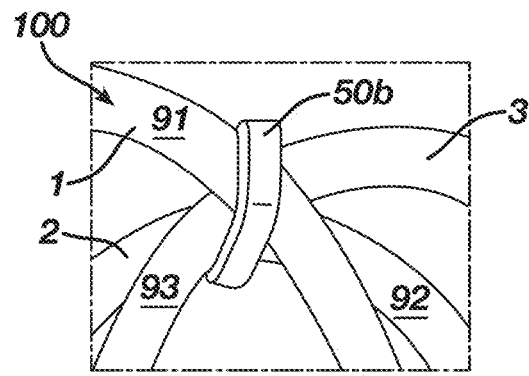
Figure 18C:
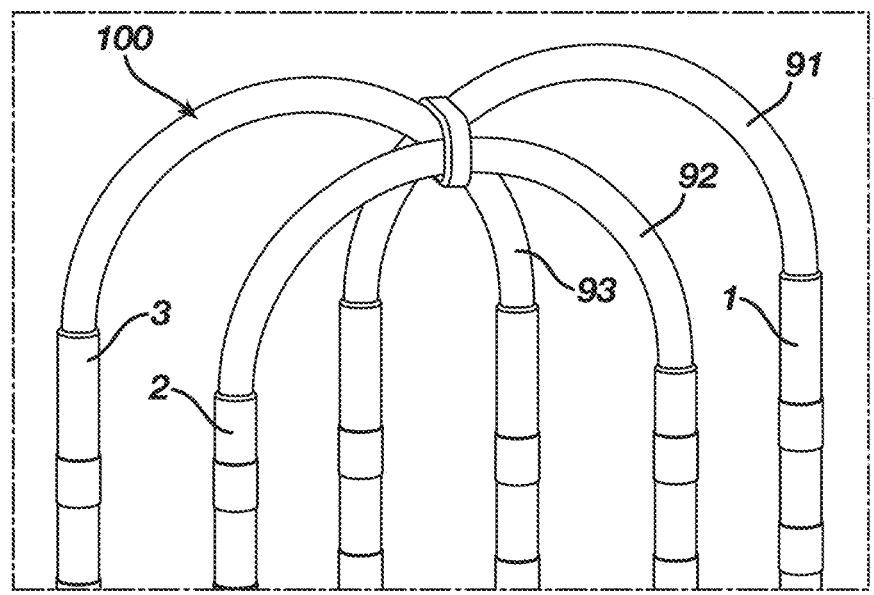

FIGS. 18A through 18C are illustrations of an example rectangular or ovular mechanical linkage 50b having a single opening and used for joining the loop members 1, 2, 3. The example mechanical linkage 50b has four contiguous sides. Compared to the example mechanical linkage 50a illustrated in FIGS. 17A through 17D, the example mechanical linkage 50b in FIGS. 18A through 18C lacks a gap or seam 52. During assembly, loop members 1, 2, 3 can be fed through the opening 54 of the linkage 50b before the ends of the loop members 1, 2, 3 are affixed to the shaft 9.

The mechanical linkage 50b illustrated in FIGS. 18A through 18C is symmetrical. Alternatively, one side of the ring can be wider than the other to promote the loop members 1, 2, 3 to fold to a particular side when the end effector 100 is collapsed for delivery through a catheter or guiding sheath.

Figure 19A:
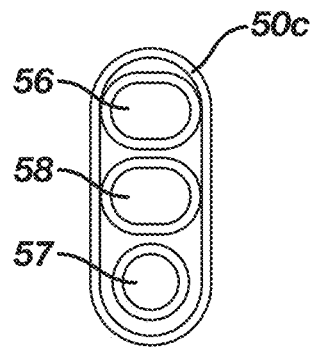
FIGS. 19A through 19C are illustrations of an example rectangular or ovular mechanical linkage having three openings and used for joining the loop members according to aspects of the present invention.
Figure 19B:
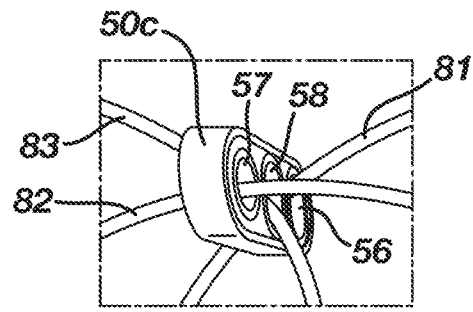
Figure 19C:
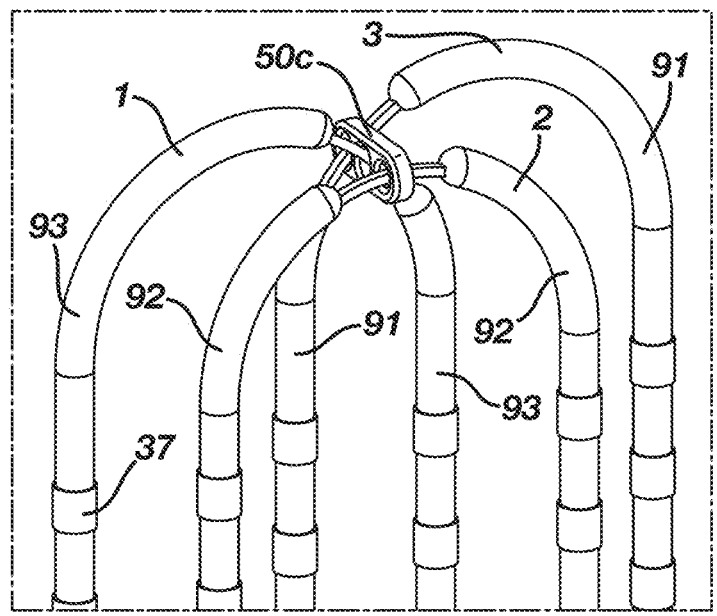

FIGS. 19A through 19C are illustrations of an example rectangular or ovular mechanical linkage 50c having three openings 56, 57, 58 and used for joining the loop members 1, 2, 3. Each opening 56, 57, 58 can be shaped and otherwise configured to receive a loop member 1, 2, 3.

The linkage 50c can include a circular opening 57 to receive the central, symmetric loop member 2. The central loop member 2 can be approximately orthogonal to the linkage 50c at the distal vertex, allowing for the respective opening 57 of the linkage 50c to be circular. The linkage 50c can include two oblong openings 58, 56 each respectively shaped to receive a respective outer, asymmetrical loop member 1, 3. The outer loop members 1, 3 can pass through the linkage 50c at a non-orthogonal angle. The oblong shape of the corresponding linkage openings 56, 58 can be elongated to account for non-orthogonal trajectory of the outer loop members 1, 3 through the linkage 50c.

Each of the loop members 1, 2, 3 can include a respective tubular housing 91, 92, 93 covering a majority of the support frame 81, 82, 83 for that loop member 1, 2, 3. To reduce the separation of the support frames 81, 82, 83 at the distal vertex, the loop members 1, 2, 3 need not include tubular housing 91, 92, 93 near the distal vertex. The openings 56, 57, 58 of the linkage 50c can be sized to allow the support frame 81, 82, 83 of the loop members to pass through, but need not be sized to allow the tubular housings 91, 92, 93 to pass through. During assembly, the support frames 81, 82, 83 can be positioned through the openings 56, 57, 58 of the linkage 50c before the tubular housings 91, 92, 93 are added to the loop members 1, 2, 3.

Alternatively, the openings 56, 57, 58 can be sized to allow the tubular housings 91, 92, 93 of the loop members 1, 2, 3 to pass therethrough to allow for a design where some or all of the tubular housings 91, 92, 93 cross the distal vertex and/or to allow for an assembly process where the tubular housings 91, 92, 93 are affixed to the loop members 1, 2, 3 before the mechanical linkage 50c.

FIGS. 20A through 20C are illustrations of an example cylindrical mechanical linkage 50d having three passageways 60, 62, 64 and used for joining support members 81, 82, 83 of the loop members 1, 2, 3. The openings 60, 62, 64 of the linkage 50d can be sized to allow the support frame 81, 82, 83 of the loop members to pass through, but need not be sized to allow the tubular housings 91, 92, 93 to pass through. During assembly, the support frames 81, 82, 83 can be positioned through the openings 60, 62, 64 of the linkage 50d before the tubular housings 91, 92, 93 are added to the loop members 1, 2, 3.

FIGS. 21A through 21C are illustrations of an example cylindrical mechanical linkage 50e having three passageways 66, 68, 70 and used for joining the loop members 1, 2, 3 with tubular housings 91, 92, 93 over the support members 81, 82, 83. In some examples, the passageways 66, 68, 70 can be sized to allow for an assembly process where the tubular housings 91, 92, 93 are affixed to the loop members 1, 2, 3 before the mechanical linkage 50e.

Figure 22A:
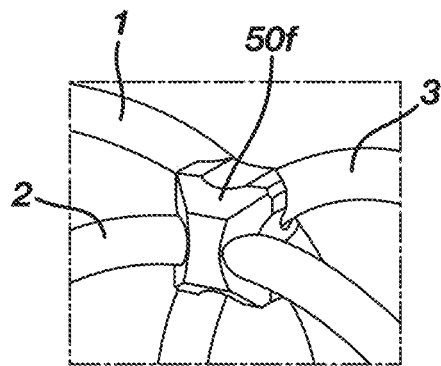
FIGS. 22A through 22C are illustrations of example mechanical linkages according to aspects of the present invention.
Figure 22B:
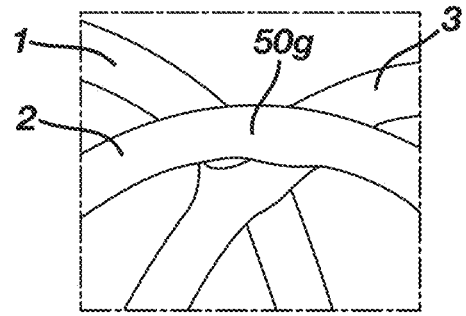
Figure 22C:
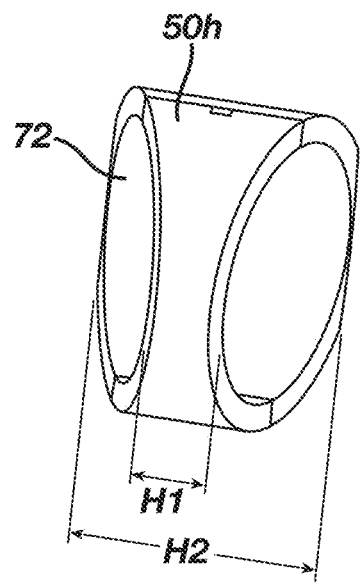

FIGS. 22A through 22C are illustrations of additional example mechanical linkages. FIG. 22A illustrates a mechanical linkage 50f including polymer shaped to closely conform to the dimensions of the loop members 1, 2, 3. The linkage 50f can include an adhesive. The linkage 50f can be applied by hand, over molded, or by other means as understood by a person skilled in the pertinent art. FIG. 22B illustrates a mechanical linkage 50g including an adhesive. FIG. 22C illustrates a tapered ring linkage 50h having an annular opening 72 through which the three loop members 1, 2, 3 can extend and a height that tapers from a larger dimension H2 to a smaller dimension H1 across the diameter of the opening 72. The link 50h has a portion on one side that is narrower on one side (H1) as compared to the portion H2 on the other side. The narrowed portion H1 encourages the loops 1, 2 and 3 to bend toward the narrowed side when retracting into the sheath. This can be used to reduce forces required for sheath retraction.

Figure 23A:
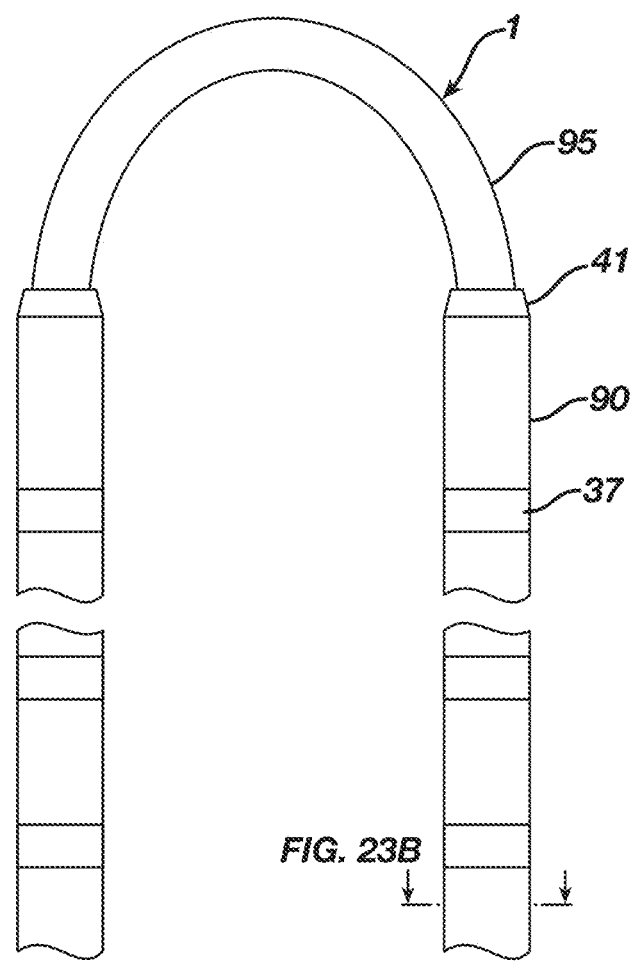
FIGS. 23A and 23B are illustrations of an example loop member having an inner and outer housing surrounding the support frame according to aspects of the present invention.
Figure 23B:
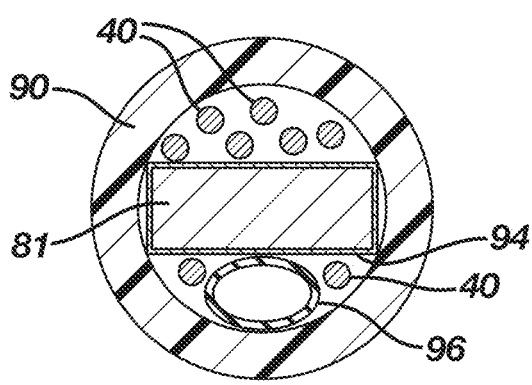

FIGS. 23A and 23B are illustrations of an example loop member 1 having an inner housing 94 and outer housing 90 surrounding the support frame 81. The illustrated loop member 1 can be used in place of loop members 1, 2, 3 illustrated and otherwise disclosed herein according to the teachings herein. In particular, it can be advantageous to use the illustrated loop member in place of loop members 1, 2, 3 illustrated in FIGS. 19C and 20C. The inner housing 94 and outer housing 90 can collectively function as the tubular housing 91, 92, 93 illustrated elsewhere herein.

The outer housing 90 can include polymeric tube (e.g. thermoplastic polyurethane) having a single lumen sized to house the support frame 80 and wires 40 that provide electrical connections to the end effector electrodes 37. The lumen of the outer housing 90 can also be sized to house an irrigation tube 96 having an irrigation lumen therethrough. In this configuration, the support frame is surrounded by a sleeve to isolate its edges from damaging the conductors. The support frame, sleeve and conductors are in one lumen, shown in FIG. 23B (whereby irrigation is optional). A small diameter tube 95 in FIG. 23A is a separate piece that is bonded to the larger tube, with the purpose of reducing the outer diameter when passing through the mechanical linkage.

The inner housing 94 (FIG. 23B) can be shaped, sized, and otherwise configured to closely surround the support frame 81. The inner housing 94 can include a polymeric material, for example a shrink sleeve applied during a reflow process. Because neither the wires 40 nor the irrigation tube 96 need extend beyond the spines of the loop member, the outer housing 90 need not cover the connector segment of the loop member. The inner housing 94 can be dimensioned to allow less separation between the loop members 1, 2, 3 near the distal vertex compared to a loop member having a tubular housing dimensioned similar to the outer housing 90 crossing, or extending near, the distal vertex. Further, the distal end of the end effector 100 can collapse to a smaller dimension compared to an end effector having a tubular housing dimensioned similar to the outer housing 90 crossing, or extending near, the distal vertex.

Within the outer housing 90, the inner housing 94 can be bonded to the outer housing 90. The bond between the inner housing 94 and outer housing 90 can inhibit fluid leakage. The bond between the inner housing 94 and outer housing 90 can promote conformity of the shape of the outer housing 90 to that of the support frame 81 inhibiting shifting of the support frame 81 within the outer housing 90 when the end effector 100 is deformed from its unconstrained configuration.

At the distal ends of the outer housing 90, the loop member 1 can include a joint 41 configured to inhibit fluid ingress into the outer housing 90. The joint 41 can be bonded to the outer housing 90 and inner housing 94.

Figure 24A:
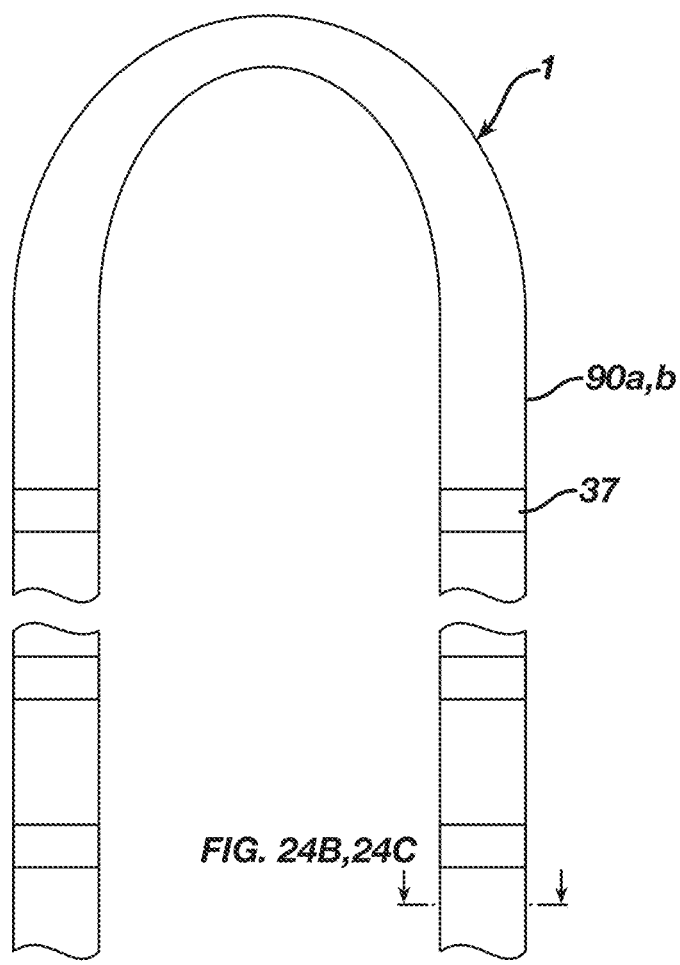
FIGS. 24A through 24C are illustrations of an alternative example loop member having a tubular housing having two or three lumens therethrough in which the support frame, conductive wires, and an irrigation tube are positioned according to aspects of the present invention.
Figure 24B:
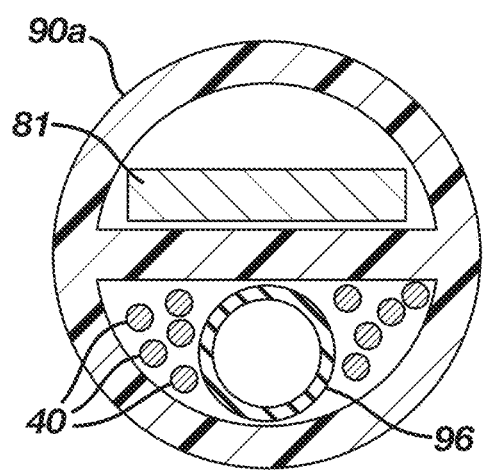
Figure 24C:
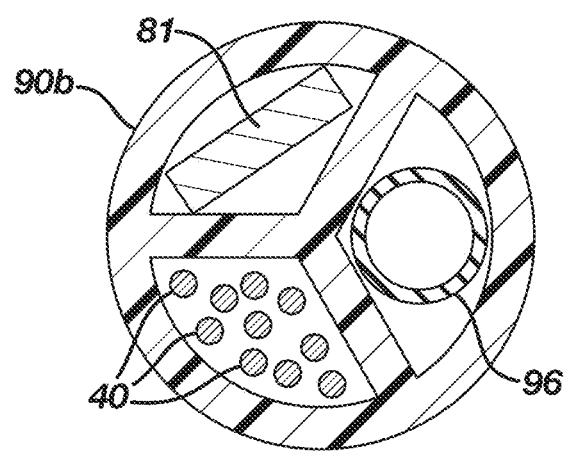

FIGS. 24A through 24C are illustrations of an alternative example loop member having a tubular housing 90a, 90b having two lumens 90a or three lumens 90b therethrough in which the support frame 81, conductive wires 40, and an irrigation tube 96 are positioned. Regardless of whether the tubular housing 90a, 90b has two or three lumens, the loop member can have an outer appearance similar to as illustrated in FIG. 24A. FIG. 24B illustrates a cross section of the loop member having a tubular housing 90a with two lumens. The design purpose of the embodiment in FIG. 24B is to isolate the support member from damaging the conductors or irrigation lines. FIG. 24C illustrates a cross section of the loop member having a tubular housing 90b with three lumens. The cross sections illustrated in FIGS. 24B and 24C are viewed along a spine of the loop member as indicated in FIG. 24A.

FIG. 24B illustrates the support frame 81 positioned in one lumen of the dual lumen tubular housing 90a and the wires 40 and irrigation tube 96 positioned in the other lumen of the dual lumen tubular housing 90b. Separation of the support frame 81 from the wires 40 and irrigation tube 96 can inhibit edges of the support frame 81 from abating insulation the wires 40 or walls of the irrigation tube 96. The dual lumen tubular housing 90b can be used in place of tubular housings 91, 92, 93 illustrated elsewhere herein.

FIG. 24C illustrates the support frame 81 positioned in a first lumen of the tri lumen tubular housing 90b, wires 40 in a second lumen of the tri lumen tubular housing 90b, and an irrigation tube 96 in a third lumen of the tri lumen tubular housing 90b. The tri lumen tubular housing 90c can be used in place of tubular housings 91, 92, 93 illustrated elsewhere herein. The purpose of this design in FIG. 24C is to isolate the irrigation line 96 from contact with the other materials. As an alternative to the illustration of FIG. 24C, the loop member 1 need not include an irrigation tube 96, and the lumen of the tubular housing 90b in which the irrigation tube 96 is illustrated can be used direction for irrigation.

Spine covers 90, 90a, 90b can be preferably 3 French to 2 French. In some examples, the spine cover 90 illustrated in FIGS. 23A and 23B, compared to the spine covers 90a, 90b illustrated in FIGS. 24A through 24B, can have more usable interior space for the same French sizing, allowing for a larger support frame, larger irrigation tube 96, and/or increased volume of wires 40.

FIGS. 25A through 25F are illustration of example end effector electrodes 37 with varying degrees of surface roughness. Contact resistance between an electrode and tissue is inversely proportionate to the surface area of the electrode in contact with the tissue. In other words, electrical energy is transferred more efficiently from the electrode to the tissue and vice versa when contact area between the electrode and tissue is increased. For diagnostic measurements, more efficient electrical energy transfer from tissue to electrode results in clearer, less noisy, more accurate electrical signals (sensor measurements). Dimensions of the footprint, or perimeter, of the electrode is limited by the geometry of the vasculature through which the end effector 100 travels to reach a treatment site, the geometry of the treatment site, and the geometry of other components of the end effector 100. Micro-roughness on the electrode surface increases effective surface area of the electrode, thereby reducing contact resistance when the electrode surface is pressed to tissue, without increasing the footprint of the electrode. However, increasing surface roughness can also promote thrombus formation on the electrode which can lead to complications during treatment.

Figure 25A:
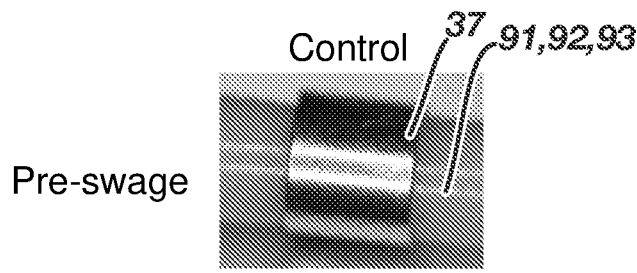
FIGS. 25A through 25F are illustration of example end effector electrodes with roughened surfaces according to aspects of the present invention.
Figure 25C:
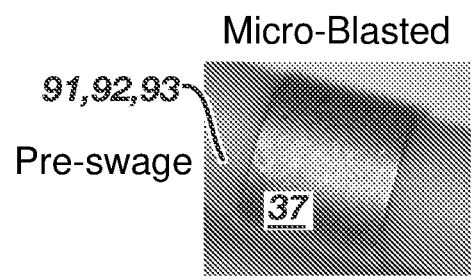
Figure 25B:
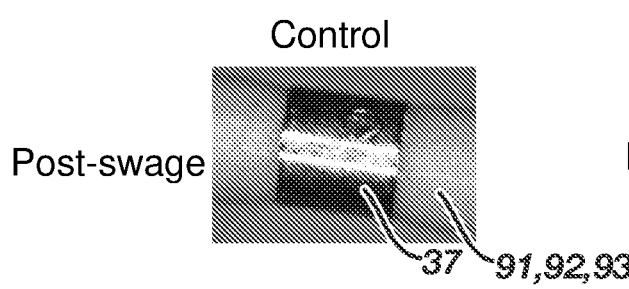
Figure 25D:
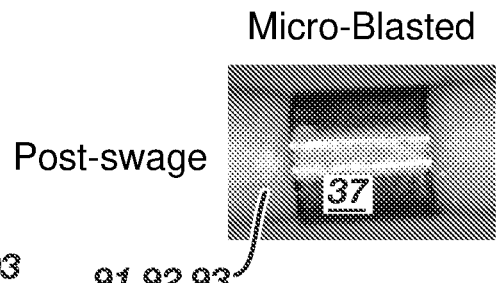

FIG. 25A illustrates a control electrode 37 with an untreated surface. FIG. 25B illustrates an electrode 37 compacted from a swaging process. The compacted electrode is compressed to have an outer circumference that approximates the outer circumference of the tubular housing 91, 92, 93. FIG. 25C illustrates a micro-blasted electrode 37 that is not swaged. Micro-blasting introduces surface roughness on a micrometer scale. The surface can alternatively be roughed by other suitable process such as chemical etching, sputtering, and/or other deposition method. FIG. 25D illustrates a micro-blasted and swaged electrode 37.

The combination of roughening (e.g. micro-blasting) and swaging the electrode surface creates a controlled, shallow surface roughness. Swaging reduces the ring diameter of the electrode 37 and can also flatten some vertical features created from roughening, resulting in an electrode with a higher surface area and relatively flattened outer surface. The higher surface area can be effective to reduce contact resistance between an electrode and tissue.

Figure 25E:
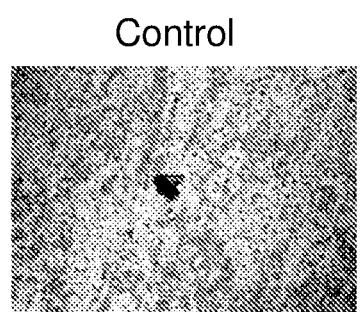
Figure 25F:
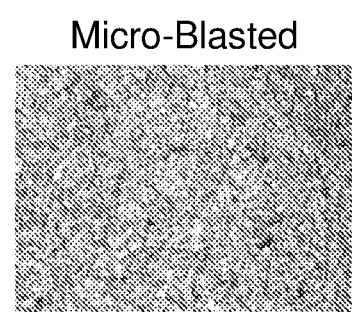

Surface roughness can be characterized by roughness parameter Ra representing an arithmetical mean deviation of a profile of the surface. As illustrated in FIG. 25F, in some examples, some or all of the electrodes 37 of the end effector 100 can have a surface roughness parameter Ra measuring from about 0.3 micrometers to about 0.4 micrometers. This surface roughness can be effective to increase surface area of the electrodes 37 to decrease contact resistance to tissue while not significantly promoting thrombus formation. In comparison, as illustrated in FIG. 25E, the untreated surface can have a surface roughness parameter Ra measuring from about 0.1 micrometers to about 0.2 micrometers.

During manipulation of the apparatus (e.g. pressing to a surface and/or deflection of the intermediate section 14) wires 40 carrying electrical signals of the end effector electrodes 37 can shift and vibrate. This vibration can cause noise in the electrical signals carried by the wires 40. In some examples, wires 40 can be twisted, as a bundle, within the end effector 100 and/or within the shaft 9 to inhibit movement and vibration of the wires 40. Additionally, or alternatively, other strategies for bundling wires 40 to inhibit wire movement can include shrink sleeving the wires 40, using adhesive to join the wires 40, and/or braiding the wires 40. Additionally, or alternatively, pairs of the wires 40 connected to a bipolar pair of electrodes 37 can be twisted within a respective spine 1A, 2A, 3A, 1B, 2B, 3B to promote electromagnetic compatibility between each twisted pair, thereby reducing electrical noise in electrical signals carried by the respective twisted pairs.

What is claimed is:
1. An apparatus comprising:
an elongated shaft comprising a proximal portion and a distal portion, the elongated shaft configured to be manipulated at the proximal portion to position the distal portion into a heart of a patient, the elongated shaft defining a longitudinal axis of the apparatus; and
an end effector disposed proximate the distal portion of the elongated shaft, the end effector comprising three loop members comprising respective pair of ends affixed to the distal portion of the elongated shaft, each of the three loop members comprising a support frame extending through a respective loop member and affixed to the distal portion of the elongated shaft at each end of the respective pair of ends of the respective loop member, the end effector configured to expand to an unconstrained configuration when unconstrained to define three different planes for the respective three loop members, at least two of the three planes being noncoplanar so that the three loop members overlap in a stacked configuration at a common distal vertex when the end effector is placed against a planar surface,
each of the respective support frames defining a respective looped path of the respective loop member when the end effector is in the unconstrained configuration, and
each of the respective support frames comprising a respective pair of parallel segments, each segment in the respective pair of parallel segments comprising a respective length, a majority of the respective length of each segment in each of the respective pairs of parallel segments being approximately coplanar with a majority of the respective length of each of the other segments in each of the respective pairs of parallel segments when the end effector is in a flattened configuration, and the majority of the respective lengths of the segments of at least one of the respective pairs of parallel segments being non-coplanar with the majority of the respective length of at least one segment of the other respective pairs of parallel segments when the end effector is in the unconstrained configuration.

2. The apparatus of claim 1,
each of the respective support frames comprising a respective cross sectional shape orthogonal to the respective looped path, each of the respective cross sectional shapes varying along the respective looped path.

3. The apparatus of claim 1,
the three loop members each comprising:
  an inner tubular housing surrounding at least a portion of the respective support frame;
  an outer tubular housing surrounding at least a portion of the inner tubular housing and bonded to the inner tubular housing; and
  a plurality of electrical conductors disposed at least partially within the outer tubular housing and outside of the inner tubular housing.

4. The apparatus of claim 1, further comprising:
a mechanical linkage binding the three loop members at the distal vertex, the mechanical linkage comprising at least one of:
  a rectangular or ovular shape comprising an opening through which the three loop members extend and a side comprising a seam,
  a rectangular or ovular shape comprising an opening through which the three loop members extend and four contiguous sides,
  a rectangular or ovular shape comprising three openings each comprising a respective loop member of the three loop members extending therethrough,
  a cylindrical shape comprising three passageways therethrough, the three passageways each comprising a respective loop member of the three loop members extending therethrough, and
  a tapered ring comprising an annular opening through which the three loop members extend and a tapered height extending across a diameter of annular opening.

5. The apparatus of claim 1, further comprising:
a plurality of electrodes affixed to the three loop members, each electrode of the plurality of electrodes comprising a surface characterized by roughness parameter Ra representing an arithmetical mean deviation of a profile of the surface, where Ra measures from about 0.3 micrometers to about 0.4 micrometers.

6. The apparatus of claim 1, further comprising:
at least one pull wire extending through the elongated shaft and attached to the distal portion of the elongated shaft so that when the pull wire is retracted toward the proximal portion relative to the elongated shaft, the distal portion and the end effector are bent at an angle with respect to the longitudinal axis.

7. The apparatus of claim 1, one of the planes being contiguous with the longitudinal axis.

8. An apparatus for a mapping catheter comprising:
a tubular member extending along a longitudinal axis;
a first loop member comprising two spine members extending from the tubular member and connected to an arcuate member, the first loop member arrayed on a first plane;
a second loop member comprising two spine members extending from the tubular member and connected to an arcuate member, the second loop member arrayed on a second plane nonparallel to, and intersecting with, the first plane, the second plane being contiguous with the longitudinal axis;
a third loop member comprising two spine members extending from the tubular member and connected to an arcuate member, the third loop member arrayed on a third plane that is nonparallel to, and intersects with, the first plane and the second plane so that a majority of the length of each of the three loop members is non-coplanar with the majority of the length of at least one of the other three loop members in an unconstrained configuration,
each of the first, second and third loop members comprising:
  a plurality of electrodes disposed thereon each loop member; and
  a support frame extending through a respective loop member of the three loop members and affixed to a distal portion of the tubular member, each of the respective support frames defining a respective looped path of the respective loop member, and
  each of the respective support frames comprising a respective pair of parallel segments, each segment in the respective pair of parallel segments comprising a respective length,
the three loop members movable to a flattened configuration when the loop members are positioned against a planar surface, a majority of a length of each of the three loop members being contiguous to the planar surface in the flattened configuration, the arcuate members of the first, second, and third loop members overlapping in the flattened configuration, and a majority of the respective length of each segment in each of the respective pairs of parallel segments being approximately coplanar with a majority of the respective length of each of the other segments in each of the respective pairs of parallel segments when the three loop members are in the flattened configuration, and
the majority of the respective lengths the segments of at least one of the respective pairs of parallel segments being non-coplanar with the majority of the respective length of at least one segment of the other respective pairs of parallel segments when the three loop members are in the unconstrained configuration.

9. The apparatus of claim 8,
each of the respective support frames comprising a respective cross sectional shape orthogonal to the respective looped path, each of the respective cross sectional shapes varying along the respective looped path.

10. The apparatus of claim 8,
the three loop members each comprising:
  an inner tubular housing surrounding at least a portion of the respective support frame;
  an outer tubular housing surrounding at least a portion of the inner tubular housing and bonded to the inner tubular housing; and
  a plurality of electrical conductors disposed at least partially within the outer tubular housing and outside of the inner tubular housing.

11. The apparatus of claim 8, further comprising:
a mechanical linkage binding the arcuate members of the three loop members, the mechanical linkage comprising at least one of:
  a rectangular or ovular shape comprising an opening through which the three loop members extend and a side comprising a seam,
  a rectangular or ovular shape comprising an opening through which the three loop members extend and four contiguous sides, a rectangular or ovular shape comprising three openings each comprising a respective loop member of the three loop members extending therethrough, a cylindrical shape comprising three passageways therethrough, the three passageways each comprising a respective loop member of the three loop members extending therethrough, and a tapered ring comprising an annular opening through which the three loop members extend and a tapered height extending across a diameter of annular opening.

12. The apparatus of claim 8, each electrode of the plurality of electrodes comprising a surface characterized by roughness parameter Ra representing an arithmetical mean deviation of a profile of the surface, where Ra measures from about 0.3 micrometers to about 0.4 micrometers.

13. The apparatus of claim 8, further comprising:

at least one pull wire extending through the tubular member and attached to a distal portion of the tubular member so that when the pull wire is retracted proximally, the distal portion and the three loop members are bent at an angle with respect to the longitudinal axis.

14. An apparatus comprising:

an elongated shaft comprising a proximal portion and a distal portion, the elongated shaft configured to be manipulated at the proximal portion to position the distal portion into a heart of a patient, the elongated shaft defining a longitudinal axis of the apparatus;

an end effector disposed proximate the distal portion of the elongated shaft, the end effector comprising three loop members comprising respective pair of ends affixed to the distal portion of the elongated shaft, the end effector configured to expand to an unconstrained configuration when unconstrained to define three different noncoplanar planes for the respective three loop members, one of the planes coplanar with the longitudinal axis, so that the three loop members overlap in a stacked configuration at a common distal vertex when the end effector is placed against a planar surface, each of the three loop members comprising a support frame extending through a respective loop member of the three loop members and affixed to the distal portion of the elongated shaft at each end of the respective pair of ends of the respective loop member, each of the respective support frames defining a respective looped path of the respective loop member, and each of the respective support frames comprising a respective pair of parallel segments, each segment in the respective pair of parallel segments comprising a respective length, a majority of the respective length of each segment in each of the respective pairs of parallel segments being approximately coplanar with a majority of the respective length of each of the other segments in each of the respective pairs of parallel segments when the end effector is in a flattened configuration, and the majority of the respective lengths of the segments of at least one of the respective pairs of parallel segments being non-coplanar with the majority of the respective length of at least one segment of the other respective pairs of parallel segments when the end effector is in the unconstrained configuration; and a mechanical linkage binding the three loop members at the distal vertex.

15. The apparatus of claim 14, the mechanical linkage comprising:

a tapered ring comprising an annular opening through which the three loop members extend and a tapered height extending across a diameter of the annular opening.

16. The apparatus of claim 15, wherein a first side of the tapered ring is wider than a second side of the tapered ring, and wherein the tapered ring is configured to promote the loop members to fold to a first side of the end effector.

17. The apparatus of claim 14, the mechanical linkage comprising:

a rectangular or ovular shape comprising three openings each comprising a respective loop member of the three loop members extending therethrough, each of the three openings being noncoaxial with the other openings and at least one of the three openings having a substantially circular shape and at least one other of the three openings having an oblong shape.

18. The apparatus of claim 17, each of the respective support frames comprising a respective cross sectional shape orthogonal to the respective looped path, each of the respective cross sectional shapes varying along the respective looped path.

* * * * *